(12) United States Patent
Jin et al.

(10) Patent No.: US 8,822,519 B2
(45) Date of Patent: Sep. 2, 2014

(54) COMPOUND WITH AGITATION EFFECT ON PEROXISOME PROLIFERATOR-ACTIVATED RECEPTOR PROCESS FOR ITS PREPARATION AND USE THEREOF

(75) Inventors: Chunhua Jin, Taizhou (CN); Xiaoyu Liu, Taizhou (CN); Zhenliang Chen, Taizhou (CN); Xiaohe Zheng, Taizhou (CN); Shoufeng Ming, Taizhou (CN)

(73) Assignee: Zhejiang Hisun Pharmaceutical Co., Ltd., Zhejiang (CN)

( * ) Notice: Subject to any disclaimer, the term of this patent is extended or adjusted under 35 U.S.C. 154(b) by 320 days.

(21) Appl. No.: 13/057,737

(22) PCT Filed: Aug. 7, 2009

(86) PCT No.: PCT/CN2009/073140
§ 371 (c)(1),
(2), (4) Date: Aug. 30, 2011

(87) PCT Pub. No.: WO2010/015212
PCT Pub. Date: Feb. 11, 2010

(65) Prior Publication Data
US 2011/0319458 A1    Dec. 29, 2011

(30) Foreign Application Priority Data

Aug. 7, 2008    (CN) .......................... 2008 1 0147310

(51) Int. Cl.
| | | |
|---|---|---|
| C07D 249/12 | (2006.01) | |
| A61K 31/4196 | (2006.01) | |
| A61P 3/00 | (2006.01) | |
| A61P 3/04 | (2006.01) | |
| A61P 3/06 | (2006.01) | |
| A61P 3/10 | (2006.01) | |
| A61P 25/28 | (2006.01) | |
| A61P 5/48 | (2006.01) | |
| A61P 35/00 | (2006.01) | |

(52) U.S. Cl.
CPC .......... C07D 249/12 (2013.01); A61K 31/4196 (2013.01)
USPC ........ 514/384; 514/236.8; 514/374; 548/236; 548/262.2; 548/263.2

(58) Field of Classification Search
CPC .......................... C07D 249/12; A61K 31/4196
USPC ............ 514/236.8, 374, 384; 548/236, 262.2, 548/263.2
See application file for complete search history.

(56) References Cited

U.S. PATENT DOCUMENTS 4,220,789 A * 9/1980 Gozzo et al. ............... 548/263.2

FOREIGN PATENT DOCUMENTS

| CA | 1106387 A2 | 8/1981 | | |
|---|---|---|---|---|
| GB | 1576964 | 10/1980 | | |
| WO | WO 0100603 | 1/2001 | | |
| WO | WO 0238533 A2 | 5/2002 | | |
| WO | WO 02092590 A1 | 11/2002 | | |
| WO | WO 2004063166 | 7/2004 | | |
| WO | WO 2008/103574 | * 8/2008 | ........... | C07D 249/00 |
| WO | WO 2008103574 | 8/2008 | | |

OTHER PUBLICATIONS

Bellioni: Syntheses in the 1,2,4-triazolone series. Annali di Chimica (Rome Italy) 1962, vol. 52, pp. 187-191. Database CA [Online]. Columbus, Ohio, US Chemical Abstracts Service [retrieved on Apr. 22, 2001]. Retrieved from STN International, Columbus, USA. AN: 57:23199.

(Continued)

*Primary Examiner* — Michael Barker
*Assistant Examiner* — Amanda L Aguirre
(74) *Attorney, Agent, or Firm* — Knobbe, Martens, Olson & Bear LLP

(57) ABSTRACT

The present invention provides a novel compound of formula I, which has an agitation effect on the peroxisome proliferator-activated receptor subtype δ (PPARδ), to a pharmaceutical composition comprising the compound, to a process for preparation of the compound and to use of the compound in the manufacture of a medicament for treating or preventing a disease which could be treated or prevented by activating PPARδ thereof, said disease is one or more from the group comprising metabolic syndrome, obesity, dyslipidemia, pathoglycemia, insulin resistance, senile dementia and tumors. The present invention also relates to a new intermediate used in the preparation of the novel compound and a process for preparation of the intermediate.

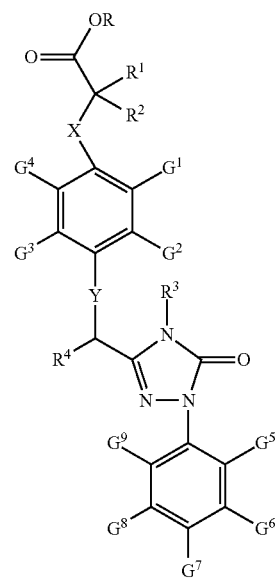

21 Claims, 2 Drawing Sheets

(56) References Cited

OTHER PUBLICATIONS

Berger et al., "Novel Peroxisome Proliferator-activated Receptor (PPAR) γ and PPARδ Ligands Produce Distinct Biological Effects," J. Biol. Chem., 274 (10):6718-6725 (1999).

Buck et al.: N-ETHYL-mTOLUIDINE; Org. Syn. Coll. vol. 2, p. 290 (1943); vol. 18, p. 40 (1938).

Guan, "Peroxisome Proliferator-Activated Receptor Family and Its Relationship to Renal Complications of the Metabolic Syndrome," Am. Soc. Nephroi, 15: 2801-2815 (2004).

Handbook of Fine Organic Chemical Raw Materials and Intermediate, XU Ke-xun (Eds), Scientific & Technological Industry Press, pp. 3-426-3-584 (2004).

Kasuga et al., "Design, synthesis, and evaluation of potent, structurally novel peroxisome proliferator-activated receptor (PPAR) δ-selective agonists", Bioorg. Med Chem., vol. 15, pp. 5177-5190 (2007).

Li et al., "Design, synthesis and evaluation of a new class of noncyclic 1,3-dicarbonyl compounds as PPARa selective activators", Bioorg Med Chem Lett., 14(13): 3507-3511 (2004).

Oliver et al, "A selective peroxisome proliferator-activated receptor δ agonist promotes reverse cholesterol transport," Natl. Acad. Sci. U.S.A., 98: 5306-5311 (2001).

Sauerberg et al., "Identification and Synthesis of a Novel Selective Partial PPARδ Agonist with Full Efficacy on Lipid Metabolism In Vitro and In Vivo" J. Med. Chem., 50: 1495-1503 (2007).

Sznaidman et al., "Novel selective small molecule agonists for peroxisome proliferator-activated receptor δ (PPARδ)-synthesis and biological activity", Bioorg. Med. Chem. Lett., 13(9): 1517-1521 (2003).

Wei & Kozikowski, "A Short and Efficient Synthesis of the Pharmacological Research Tool GW501516 for the Peroxisome Proliferator-Activated Receptor δ", J. Org. Chem., 68: 9116-9118 (2003).

Willson et al.: Benzylaniline; Org. Syn. Coll. vol. 1, p. 102 (1941); vol. 8, p. 38 (1928).

International Search Report and Written Opinion dated Nov. 19, 2009 for PCT Application No. PCT/CN2009/073140, filed Aug. 7, 2009.

* cited by examiner

COMPOUND WITH AGITATION EFFECT ON PEROXISOME PROLIFERATOR-ACTIVATED RECEPTOR PROCESS FOR ITS PREPARATION AND USE THEREOF

RELATED APPLICATIONS

The instant application is the U.S. National Phase under 35 U.S.C. §371 of International Application No. PCT/CN2009/073140 entitled COMPOUND WITH AGITATION EFFECT ON PEROXISOME PROLIFERATOR-ACTIVATED RECEPTOR δ, AND PREPARATION METHOD AND USE THEREOF, filed Aug. 7, 2009, designating the U.S. and published in Chinese on Feb. 11, 2010 as WO2010/015212, which claims priority to Chinese Application No. 200810147310.0 filed on Aug. 7, 2008. The content of these applications are herein incorporated by reference in their entireties.

FIELD OF THE INVENTION

The present invention relates to novel compounds with an agitation effect on a peroxisome proliferator-activated receptor subtype δ (PPAR δ), to a process for preparation of the same, to medicaments comprising the compounds, and to applications of these compounds in treatment and prevention of cardiovascular diseases and the like. The present invention also relates to a new intermediate for the novel compounds and to a process for preparation of the intermediate.

BACKGROUND OF THE INVENTION

In the present world, along with a high-speed development and raising living standards, people intake excessive fat and protein which result in global occurrence of the metabolic syndrome characterized by obesity, insulin resistance (Type II diabetes), lipid metabolic disorder and hypertension. These represent great threats to human health. In addition to the individual's genetic characteristics, age, sex, physiological nature, nutritional status, diet habit, etc., the metabolic syndrome is associated with imbalance in lipid metabolism, energy and carbohydrate metabolism in vivo. Thus, an effective method of treating the metabolic syndrome is a therapeutic regime aimed to maintain or restore balance in vivo in energy, fat and carbohydrate. As nuclear receptors (NRs) play a key role in maintenance of balance in vivo in energy, lipids and carbohydrates within a cell, as well as within whole individual's body, they become a focus of researches. Only when being activated by various physiological ligands (e.g., saturated fatty acids, unsaturated fatty acids, metabolites thereof, and various synthetic compounds), can the nuclear receptor regulate transcription systems of responsive genes, thus exert its physiological activity (Kasuga, J. et al., *Bioorg. Med. Chem.* 2007, 15, 5177-5190).

Among the nuclear receptor families, peroxisome proliferator activated receptors (PPARs) have attracted peoples' attention for more than ten years, which are nuclear transcription factors activated by their ligand and which act as a crucial regulatory factors in the metabolic syndrome (Guan, Y. *J. Am. Soc. Nephrol,* 2004, 15, 2801-2815). Therefore, PPARs play an important role in the genesis, development and control of diseases such as insulin resistance, impaired glucose tolerance, Type II diabetes, obesity, hyperlipidemia, hypertension, angiocardiopathy, artherosclerosis, etc.

PPARs are classified into three subtypes: PPARα, PPARδ and PPARγ, which regulate expression of the gene by binding to specific DNA sequence of a gene (Berger, J. et al., *The Journal of Biological Chemistry,* 1999, 274 (10), 6718-6725). PPARα is mainly expressed in the liver, heart, intestinal tract, kidney and macrophage, and, after being activated, can increase the metabolism of fatty acids, alleviate the Inflammatory response in macrophages, and reduce low density lipoprotein cholesterol; PPARγ is expressed in the adipocyte, placentoma and other tissues, and, after being activated, can not only lower the blood glucose level and increase the insulin sensitivity, but also play a key role in lipid metabolism, cytokine antagonization, anti-inflammation, immuno regulation and blood pressure regulation, etc. (Kasuga, J. et al., *Bioorg. Med. Chem.* 2007, 15, 5177-5190). In contrast to the other two subtypes, the physiologic function of the PPARδ is not clear up to now.

However, it has been shown in recent studies on animal models for pharmacology experiments that, the PPARδ can increase the fatty acid catabiosis and energy uncoupling in adipose tissue and muscle, and can suppress the macrophage-originated inflammation. Due to various functions in controlling gaining weight of human body, enhancing body's durability, increasing the insulin sensitivity and improving artherosclerosis, the ligands for the PPARδ may be an effective medicament for the treatment of hyperlipidemia, obesity, insulin resistance, and artherosclerosis.

At present, none of PPARδ receptor agonist agents are commercially available as a medicament. Among the present researches on the PPARδ agonists, clinical research on GW501516 developed by GlaxoSmithKline has shown that GW501516 may increase the level of high density lipoprotein (HDL) cholesterol up to 80%, lower the level of low density lipoprotein (LDL) cholesterol up to 29%, decrease the level of triglyceride (TG) up to 56%, decrease the level of insulin up to 48% (Oliver, W.; Jr.; Shenk, J. L. et al, *Natl. Acad. Sci. U.S.A.* 2001, 98, 5306-5311). Thus, it is believed that GW501516 can become an effective medicament for the treatment of obesity and cardiovascular diseases (WO01/00603A1, *Bioorg. Med. Chem. Lett.* 2003, 13, 1517). However, GW501516 project has been now temporarily suspended due to unfavorable results from its Phase II clinical trial.

Thus, there is an urgent need for providing a novel compound which has an agonisting action on peroxisome proliferator-activated receptor subtype δ (PPARδ) and a much better ability of regulating blood lipids than that of GW501516.

SUMMARY OF THE INVENTION

One object of the present invention is to provide a compound of formula (I) and/or its pharmaceutically acceptable salts and/or solvates thereof:

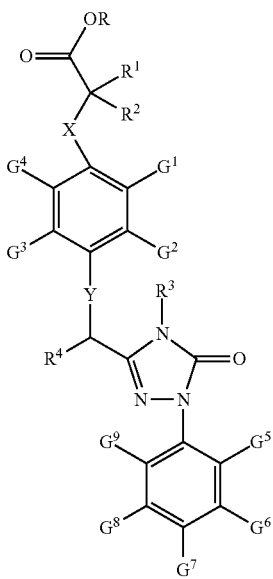

Wherein,
1) X is O, S, N, or $(CH_2)_n$, in which n is an integer from 1 to 4, X is preferably O, S, or $CH_2$;
2) Y is O, S or N, preferably O or S;
3) R is H or C1-C9 alkyl, preferably H, methyl, or ethyl;
4) $R^1$ and $R^2$ are independently from each other H or C1-C4 alkyl, and at least one of $R^1$ and $R^2$ is H; preferably, $R^1$ and $R^2$ are independently from each other methyl, ethyl, or H;
5) $R^3$ is H, C1-C9 alkyl, preferably H or C1-C4 alkyl, e.g., methyl, ethyl, isopropyl, and more preferably methyl;
6) $R^4$ is H, C1-C9 alkyl, C3-C7 cycloalkyl, phenyl, or substituted phenyl, the substituent group of the substituted phenyl is selected from C1-C9 alkyl, hydroxyl, C1-C9 alkoxy, mercapto, C1-C9 alkylthio, trifluoromethyl, F, Cl, Br, nitro, $NR^5R^6$, $COOR^5$, $NR^5COR^6$, or $CONR^5R^6$; $R^5$ and $R^6$ are independently from each other H or C1-C9 alkyl, and when $R^4$ is substituted phenyl, the substituent group is preferably 4-methoxy or 4-methyl;
7) $G^1$ and $G^4$ are individually H, C1-C9 alkyl, hydroxyl, C1-C9 alkoxy, mercapto, C1-C9 alkylthio, trifluoromethyl, F, Cl, Br, nitro, $NR^5R^6$, $COOR^5$, $NR^5COR^6$, or $CONR^5R^6$; $R^5$ and $R^6$ are independently from each other H or C1-C9 alkyl; preferably, $G^1$ and $G^4$ are individually methyl or ethyl;
8) $G^2$ and $G^3$ are individually H, C1-C9 alkyl, hydroxyl, C1-C9 alkoxy, mercapto, C1-C9 alkylthio, trifluoromethyl, F, Cl, Br, nitro, $NR^5R^6$, $COOR^5$, $NR^5COR^6$, or $CONR^5R^6$; $R^5$ and $R^6$ are independently from each other H or C1-C9 alkyl; preferably, $G^2$ and $G^3$ are individually methyl, ethyl, or H;
9) $G^5$, $G^6$, $G^8$, and $G^9$ are individually H, C1-C9 alkyl, hydroxyl, C1-C9 alkoxy, mercapto, C1-C9 alkylthio, trifluoromethyl, F, Cl, Br, nitro, $NR^5R^6$, $COOR^5$, $NR^5COR^6$, or $CONR^5R^6$; $R^5$ and $R^6$ are independently from each other H or C1-C9 alkyl; preferably, $G^5$, $G^6$, $G^8$, and $G^9$ are individually H, F, Cl, Br, methyl, ethyl, or methoxy; and
10) $G^7$ is H, C1-C9 alkyl, hydroxyl, C1-C9 alkoxy, mercapto, C1-C9 alkylthio, trifluoromethyl, F, Cl, Br, nitro, $NR^5R^6$, $COOR^5$, $NR^5COR^6$, or $CONR^5R^6$; $R^5$ and $R^6$ are independently from each other H or C1-C9 alkyl; preferably, $G^7$ is trifluoromethyl, isopropyl, ethyl, methyl, or Cl; more preferably, $G^7$ is trifluoromethyl.

When the compound of the present invention is in an ester form, it is referred to hereinafter as the compound I (ester).

The preferred compound I (ester) of the present invention comprises the following compounds:
Ethyl-2-(2-methyl-4-(1-(3-(4-methyl-5-oxo-1-(4-trifluoromethyl-phenyl)-4,5-dihydrogen-1H-1,2,4-triazolyl))-benzyloxy)-phenoxy)-acetate (hereinafter known as "E-1");
Ethyl-2-(2-methyl-4-(1-(3-(4-methyl-5-oxo-1-(4-trifluoromethyl-phenyl)-4,5-dihydrogen-1H-1,2,4-triazolyl))-benzyloxy)-phenylthio)-acetate (hereinafter known as "E-2");
Ethyl-2-(3-methyl-4-(1-(3-(4-methyl-5-oxo-1-(4-trifluoromethyl-phenyl)-4,5-dihydrogen-1H-1,2,4-triazolyl))-benzyloxy)-phenylthio)-acetate (hereinafter known as "E-3");
Ethyl-2-(2-methyl-4-(1-(3-(4-methyl-5-oxo-1-(4-trifluoromethyl-phenyl)-4,5-dihydrogen-1H-1,2,4-triazolyl))-benzylthio)-phenoxy)-acetate (hereinafter known as "E-4");
Ethyl-2-(2-ethyl-4-(1-(3-(4-methyl-5-oxo-1-(4-trifluoromethyl-phenyl)-4,5-dihydrogen-1H-1,2,4-triazolyl))-benzyloxy)-phenoxy)-acetate (hereinafter known as "E-5");
Ethyl2-(3-methyl-4-(1-(3-(4-methyl-5-oxo-1-(4-trifluoromethyl-phenyl)-4,5-dihydrogen-1H-1,2,4-triazolyl))-benzyloxy)-phenoxy)-acetate (hereinafter known as "E-6");
Ethyl2-(3-methyl-4-(1-(3-(4-methyl-5-oxo-1-(4-trifluoromethyl-phenyl)-4,5-dihydrogen-1H-1,2,4-triazolyl))-benzylthio)-phenoxy)-acetate (hereinafter known as "E-7");
Ethyl2-(2-methyl-4-(3-(4-methyl-5-oxo-1-(4-trifluoromethyl-phenyl)-4,5-dihydrogen-1H-1,2,4-triazolyl)-methylthio)-phenoxy)-acetate (hereinafter known as "E-8");
Ethyl2-(2-methyl-4-(3-(4-methyl-5-oxo-1-(4-trifluoromethyl-phenyl)-4,5-dihydrogen-1H-1,2,4-triazolyl)-methoxy)-phenoxy)-acetate (hereinafter known as "E-9");
Ethyl2-(2,5-dimethyl-4-(1-(3-(4-methyl-5-oxo-1-(4-trifluoromethyl-phenyl)-4,5-dihydrogen-1H-1,2,4-triazolyl))-benzylthio)-phenoxy)-acetate (hereinafter known as "E-10");
Ethyl2-(2,5-dimethyl-4-(1-(3-(4-methyl-5-oxo-1-(4-trifluoromethyl-phenyl)-4,5-dihydrogen-1H-1,2,4-triazolyl))-benzyloxy)-phenylthio)-acetate (hereinafter known as "E-11");
Ethyl2-(3-methyl-4-(3-(4-methyl-5-oxo-1-(4-trifluoromethyl-phenyl)-4,5-dihydrogen-1H-1,2,4-triazolyl)-methoxy)-phenylthio)-acetate (hereinafter known as "E-12");
Methyl 2-methyl-2-(2-methyl-4-(1-(3-(4-methyl-5-oxo-1-(4-trifluoromethyl-phenyl)-4,5-dihydrogen-1H-1,2,4-triazolyl))-benzylthio)-phenoxy)-acetate (hereinafter known as "E-13");
Ethyl 2-(2-ethyl-4-(1-(3-(4-methyl-5-oxo-1-(4-trifluoromethyl-phenyl)-4,5-dihydrogen-1H-1,2,4-triazolyl))-benzylthio)-phenoxy)-acetate (hereinafter known as "E-14");
Ethyl 2,2-dimethyl-2-(3-methyl-4-(1-(3-(4-methyl-5-oxo-1-(4-trifluoromethyl-phenyl)-4,5-dihydrogen-1H-1,2,4-triazolyl))-benzyloxy)-phenylthio)-acetate (hereinafter known as "E-15");
Ethyl 2,2-dimethyl-2-(2-methyl-4-(1-(3-(4-methyl-5-oxo-1-(4-trifluoromethyl-phenyl)-4,5-dihydrogen-1H-1,2,4-triazolyl))-benzylthio)-phenoxy)-acetate (hereinafter known as "E-16");
Ethyl2-(3-methyl-4-(1-(3-(4-n-butyl-5-oxo-1-(4-trifluoromethyl-phenyl)-4,5-dihydrogen-1H-1,2,4-triazolyl))-benzyloxy)-phenylthio)-acetate (hereinafter known as "E-17");
Ethyl 2,2-dimethyl-2-(2-methyl-4-(1-(3-(4-n-butyl-5-oxo-1-(4-trifluoromethyl-phenyl)-4,5-dihydrogen-1H-1,2,4-triazolyl))-benzylthio)-phenoxy)-acetate (hereinafter known as "E-18");

Ethyl2-(2,5-dimethyl-4-(1-(3-(4-n-butyl-5-oxo-1-(4-trifluoromethyl-phenyl)-4,5-dihydrogen-1H-1,2,4-triazolyl))-benzylthio)-phenoxy)-acetate (hereinafter known as "E-19").

The compound I (ester) can be hydrolyzed under alkaline condition to obtain its acidic form, which is referred to hereinafter as the compound I (acid). Preferably, the alkaline condition is formed using an alkali which is an alkali metal hydroxide, including but not limited to sodium hydroxide, lithium hydroxide, potassium hydroxide, and the like; the solvent system used in the hydrolysis is C1-C4 alcohol (e.g., methanol, ethanol, propanol, butanol, and the like)-water (the ratio of alcohol:water=9-1:1 (vol/vol)), tetrahydrofuran (THF) —water (the ratio of THF:water=9-1:1 (vol/vol)), or alcohol-dichloromethane-water (the ratio of alcohol:dichloromethane:water=9-1:9-1:1 (vol/vol)); the reaction temperature is at 0-80° C.; preferably at 20-40° C.; the reaction time is 1-12 hours, preferably 2-4 hours.

The preferred compound I (acid) of the present invention comprises the following compounds:

2-(2-methyl-4-(1-(3-(4-methyl-5-oxo-1-(4-trifluoromethyl-phenyl)-4,5-dihydrogen-1H-1,2,4-triazolyl))-benzyloxy)-phenoxy)-acetic acid (hereinafter known as "A-1");

2-(2-methyl-4-(1-(3-(4-methyl-5-oxo-1-(4-trifluoromethyl-phenyl)-4,5-dihydrogen-1H-1,2,4-triazolyl))-benzyloxy)-phenylthio)-acetic acid (hereinafter known as "A-2");

2-(3-methyl-4-(1-(3-(4-methyl-5-oxo-1-(4-trifluoromethyl-phenyl)-4,5-dihydrogen-1H-1,2,4-triazolyl))-benzyloxy)-phenylthio)-acetic acid (hereinafter known as "A-3");

2-(2-methyl-4-(1-(3-(4-methyl-5-oxo-1-(4-trifluoromethyl-phenyl)-4,5-dihydrogen-1H-1,2,4-triazolyl))-benzylthio)-phenoxy)-acetic acid (hereinafter known as "A-4");

2-(2-ethyl-4-(1-(3-(4-methyl-5-oxo-1-(4-trifluoromethyl-phenyl)-4,5-dihydrogen-1H-1,2,4-triazolyl))-benzyloxy)-phenoxy)-acetic acid (hereinafter known as "A-5");

2-(3-methyl-4-(1-(3-(4-methyl-5-oxo-1-(4-trifluoromethyl-phenyl)-4,5-dihydrogen-1H-1,2,4-triazolyl))-benzyloxy)-phenoxy)-acetic acid (hereinafter known as "A-6");

2-(3-methyl-4-(1-(3-(4-methyl-5-oxo-1-(4-trifluoromethyl-phenyl)-4,5-dihydrogen-1H-1,2,4-triazolyl))-benzylthio)-phenoxy)-acetic acid (hereinafter known as "A-7");

2-(2-methyl-4-(3-(4-methyl-5-oxo-1-(4-trifluoromethyl-phenyl)-4,5-dihydrogen-1H-1,2,4-triazolyl)-methylthio)-phenoxy)-acetic acid (hereinafter known as "A-8");

2-(2-methyl-4-(3-(4-methyl-5-oxo-1-(4-trifluoromethyl-phenyl)-4,5-dihydrogen-1H-1,2,4-triazolyl)-methoxy)-phenoxy)-acetic acid (hereinafter known as "A-9");

2-(2,5-dimethyl-4-(1-(3-(4-methyl-5-oxo-1-(4-trifluoromethyl-phenyl)-4,5-dihydrogen-1H-1,2,4-triazolyl))-benzylthio)-phenoxy)-acetic acid (hereinafter known as "A-10");

2-(2,5-dimethyl-4-(1-(3-(4-methyl-5-oxo-1-(4-trifluoromethyl-phenyl)-4,5-dihydrogen-1H-1,2,4-triazolyl))-benzyloxy)-phenylthio)-acetic acid (hereinafter known as "A-11");

2-(3-methyl-4-(3-(4-methyl-5-oxo-1-(4-trifluoromethyl-phenyl)-4,5-dihydrogen-1H-1,2,4-triazolyl)-methoxy)-phenylthio)-acetic acid (hereinafter known as "A-12");

2-methyl-2-(2-methyl-4-(1-(3-(4-methyl-5-oxo-1-(4-trifluoromethyl-phenyl)-4,5-dihydrogen-1H-1,2,4-triazolyl))-benzylthio)-phenoxy)-acetic acid (hereinafter known as "A-13");

2-(2-ethyl-4-(1-(3-(4-methyl-5-oxo-1-(4-trifluoromethyl-phenyl)-4,5-dihydrogen-1H-1,2,4-triazolyl))-benzylthio)-phenoxy)-acetic acid (hereinafter known as "A-14");

2,2-dimethyl-2-(3-methyl-4-(1-(3-(4-methyl-5-oxo-1-(4-trifluoromethyl-phenyl)-4,5-dihydrogen-1H-1,2,4-triazolyl))-benzyloxy)-phenylthio)-acetic acid (hereinafter known as "A-15");

2,2-dimethyl-2-(2-methyl-4-(1-(3-(4-methyl-5-oxo-1-(4-trifluoromethyl-phenyl)-4,5-dihydrogen-1H-1,2,4-triazolyl))-benzylthio)-phenoxy)-acetic acid (hereinafter known as "A-16");

2-(3-methyl-4-(1-(3-(4-n-butyl-5-oxo-1-(4-trifluoromethyl-phenyl)-4,5-dihydrogen-1H-1,2,4-triazolyl))-benzyloxy)-phenylthio)-acetic acid (hereinafter known as "A-17");

2,2-dimethyl-2-(2-methyl-4-(1-(3-(4-n-butyl-5-oxo-1-(4-trifluoromethyl-phenyl)-4,5-dihydrogen-1H-1,2,4-triazolyl))-benzylthio)-phenoxy)-acetic acid (hereinafter known as "A-18");

2-(2,5-dimethyl-4-(1-(3-(4-n-butyl-5-oxo-1-(4-trifluoromethyl-phenyl)-4,5-dihydrogen-1H-1,2,4-triazolyl))-benzylthio)-phenoxy)-acetic acid (hereinafter known as "A-19").

The particularly preferred compound I (acid) of the present invention comprises the following compounds:

2-(3-methyl-4-(1-(3-(4-methyl-5-oxo-1-(4-trifluoromethyl-phenyl)-4,5-dihydrogen-1H-1,2,4-triazolyl))-benzyloxy)-phenylthio)-acetic acid (A-3);

2-(2-methyl-4-(1-(3-(4-methyl-5-oxo-1-(4-trifluoromethyl-phenyl)-4,5-dihydrogen-1H-1,2,4-triazolyl))-benzylthio)-phenoxy)-acetic acid (A-4);

2-(2,5-dimethyl-4-(1-(3-(4-methyl-5-oxo-1-(4-trifluoromethyl-phenyl)-4,5-dihydrogen-1H-1,2,4-triazolyl))-benzyloxy)-phenylthio)-acetic acid (A-11);

2-(2-ethyl-4-(1-(3-(4-methyl-5-oxo-1-(4-trifluoromethyl-phenyl)-4,5-dihydrogen-1H-1,2,4-triazolyl))-benzylthio)-phenoxy)-acetic acid (A-14);

2,2-dimethyl-2-(3-methyl-4-(1-(3-(4-methyl-5-oxo-1-(4-trifluoromethyl-phenyl)-4,5-dihydrogen-1H-1,2,4-triazolyl))-benzyloxy)-phenylthio)-acetic acid (A-15);

2,2-dimethyl-2-(2-methyl-4-(1-(3-(4-methyl-5-oxo-1-(4-trifluoromethyl-phenyl)-4,5-dihydrogen-1H-1,2,4-triazolyl))-benzylthio)-phenoxy)-acetic acid (A-16);

2-(3-methyl-4-(1-(3-(4-n-butyl-5-oxo-1-(4-trifluoromethyl-phenyl)-4,5-dihydrogen-1H-1,2,4-triazolyl))-benzyloxy)-phenylthio)-acetic acid (A-17);

2,2-dimethyl-2-(2-methyl-4-(1-(3-(4-n-butyl-5-oxo-1-(4-trifluoromethyl-phenyl)-4,5-dihydrogen-1H-1,2,4-triazolyl))-benzylthio)-phenoxy)-acetic acid (A-18);

2-(2,5-dimethyl-4-(1-(3-(4-n-butyl-5-oxo-1-(4-trifluoromethyl-phenyl)-4,5-dihydrogen-1H-1,2,4-triazolyl))-benzylthio)-phenoxy)-acetic acid (A-19).

A pharmaceutically acceptable salt of the compound of formula I according to the present invention refers to an alkali metal or alkaline earth metal salt thereof. Potassium, sodium and calcium salts are preferred.

A solvate of the compound of formula I according to the present invention refers to its hydrate or organic solvate, preferably a hydrate and an alcoholate. The hydrate may contain 1-4 water molecules. The alcoholate may comprise an alcoholate formed with methanol, ethanol, and propanol.

Another object of the invention is to provide a novel compound, i.e. the compound III:

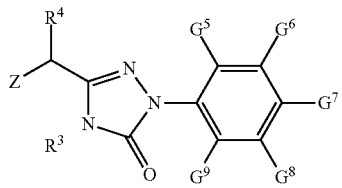

wherein
Z is Cl or Br;
$R^3$ is H or C1-C9 alkyl;
$R^4$ is H, C1-C9 alkyl, C3-C7 cycloalkyl, phenyl or substituted phenyl; the substituent group on the phenyl is selected from C1-C9 alkyl, hydroxyl, C1-C9 alkoxy, mercapto, C1-C9 alkylthio, trifluoromethyl, F, Cl, Br, nitro, $NR^5R^6$, $COOR^5$, $NR^5COR^6$ or $CONR^5R^6$; and
$G^5$, $G^6$, $G^7$, $G^8$, and $G^9$ are independently from each other H, C1-C9 alkyl, hydroxyl, C1-C9 alkoxy, mercapto, C1-C9 alkylthio, trifluoromethyl, F, Cl, Br, nitro, $NR^5R^6$, $COOR^5$, $NR^5COR^6$ or $CONR^5R^6$; $R^5$ and $R^6$ are independently from each other H or C1-C9 alkyl.

The preferred compound III of the present invention comprises the following compounds:
3-(1'-bromo-benzyl)-4-methyl-1-(4-trifluoromethyl)phenyl-1H-1,2,4-triazole-5(4H)-one (hereinafter known as "III-1");
3-(1'-bromo-benzyl)-4-n-butyl-1-(4-trifluoromethyl)phenyl-1H-1,2,4-triazole-5(4H)-one (hereinafter known as "III-2");
3-bromomethyl-4-methyl-1-(4-trifluoromethyl-phenyl)-1,4-dihydrogen-1,2,4-triazole-5-one (hereinafter known as "III-3").

The compound III of the present invention may be used as an intermediate for preparing the compound of formula I according to the present invention.

Another object of the invention is to provide a process for preparation of the compound of formula III.

The compound of formula III according to the present invention can be synthesized by reacting the compound of formula VI with a chlorinating or brominating reagent:

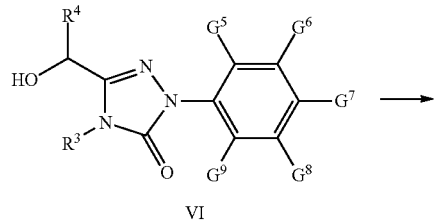

wherein
Z is Cl or Br; $R^3$, $R^4$, $G^5$-$G^9$ are the same as given in definition of the compound of formula III.

The chlorinating or brominating reagent is selected from:
(1) N-bromosuccinimide (NBS)/triphenylphosphine ($Ph_3P$);
(2) Thionyl chloride ($SOCl_2$) or thionyl bromide ($SOBr_2$);
(3) N-chlorosuccinimide (NCS)/triphenylphosphine ($Ph_3P$);
(4) carbon tetrachloride ($CCl_4$) or carbon tetrabromide ($CBr_4$)/triphenylphosphine ($Ph_3P$);
(5) phosphorous pentachloride ($PCl_5$) or phosphorus pentabromide ($PBr_5$);
(6) phosphorus oxychloride ($POCl_3$) or phosphorus oxybromide ($POBr_3$); and
(7) phosphorus trichloride ($PCl_3$) or phosphorus tribromide ($PBr_3$).

The solvent is selected from dichloromethane, chloroform, carbon tetrachloride, and any mixtures thereof; the reaction temperature is at 10-80° C.; the reaction time is 2-8 hours.

The compound of formula III is preferably synthesized according to the following scheme:

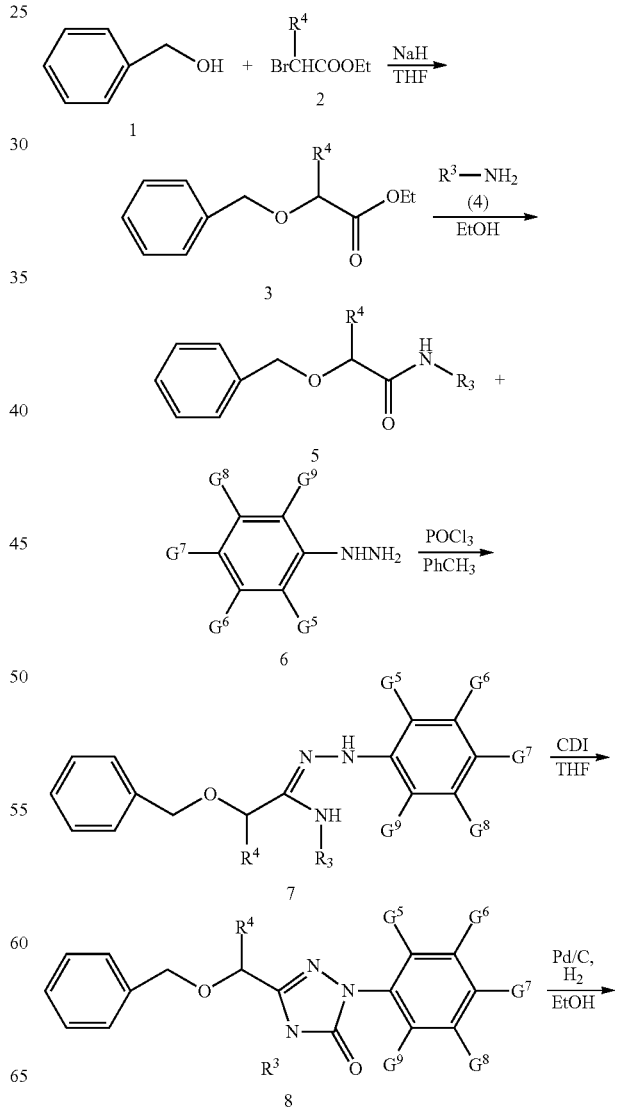

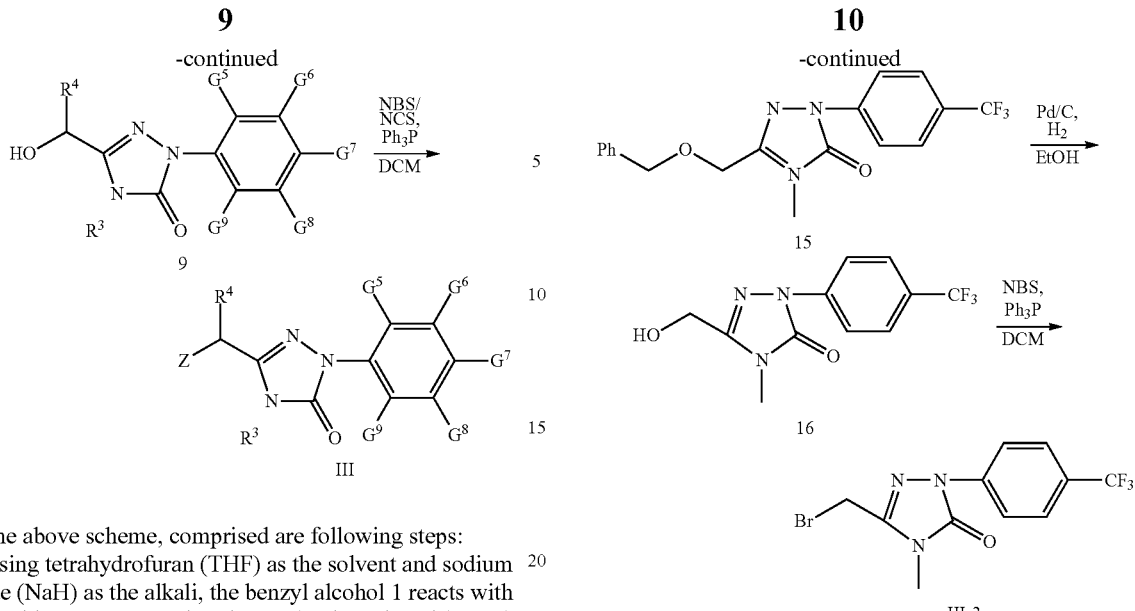

In the above scheme, comprised are following steps:

1) using tetrahydrofuran (THF) as the solvent and sodium hydride (NaH) as the alkali, the benzyl alcohol 1 reacts with the bromide 2 to generate the ether 3; 2) using ethanol (EtOH) as the solvent, the ether 3 is aminated with the amine 4 to generate the amide 5;

3) using toluene (PhCH$_3$) as the solvent, the amide 5 reacts with phenylhydrazine 6 under the action of phosphorus oxychloride (POCl$_3$) to generate the hydrazone 7;

4) using tetrahydrofuran (THF) as the solvent, the hydrazone 7 reacts with carbonyldiimidazole (CDI) to generate the compound 8; 5) using ethanol (EtOH) as the solvent and palladium on carbon (Pd/C) as the catalyst, the benzyl is split from the compound 8 by means of hydrogenation under normal pressure to generate the alcohol 9;

6) using dichloromethane (DCM) as the solvent, the alcohol 9 is converted into the compound III under the action of the chlorinating or brominating reagent.

For example, when $R^4$, $G^5$, $G^6$, $G^8$, $G^9$ are H, $R^3$ is methyl, and $G^7$ is trifluoromethyl, the synthesis scheme is as follows:

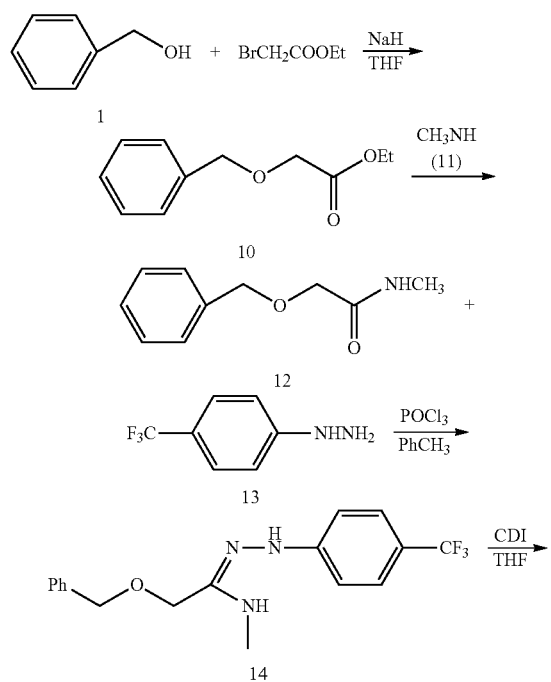

In the above scheme, comprised are following steps:

1) using tetrahydrofuran (THF) as the solvent and sodium hydride (NaH) as the alkali, upon heating under reflux, the benzyl alcohol 1 reacts with ethyl bromoacetate to generate the ethyl benzyloxyacetate 10;

2) using ethanol (EtOH) as the solvent, the ethyl benzyloxyacetate 10 is aminated with the methylamine 11 at room temperature to generate the benzyloxy acetomethylamine12;

3) using toluene (PhCH$_3$) as the solvent, the benzyloxy acetomethylamine12 reacts with the p-trifluoromethyl phenylhydrazine 13 at 80° C. under the action of phosphorus oxychloride (POCl$_3$) to generate the hydrazone 14;

4) using tetrahydrofuran (THF) as the solvent, the hydrazone 14 reacts with carbonyldiimidazole (CDI) to generate the compound 15;

5) using ethanol (EtOH) as the solvent and palladium on carbon (Pd/C) as the catalyst, the benzyl is split from the compound 15 at room temperature by means of hydrogenation under normal pressure to generate the alcohol 16;

6) using dichloromethane (DCM) as the solvent and N-bromosuccinimide (NBS) as the brominating reagent, the alcohol 16 is converted into the compound III-3 under the action of triphenylphosphine (Ph$_3$P).

The compound of formula IIIb can also be synthesized by reacting the compound of formula VII with a chlorinating or brominating reagent; the solvent is chloroform or carbon tetrachloride, the brominating reagent is N-bromosuccinimide (NBS), the chlorinating reagent is N-chlorosuccinimide (NCS), the catalyst is dibenzoyl peroxide, the reaction temperature is at 40-80° C., the reaction time is 2-8 hours.

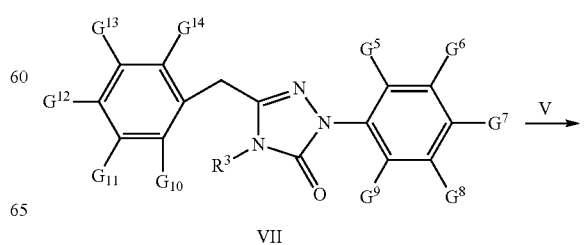

-continued

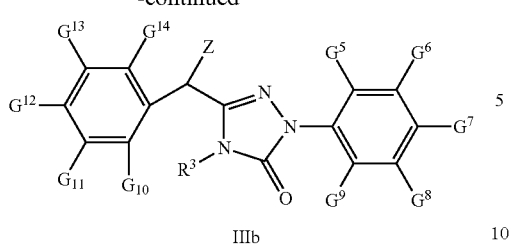

IIIb wherein

Z is Cl or Br;

$R^3$, $G^5$-$G^9$ are the same as given in definition of the compound of formula III;

$G^{10}$-$G^{14}$ are independently from each other or simultaneously H, C1-C9 alkyl, hydroxyl, $C_1$-$C_9$ alkoxy, mercapto, $C_1$-$C_9$ alkylthio, trifluoromethyl, F, Cl, Br, nitro, $NR^5R^6$, $COOR^5$, $NR^5COR^6$, or $CONR^5R^6$;

$R^5$ and $R^6$ are independently from each other H or C1-C9 alkyl.

The compound of formula IIIb is preferably prepared according to the following scheme:

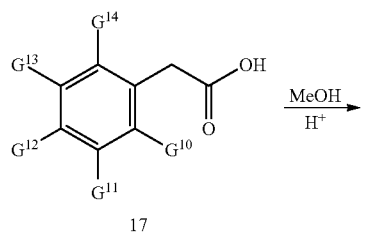

17

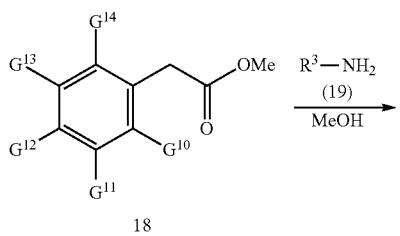

18

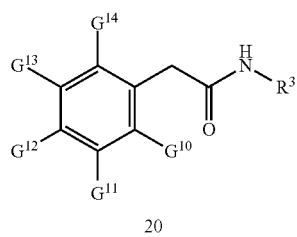

20

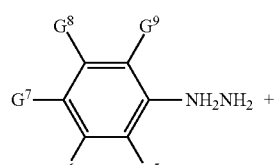

6

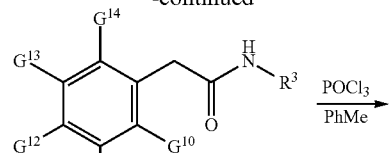

20

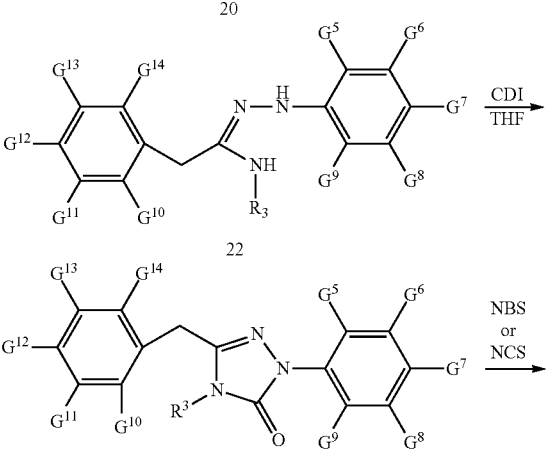

22

23

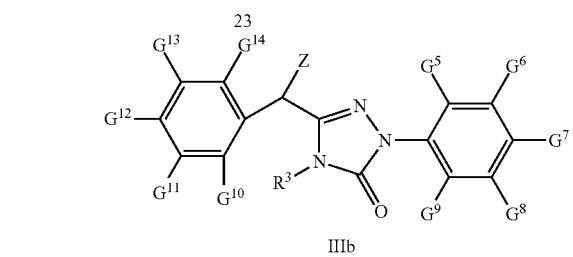

IIIb

In the above scheme, comprised are following steps:

1) using methanol (MeOH) as the solvent and sulphuric acid as the catalyst, the acid 17 undergoes esterification to generate the ester 18;

2) using methanol (MeOH) as the solvent, the ester 18 is aminated with the amine 19 to generate the amide 20;

3) using toluene ($PhCH_3$) as the solvent, the amide 20 reacts with the phenylhydrazine 6 under the action of phosphorus oxychloride ($POCl_3$) to generate the hydrazone 22; 4) using tetrahydrofuran (THF) as the solvent, the hydrazone 22 reacts with carbonyldiimidazole (CDI) to generate the compound 23;

5) using chloroform as the solvent, N-bromosuccinimide (NBS) as the brominating reagent (or N-chlorosuccinimide (NCS) as chlorinating reagent), and dibenzoyl peroxide as the catalyst, the compound 23 is brominated (or chlorinated) to generate the compound III.

For example, when $R^4$ is phenyl, $G^5$, $G^6$, $G^8$, $G^9$ are H, $R^3$ is methyl, and $G^7$ is trifluoromethyl, the synthesis scheme is as follows:

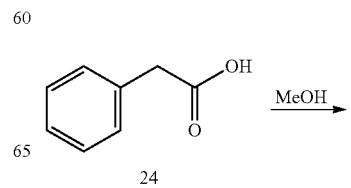

24

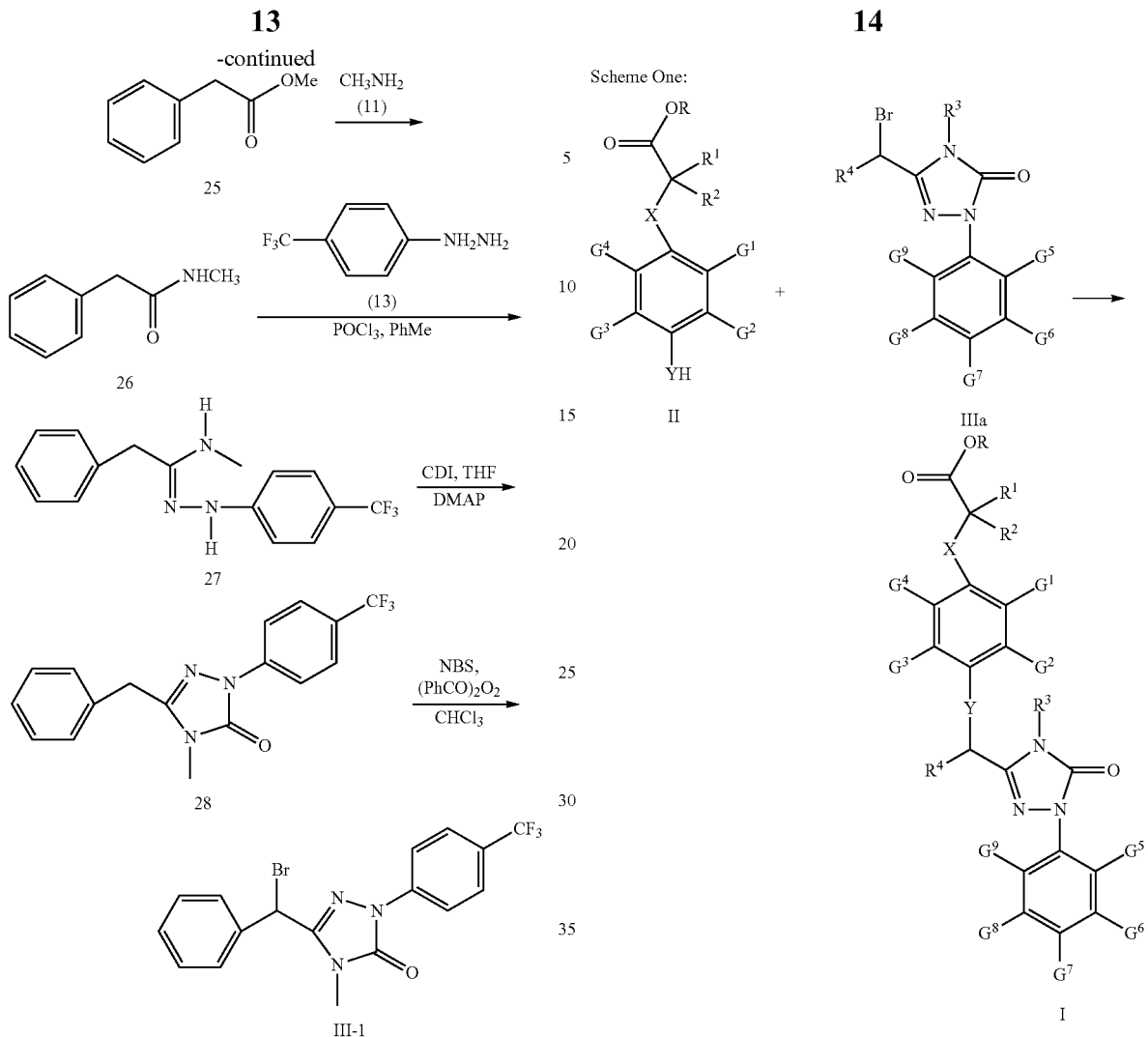

In the above scheme, comprised are following steps:

1) using methanol (MeOH) as the solvent and sulphuric acid as the catalyst, upon heating under reflux, the acid 24 undergoes esterification to generate the ester 25;

2) using methanol (MeOH) as the solvent, the ester 25 is aminated with the amine 11 at room temperature to generate the amide 26;

3) using toluene (PhCH$_3$) as the solvent, the amide 26 reacts with the p-trifluoromethyl phenylhydrazine13 under the action of phosphorus oxychloride (POCl$_3$) at 80° C. to generate the hydrazone 27;

4) using tetrahydrofuran (THF) as the solvent, the hydrazone 27 reacts with carbonyldiimidazole (CDI) at room temperature to generate the compound 28;

5) using chloroform as the solvent, N-bromosuccinimide (NBS) as the brominating reagent, and dibenzoyl peroxide as catalyst, upon heating under reflux, the compound 28 is brominated to generate the compound III-1.

Another object of the invention is to provide a process for preparation of the compound of formula (I).

The compound formula (I) of the invention is prepared by a process set forth in the following Scheme One or Scheme Two:

Wherein:

X, Y, R$^1$-R$^4$, G$^1$-G$^9$ are the same as given in definition of the compound of formula I, R is H or C1-C9 alkyl, preferably methyl or ethyl.

In Scheme One, the intermediate compounds II and III are subjected to coupling under the action of an alkali to generate the compound I (ester). The alkali is an organic or inorganic alkali, the inorganic alkali may include alkali metal carbonates, soluble alkaline earth metal carbonates, ammonium carbonate, etc., or any mixtures thereof; examples of the inorganic alkali include sodium carbonate, potassium carbonate, strontium carbonate, ammonium carbonate, etc., the organic alkali may be triethylamine and the like; preferably, the solvent is selected from acetonitrile, dimethylformamide (DMF), dimethyl sulfoxide (DMSO), tetrahydrofuran (THF), dioxane, etc., or any mixtures thereof. Preferably, the reaction temperature is at 0-100° C.; preferably at 40-80° C.; the reaction time is 1-12 hours, preferably 4-8 hours.

In the above processing scheme, the compound of formula II may be commercially available or synthesized by a typical method known from prior art documents (e.g., the method set forth in M. L. Sznaidman, Curt D. Haffner, Patric R. et al., *Bioorg. Med. Chem. Lett.* 2003, 13, 1517-1521; Zhi-liang wei et al., *J. Org. Chem.* 2003, 68, 9116-9118; *Org. Syn. Coll. Vol* 1, 102, 1941; *Org. Syn. Coll. Vol* 2, 290, 1943; Handbook of Fine Organic Chemical Raw Materials and Intermediate. XU Ke-xun (Eds), Scientific &Technological Industry Press, 3-426-3-584).

The compound of formula II comprises, but is not limited to the following compounds:

Ethyl 2-(2-methyl-4-hydroxy)-phenoxy-acetate (hereinafter known as "II-1");
Ethyl 2-(3-methyl-4-hydroxy)-phenoxy-acetate (hereinafter known as "II-2");
Ethyl 2-(2-ethyl-4-hydroxy)-phenoxy-acetate (hereinafter known as "II-3");
Ethyl 2-(3-methyl-4-hydroxy)-phenylthio-acetate (hereinafter known as "II-4");
Ethyl 2-(2-methyl-4-hydroxy)-phenylthio-acetate (hereinafter known as "II-5");
Ethyl 2-(2,5-dimethyl-4-hydroxy)-phenylthio-acetate (hereinafter known as "II-6").

any mixtures thereof may be used as the carbonate salt. Both the intermediate compounds IV and V are commercially available.

In Scheme Two, the compound I (ester) can be hydrolyzed under alkaline condition to yield the compound I (acid), if R is C1-C9 alkyl, the said alkaline condition can be formed with the following alkali, such as, an alkali metal hydroxide, including but not limited to sodium hydroxide, lithium hydroxide, potassium hydroxide, and the like, or any mixtures thereof; the solvent system used in hydrolysis is C1-C4 alcohol (e.g., methanol, ethanol, propanol, butanol, and the like)-water (alcohol: water=9-1:1 (vol/vol)), THF—water (THF:water=9-1:1 (vol/vol)), or alcohol-dichloromethane-water (alcohol:dichloromethane:water=9-1:9-1:1 (vol/vol)); the reaction temperature is at 0-80° C., preferably at 20-40° C.; the reaction time is 1-12 hours, preferably 2-4 hours.

Scheme Two:

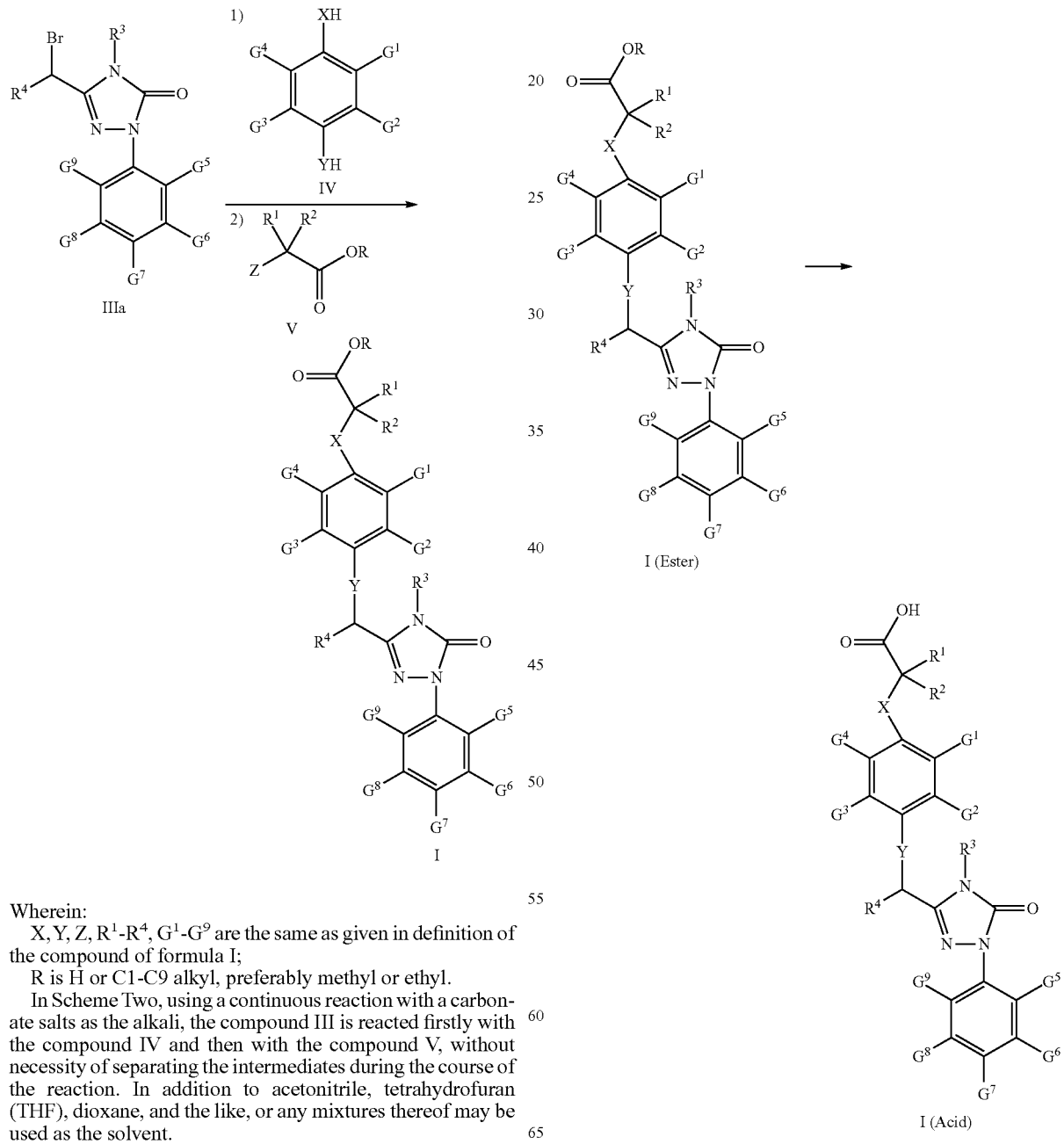

Wherein:
X, Y, Z, $R^1$-$R^4$, $G^1$-$G^9$ are the same as given in definition of the compound of formula I;
R is H or C1-C9 alkyl, preferably methyl or ethyl.

In Scheme Two, using a continuous reaction with a carbonate salts as the alkali, the compound III is reacted firstly with the compound IV and then with the compound V, without necessity of separating the intermediates during the course of the reaction. In addition to acetonitrile, tetrahydrofuran (THF), dioxane, and the like, or any mixtures thereof may be used as the solvent.

In addition to potassium carbonate, sodium carbonate, strontium carbonate, ammonium carbonate, and the like, or Wherein:

X, Y, Z, $R^1$-$R^4$, $G^1$-$G^9$ are the same as given in definition of the compound of formula I;

R is H or C1-C9 alkyl, preferably methyl or ethyl.

Another object of the invention is to provide a pharmaceutical composition containing the above-mentioned compound of formula (I) as active ingredients.

The pharmaceutical composition of the present invention containing the above-mentioned compound of formula (I) comprises the compound of formula (I) and conventional adjuvants used for a pharmaceutical formulation.

The conventional adjuvants used for such a pharmaceutical formulation refer to those which have been approved by the competent department for medicament administration and conform to the criteria for the pharmaceutical adjuvants. They have been classified into two groups on basis of their different functionalities: one group of adjuvants are necessary for the processing and manufacture of the pharmaceutical formulation, which include diluents, binders, glidants, suspending agents and lubricants, etc.; the other group of adjuvants function in promoting digestion and absorption of the medicament in vivo, which include disintegrants, cosolvents, etc. They are not active in vivo in human body, exerting neither therapeutic effect nor toxicity.

Among the above adjuvants, diluents may be selected from any one or any mixtures of any two or more of the following materials: starch, modified starch, sucrose, lactose monohydrate, anhydrous lactose, glucose, mannitol, and various microcrystalline celluloses.

Among the above adjuvants, binders may be selected from any one or a mixtures of any two or more of the following materials: hydroxypropyl methylcellulose, pregelatinized starch, polyvidone (polyvinylpyrrolidone), carboxymethylcellulose and derivates thereof, methylcellulose, ethylcellulose, starch, carbohydrates, and the like; preferably hydroxypropyl methylcellulose, pregelatinized starch, and polyvidone.

Among the above adjuvants, lubricants may be selected from any one or any mixtures of any two or more of the following materials: magnesium stearate, talc powder, and type I hydrogenated vegetable oils.

Among the above adjuvants, suspending agents may be selected from any one or a mixture of any two or more of the following materials: gelatin, pectin, gum arabic, sodium alginate, methylcellulose, ethylcellulose, hydroxypropyl cellulose, carboxymethyl cellulose, and methylcellulose.

Among the above adjuvants, disintegrants may be selected from any one or a mixture of any two or more of the following materials: starch, low-substituted hydroxypropyl cellulose, sodium carboxymethyl starch, calcium carboxymethyl cellulose, cross-linked polyvidone, cross-linked cellulose and cross-linked sodium carboxymethyl cellulose.

Among the above adjuvants, cosolvents may be selected from any one or a mixture of any two or more of the following materials: Span series, Tween series, polyethylene glycol series, soybean lecithin, and the like.

The above-described pharmaceutical composition may be in any forms of the following oral formulations: 1, plain-tablets; 2, film-coated tablets; 3, dragees; 4, enteric coated tablets; 5, dispersible tablets; 6, capsule; 7, granulas; 8, suspensions; and 9, solutions.

The above-described formulation forms can be prepared by conventional formulation process.

Another purpose of the invention is to provide use of the compound formula (I) in the manufacture of a medicament for treating or preventing a disease which could be treated or prevented by activating the peroxisome proliferator-activated receptor subtype δ (PPARδ) thereof. Said disease includes metabolic syndrome, obesity, dyslipidemia, pathoglycemia, insulin resistance, senile dementia or tumors, etc.

According to the invention, the use of the compound of formula (I) in the manufacture of a medicament for treating or preventing a disease which could be treated or prevented by activating the peroxisome proliferator-activated receptor subtype δ (PPARδ) thereof is provided, in which said disease is selected from one or more of metabolic syndrome, obesity, dyslipidemia, pathoglycemia, insulin resistance, senile dementia or tumors, etc.

According to the invention, a method of treating or preventing a disease which can be treated or prevented by activating the peroxisome proliferator activated receptor subtype δ (PPARδ) thereof is provided, in which the method comprises a step of administration of a therapeutically or prophylactically effective amount of the compound of formula (I) to a patient, and said disease is selected from one or more of metabolic syndrome, obesity, dyslipidemia, pathoglycemia, insulin resistance, senile dementia, or tumors, etc.

After reading the specification of the application, one skilled in the art may recognize other advantages and uses of the invention.

EMBODIMENTS

Figure 1:
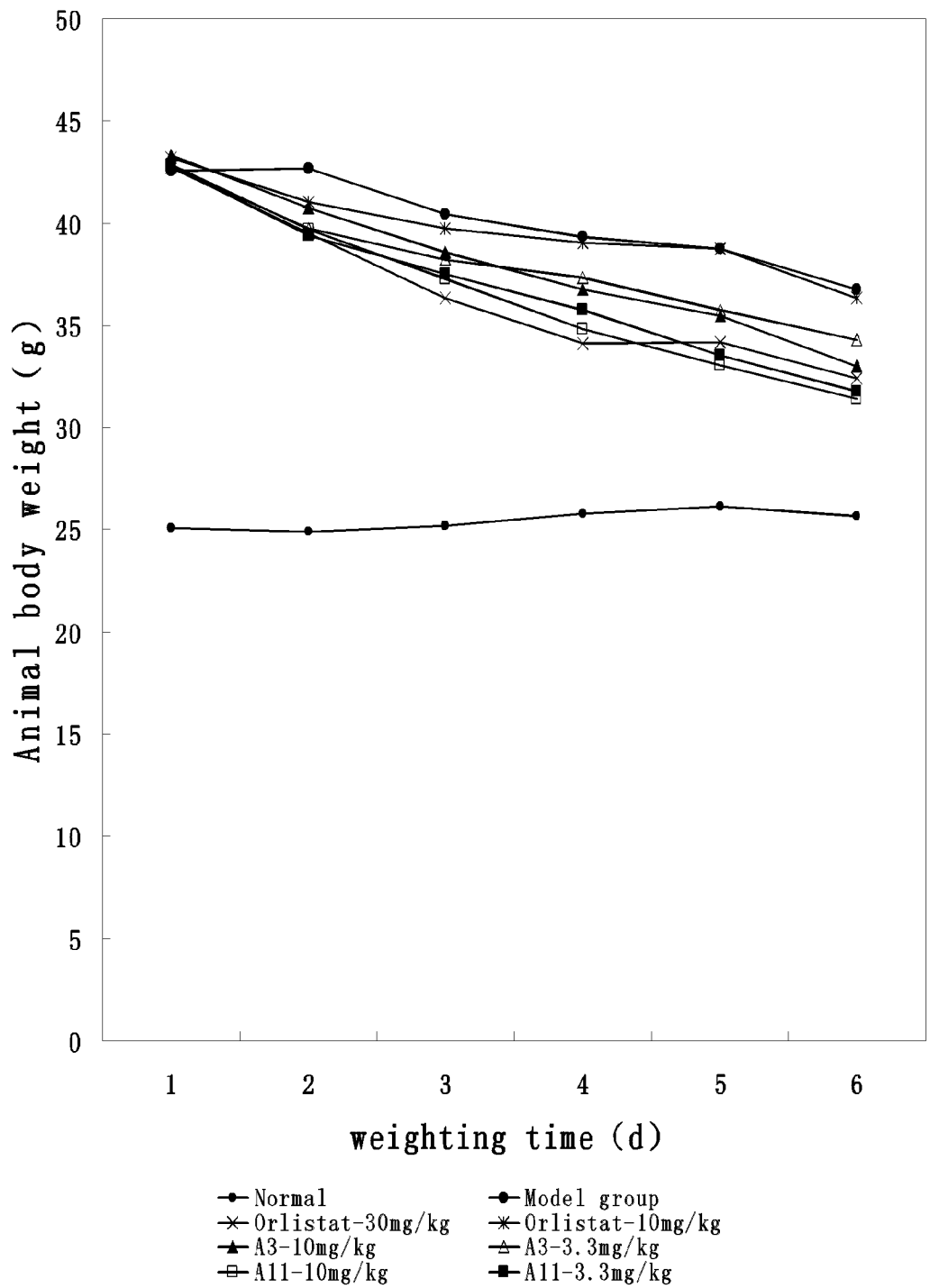
FIG. 1 represents a change curve of the animal body weight through time, which shows the medicament has effect on the animal body weight and food intake. The abscissa represents the weighting time (weighted every 2 days); the ordinate represents the body weight of the animal. The positive control is orlistat (two dose groups: 30 mg/kg and 10 mg/kg). In the present invention, the medicament formulations (A-3 and A-11) separate two dose groups (10 mg/kg and 3.3 mg/kg).

The present invention will be described in detail in reference to the specific examples below. It should be understood that in light of the disclosure herein, various modifications and improvements may be made by those skilled in the art to the present invention without departing from the spirit and scope of the present invention, all of which should be fallen within the claimed scope defined by the claims as appended. Furthermore, it should be understood that the examples provided herein is for the illustrative purpose only, and is not to be construed as a limitation to the present invention in any way.

In the present application, C1-C9 radical (alkyl, alkoxy, alkylthio, and the like) comprises C1-C2, C1-C3, C1-C4, C1-05, C1-C6, C1-C7, C1-C8, and C1-C9 radical (alkyl, alkoxy, alkylthio, and the like), etc.

Model for Medicament Screening
In Vitro Screening of a Nuclear Receptor Activating Agent
The Experimental Procedure in the Screening Model is as Follows:

1. Brief Description of a Nuclear Receptor-Associated Screening Model

Using a reporter gene protocol, the screening model for screening a nuclear receptor agonist in a living cell is designed on a basis of the principal that an activated nuclear receptor can activate transcription of its downstream gene. A reporter gene plasmid is constructed, in which the DNA binding sequence for the nuclear receptor (NRE) is inserted upstream of the luciferase gene, so that the expression of the luciferase gene is placed under the control of the nuclear receptor. Then, the reporter gene plasmid and the nuclear receptor are simultaneously transferred into a cell, and the nuclear receptor is activated when the nuclear receptor agonist is present in the cell culture medium. Then the activated receptor is able to induce the expression of the luciferase gene, while the amount of the luciferase can be determined through its luminous substrate. In this way, the intensity of activation by the compound on the nuclear receptor could be known by observing the luminescence intensity. For calibration of the testing error caused by factors such as the transfection efficiency, amount of the cells inoculated, toxicity of the compound, etc., the GFP plasmid was co-transfected simultaneously as an inner reference, and the luminescent values for all of testing wells are calibrated with GFP values when analyzing the experimental results. The experimental results are expressed as relative fold activation, with a value of 1 for the solvent control, and the greater the fold is, the higher the activation capacity represents.

2. Experiment Procedure

The detailed protocol of the experiment on the screening model may be referred to the following paper: "Design, synthesis and evaluation of a new class of noncyclic 1,3-dicarbonyl compounds as PPARα selective activators", Bioorg Med Chem. Lett. 2004; 14(13): 3507-11. The specific operation is described as follows:

The experiment reagents: the compounds to be tested (20 mM, in DMSO, stored at −80° C.).

(1) Day 1: The Cell Cultivation and Inoculating

The hepatocarcinoma cell HepG2 (from ATCC, American Type Culture Collection) was cultured in DMEM medium supplemented with 10% heat-inactivated fetal bovine serum (FBS, Invitogen, Grand Island, N.Y., USA) in a T-75 culture bottle (Greiner, Germany) in a incubator at 37° C., the relative humidity of 100%, and 5% $CO_2$. When the cell culture in the culture bottle reached 80-90% confluency, it was digested with 0.25% Trypsin (with EDTA) for 3 min and inoculated into a 96-well cell culture plate at an inoculating density of 2000 cells/100 µl/well.

(2) Day 2: The Cell Transfection

In the next day, when the cells in the 96-well culture plate grew up to 50-80% confluency, cell transfection was performed. The cell co-transfection system comprised the FuGene6 transfection agent (Roche Molecular Biochemicals, Indianapolis, Ind., U.S.A.) and 60 ng DNA (long of hRXR, 10 ng of pCMV βGal, 10 ng of the nuclear receptor expression plasmid RXR/PPARδ, 30 ng of GFP fluorescence reporter gene plasmid, respectively).

(3) The Medicament Treatment

The cell culture medium was discarded immediately at 24 hours post-transfection and replaced by 200 µl of a fresh DMEM medium containing the medicament to be tested (with 10% FBS treated by activated carbon). The final concentrations of the medicament to be tested were 10, 5, 1, 0.1, 0.01, 0.001, and 0 µM, and the positive control is 0.05 µM of 2-bromostearic acid (purchased from Sigma, USA) with DMSO in each well (the final concentration was 0.1%).

(4) The Kinase Activity Assay 24 h after treatment with the medicament, the cells were lysed with a lysis solution (Cell Culture Lysis buffer, Promega) and centrifuged, and the supernatant was collected. The supernatant was treated with a fluorescence detection kit (Promega) and counted by a fluorescence meter (Ascent Fluoroskan FL reader, Thermo Labsystems, Finland), and the relative intensity of the luciferase was determined. For assaying the β-galactosidase activity used in the experiment as the inner reference (the inner reference calibrating for the transfection efficiency), 50 µl of the supernatant was transferred into a fresh microplate and treated with the Promega kit and read at a wavelength of 405 nm from a microplate reader (Bio-tech Instruments Inc., Winooski, Vt., USA) (Sauerberg, P.; Olsen, G. S.; Jeppesen, L.; Mogensen, J. P. et al., *J. Med. Chem.*, 2007, 50, 1495-1503).

3. Analysis:

The median effective concentration ($EC_{50}$) of a sample is a concentration at which the sample has 50% pharmacological effect. This value is one of the important parameters for evaluating pharmacological effects of a compound. In the present screening process, the $EC_{50}$ of a sample was calculated according to the activation of the receptor by the sample at six different concentrations.

4. Screening Result

The compound of formula I was obtained, which could activate the PPARδ receptor.

The Activity Data of the Compound of Formula I (Acid) In Vitro

The activity of the compound of formula I (acid) in vitro was measured by the following processes: the sample [the compound of formula (I) (acid)] was dissolved and diluted into different concentrations, the activity of the sample for activating the PPARδ receptor was tested at the different concentrations, the correspondence of concentration vs effect was obtained, and then the corresponding value for the median effective concentration ($EC_{50}$) was calculated. The test results were shown in Table 1.

TABLE 1

Data on the activity of the compound of formula I (acid) in vitro

| The compound code | PPARδ $EC_{50}$ (nM) |
|---|---|
| A-1 | 468 |
| A-2 | 100 |
| A-3 | 10 |
| A-4 | 10 |
| A-5 | 340 |
| A-6 | 2090 |
| A-7 | 380 |
| A-8 | 3020 |
| A-9 | 6610 |
| A-10 | 100 |
| A-11 | <1 |
| A-12 | 650 |
| A-13 | 20 |
| A-14 | <1 |
| A-15 | 20 |
| A-16 | 1 |
| A-17 | <1 |
| A-18 | <1 |
| A-19 | <1 |

Note:
the lower the $EC_{50}$ (nM) value is, the higher the activity represents.

It may be seen from the data in Table 1 that all of the compounds in the present invention have an agonisting activity for PPARδ.

Screening for In Vivo Pharmacodynamic Activity of the Compound

1. Screening for the Activity of Controlling Blood Lipid

Assays on In Vivo Activity of Part of the Compounds of Formula I (Acid) According to the Present Invention:

Four compounds were selected out from A-1 to A-19 and subjected to an assay on their in vivo activity. The interference effects of the medicaments were observed with a SD rat, ApoE mice, *Mesocricetus auratus*, etc models of having a high-fat diet induced hyperlipidemia. The results were shown in Table 2.

TABLE 2

The activities data in vivo of the compounds of formula I (acid)

| Code | TC | TG | LDL | HDL |
|---|---|---|---|---|
| GW501516 | ↓22% | ↓53% | ↓40% | ↑23% |
| A-1 | ↓40% | ↓55% | ↓57% | ↑25% |
| A-3 | ↓65% | ↓51% | ↓40% | ↑43% |
| A-16 | ↓60% | ↓41% | ↓36% | ↑12% |
| A-11 | ↓58% | ↓58% | ↓28% | ↑46% |

Note:
↓ represents decrease and
↑ represents increase.

It can be seen from Table 2 that the four compounds that were selected and subjected to the in vivo activity assay can decrease cholesterol (TC), triglyceride (TG) and low density lipoprotein (LDL), also increase the high density lipoprotein (HDL), which showed that the inventive compounds possessed superior effect of blood-lipid regulation. At the same time, the four compounds also had similar pharmacological effects on SD rat and ApoE mouse models, and showed a better effect on blood-lipid regulation, compared with that of GW501516.

Especially, the compound A-3 can not only decrease the cholesterol (TC) level up to 40%, decrease triglyceride (TG) up to 65%, and decrease density lipoprotein (LDL) up to 51%, but also increase the level of high density lipoprotein (HDL) up to 43%.

Afterwards, efficacy of the medicament of the A-3 was confirmed in the *Macaca rhesus* model of hyperlipidemia. After three months of administration, blood samples were taken from the femoral vein for the determination of hematological indicators, and the determination of the insulin, apolipoprotein A-1 (apoA-1) and apolipoprotein B-100 (apoB-100) by ELISA. The results showed that, in comparison to the control group of hyperlipidemia model, the content of serum total cholesterol (TC) in the animal groups having been subjected to the administration of A-3 was decreased by 45%, the content of low density lipoprotein (LDLc) was decreased by 38%, and the content of high density lipoprotein (HDLc) was increased by 67%. Meanwhile, it was found through ELISA assay that the insulin concentration was significantly decreased; the concentration of apoA-1 was significantly increased, the concentration of apoB-100 was significantly decreased, and the ratio of apoA-1 to apoB-100 approached to that in normal animals, which was fully consistent with the results from the LDL and HDL in the hematological determination. The results above showed that after the animals which had suffered from hyperlipidemia were administrated with the medicament A-3, all of the indicators from the hematological assay and ELISA assay reversed significantly, which in turn demonstrated that the therapeutic effect of the medicament was much better than that of GW501516.

2. Screening for Pharmacological Activity of Weight Loss

Experiment Procedure 3 week-old male C57BL/6J mice were chosen as experiment animals, 15 of which were randomly selected to feed with a standard fodder, and the remains were allowed to feed with a high fat fodder, with each of the mice being marked by ear-cutting. The body weights and fodder intake of the mice were weighed every week. After feeding was continued for 15 weeks, the mice in the high fat fodder group had an average body weight of 42 g, the mice in the standard fodder group had an average body weight of 28 g. the mice both in the model group and in the dosing group were further to be fed with the high fat fodder. After the administration of the inventive compounds for four weeks, the effects of the medicaments on the levels of blood lipid and blood glucose, body weight, and fodder intake in the animals were observed, while a glucose tolerance test was performed to investigate the effects of the medicaments on the glucose tolerance in the animals.

(1) Effects of the Medicaments on the Levels of Blood Lipid and Blood Glucose in the Animals As shown in Table 3, A-3 and A-11 can significantly decrease the levels of TG and GLU in the sera from the model animals, showing an effect much better than that of Orlistat.

TABLE 3

Effects of the medicaments on levels of blood lipid and blood glucose in the animals ($\bar{x} \pm s$)

| group | n | Dosage (mg/kg) | 2 weeks administration | | | | 4 weeks administration | | | |
|---|---|---|---|---|---|---|---|---|---|---|
| | | | GLU | TC | TG | HDL | GLU | TC | TG | HDL |
| Normal | 5 | — | 3.61 ± 0.72 | 1.87 ± 0.35 | 0.17 ± 0.05 | 1.34 ± 0.2 | 2.9 ± 0.86 | 2.59 ± 0.35 | 0.21 ± 0.09 | 1.5 ± 0.64 |
| Model | 5 | — | 10.12 ± 0.89ΔΔΔ | 4.4 ± 0.48ΔΔΔ | 0.53 ± 0.14ΔΔΔ | 3.05 ± 0.31ΔΔΔ | 10.16 ± 0.77ΔΔΔ | 5.05 ± 0.43ΔΔΔ | 0.42 ± 0.13ΔΔΔ | 2.96 ± 0.46ΔΔΔ |
| Orlistat | 5 | 30 | 8.81 ± 2.16 | 3.89 ± 0.44 | 0.45 ± 0.09 | 2.72 ± 0.3 | 9.84 ± 1.83 | 3.48 ± 0.54** | 0.41 ± 0.04 | 2.79 ± 0.35 |
| Orlistat | 5 | 10 | 11.11 ± 1.08 | 3.81 ± 2.56* | 0.36 ± 0.09 | 3.29 ± 0.27 | 11.05 ± 1.09 | 4.24 ± 0.33** | 0.28 ± 0.03* | 2.63 ± 1.27 |
| A-3 | 5 | 10 | 6.54 ± 1.04*** | 5.12 ± 0.65 | 0.18 ± 0.02*** | 2.94 ± 1.42 | 6.6 ± 1.15*** | 4.75 ± 0.57 | 0.11 ± 0.07*** | 2.89 ± 0.28 |
| A-3 | 5 | 3.3 | 9.52 ± 1.71 | 3.25 ± 2.76 | 0.19 ± 0.12** | 3.31 ± 0.21 | 9.54 ± 0.71 | 5.11 ± 0.31 | 0.07 ± 0.01*** | 3.1 ± 0.59 |
| A-11 | 5 | 10 | 6.51 ± 1.61*** | 4.51 ± 0.37 | 0.16 ± 0.06*** | 2.39 ± 1.36 | 6.93 ± 0.3*** | 5.28 ± 0.48 | 0.15 ± 0.05** | 2.84 ± 1.09 |
| A-11 | 5 | 3.3 | 8.85 ± 2.13 | 534 ± 0.85 | 0.21 ± 0.08** | 3.25 ± 1.29 | 7.61 ± 0.5*** | 5.84 ± 0.21 | 0.12 ± 0.05*** | 3.83 ± 0.1** |

ΔΔΔ $P < 0.001$ in comparison with normal group;
*$P < 0.05$,
**$P < 0.01$,
***$P < 0.001$ in comparison with model groups (2) Effect of the Medicaments on the Body Weight and Food Intake in the Animals As shown in Table 4 and FIG. 1, A-3 and A-11 can significantly decrease the body weight of the animals, and have no significant effect on the food intake of the animals, indicating the superior weight-loss function of the medicaments.

TABLE 4

Effect of the medicaments on the food intake in the animal

| group | Food intake (g) | | | | |
|---|---|---|---|---|---|
| | 1 | 2 | 3 | 4 | 5 |
| Normal | 7.8 | 8.3 | 8.58 | 7.98 | 12.78 |
| Model | 13.34 | 5.94 | 6.64 | 7.2 | 7.12 |
| Orlistat - 30 mg/kg | 6.04 | 4.66 | 5.52 | 7.78 | 7.92 |
| Orlistat - 10 mg/kg | 5.88 | 5.42 | 6.7 | 6.64 | 6.4 |
| A-3 - 10 mg/kg | 5.46 | 4.84 | 4.94 | 5.28 | 6.9 |
| A-3 - 3.3 mg/kg | 5.22 | 5.04 | 6.06 | 5.1 | 6.275 |
| A-11 - 10 mg/kg | 7.2 | 5.2 | 6.0 | 6.4 | 6.9 |
| A-11 - 3.3 mg/kg | 6.0 | 5.0 | 5.8 | 6.2 | 6.9 |

(3) Oral Glucose Tolerance Test

Figure 2:
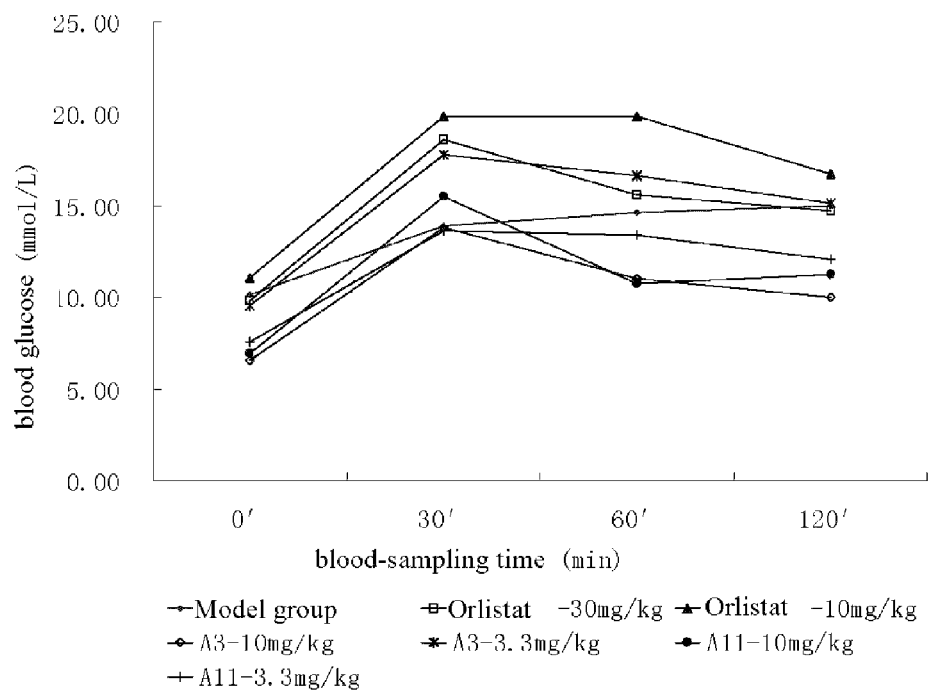
FIG. 2 represents a change curve of the blood glucose in animals, which demonstrates the results from the oral glucose tolerance test. The abscissa represents blood-sampling time points, 0 min, 30 min, 60 min, 120 min after orally given with glucose; the ordinate represents the corresponding blood glucose level (mmol/L).

The results were shown in FIG. 2, i.e., the original level of the blood glucose cannot be restored within 2 hours in the obese animal model, the glucose tolerance curve is abnormal, and the glucose tolerance decreased, while A-3 and A-11 can significantly improve the glucose tolerance in the obese animals.

3. Pharmacokinetic Investigation

1) Plasma Concentration-Time Curve

Experimental Procedure:

36 of SD rats were selected with a female-to-male ratio of 1:1 and a body weight in the range of 150-170 g, assigned them into two dosage groups, and they were administrated with A-1 and A-3, respectively; while 3 dosage subgroups were designed in each dosage group with the dose concentrations being 50, 10, and 2 mg/kg, six animals each subgroup with the female-to-male ratio of 1:1. All of the rats were fasting over 12 h and given ad libitum access to water. The dosing volume was 10 ml/kg, and blood samples of 0.4-0.5 ml were taken from the vena orbitalis posterior of the waken animals at different time points post-gastric lavage and centrifuged at 5000 rpm for 10 min. 200 μL of plasma sample was precisely measured, then supplemented with 200 μL acetonitrile, vortexed to evenness, left stand for 5 min, and centrifuged (14000 rpm, 5 min). The supernatant was collected and then centrifuged again (14000 rpm, 5 min). The resulting supernatant was gathered and subjected to HPLC injection. Time points for blood sampling were respectively: 0, 0.5, 1, 2, 4, 6, 8, 10, 12, 24, 36, 48 and 72 h, and the peak area for each time point was the average of those obtained from 6 rats at the same time point. Plasma concentrations were calculated and the medicament concentration-time curve was plotted.

Figure 3:
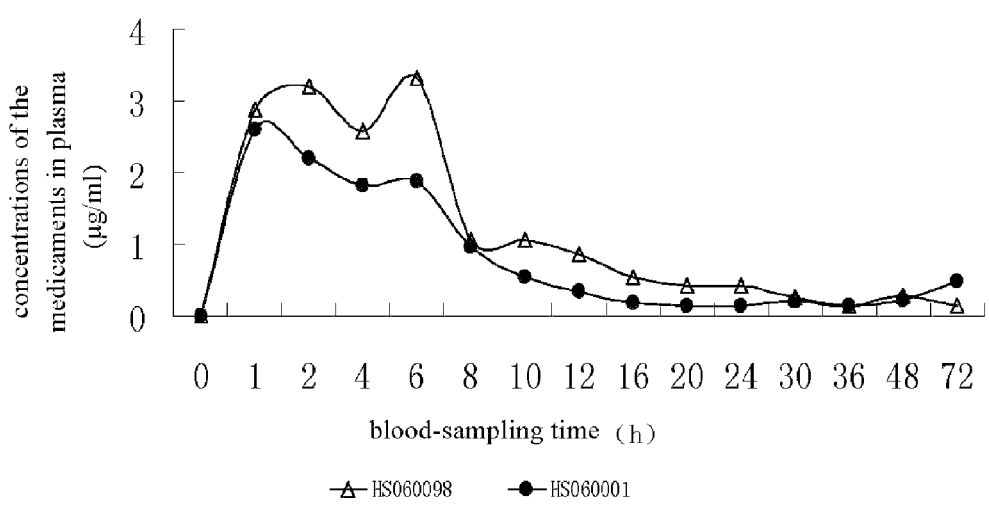
FIG. 3 represents the medicament-time curve of A-3 (HS060098) and A-1 (HS060001) in present invention. The abscissa represents the time points (h) of blood sampling; the ordinate represents the concentrations (μg/ml) of the medicaments in plasma from animals at different time.

The result was shown in FIG. 3.

The result indicates that the $t_{1/2}$ of A-3 is 10-12 h, the $t_{1/2}$ of A-1 is 26-28 h, the bioavailability of A-3 is 86%, and the bioavailability of A-1 is 15%.

2) Tissue Distribution 18 of SD rats were fasting for 16 h with free access for water, assigned them into 3 groups with 6 animals/group with a female-to-male ratio of 1:1; they were dosed with HS060098 (10 mg/kg), then the animals were sacrificed at 1, 10, and 24 h after dosing, and the heart, liver, spleen, lung, kidney in each animal were removed rapidly. The tainted blood on the surface of the organ was washed off immediately with physiological saline. The tissue from the organ was dissected apart, washed thoroughly, blotted off, weighed, supplemented with physiological saline at 400 mg/ml, homogenized in an ice bath for 1 min, and centrifuged at 3750 rpm for 20 min. 400 μl of the supernatant was pipetted precisely, followed by addition of 40 μl of an inner standard (HS060001 used as the inner standard with a molar concentration of 5 mmol/L), diluted with 3 ml of purified water, vortexed to homogeneity, and loaded onto a column (SPE C18 column was firstly washed with 3 ml of purified water, and sequentially with 3 ml of 10% methanol for activation). The column was rinsed with 3 ml of purified water at 1 ml/min, and then eluted with 3 ml of a elutant (methanol: purified water=9:1). The eluate was collected and blow-dried under a nitrogen flow at 45° C. The residue was dissolved in 400 μl of acetonitrile and then a HPLC insert was placed and followed by injection of the sample.

The results are shown in Table 5. The results indicate that A-3 and A-1 distribute mainly in liver, and A-3 distributes with relative homogeneity.

TABLE 5

The main distribution of A-3 and A-1 in organs

| Medicament | Liver (%) | Heart (%) | Spleen (%) | Lung (%) | Kidney (%) |
|---|---|---|---|---|---|
| A-3 | 36 | 26 | 13 | 16 | 9 |
| A-1 | 65 | 6 | 9 | 11 | 9 |

EXAMPLE

Preparation of the Intermediate Compound II

Example 1

Preparation of the Compound II-1

Preparation of Ethyl 2-(2-methyl-4-hydroxy)-phenoxy-acetate (II-1)

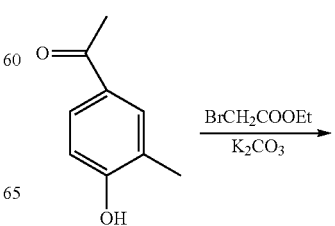

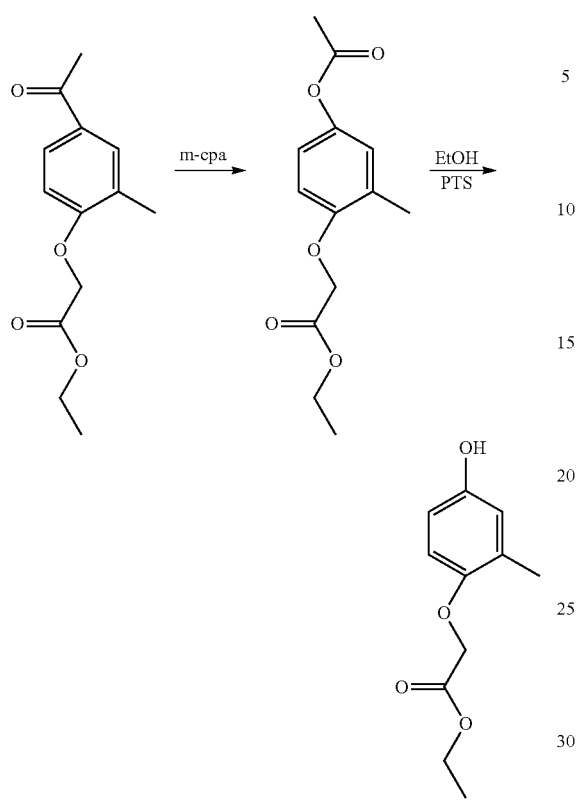

To a 500 ml single-necked flask were added sequentially with agitation 3-methyl-4-hydroxyacetophenone (25 g, 166.5 mmol), 250 ml of acetonitrile, and potassium carbonate ($K_2CO_3$, 26 g, 188.2 mmol). Then ethylbromoacetate (20 ml, 172.2 mmol) in acetonitrile (50 ml) was added dropwise thereinto. The reaction was stirred at room temperature for 8 hours. After the reaction was completed, the reaction mixture was diluted with ethyl acetate (200 ml), filtrated, and evaporated to give yellow oil.

In another 500 ml single-necked flask, to a stirred solution of above yellow oil in dichloromethane ($CH_2Cl_2$, 300 ml) were added 3-chloroperbenzoic acid (46 g, 199.9 mmol) and a catalytic amount of 4-methylbenzenesulfonic acid. The resulting mixture was stirred overnight at room temperature. After the reaction was completed, the reaction mixture was filtrated, and the resulting filter cake was washed with 100 ml of dichloromethane. The combined filtrate was washed with a saturated aqueous solution of sodium hyposulfite ($Na_2S_2SO_4$) and of sodium bicarbonate ($NaHCO_3$), and then evaporated to give pale yellow oil.

The crude product obtained from the above-described reaction was transferred into another 500 ml single-necked flask, and 80 ml of ethanol and a catalytic amount of 4-methylbenzenesulfonic acid were added thereinto. The reaction solution was heated to reflux for 6 h and then evaporated in vacuo to give a pale-yellow solid. The pale-yellow solid was recrystallized through petroleum ether/ethyl acetate (2:1 v/v) to give ethyl 2-(2-methyl-4-hydroxy)-phenoxy-acetate (16 g, 45.8% for three-steps) as white solid.

Its structure was characterized by the following data from nuclear magnetic resonance spectroscopy:

$^1$H NMR (400 MHz, $CDCl_3$) δ 1.34 (t, J=7.14 Hz, 3H), 2.27 (s, 3H), 4.30 (q, J=7.14 Hz, 2H), 4.61 (s, 2H), 6.61-6.63 (m, 1H), 6.65 (s, 1H), 6.67-6.68 (m, 1H), 7.31 (s, 1H).

Example 2

Preparation of the Compound II-2

Using 3-methyl-4-hydroxyacetophenone as a starting material, ethyl 2-(3-methyl-4-hydroxy)-phenoxy-acetate (II-2) was prepared according to a process similar to that described in Example 1, as a white solid with a yield of 40.2%.

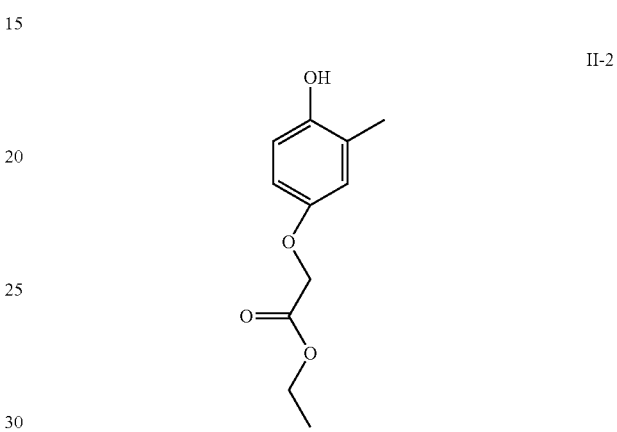

Its structure was characterized by the following data from nuclear magnetic resonance spectroscopy:

$^1$H NMR (400 MHz, DMSO) δ 1.23 (t, J=7.12 Hz, 3H), 2.29 (s, 3H), 4.18 (q, J=7.14 Hz, 2H), 4.64 (s, 2H), 6.57-6.60 (m, 1H), 6.68 (s, 1H), 6.69-6.70 (m, 1H), 8.87 (s, 1H); $^{13}$C NMR (100 MHz, DMSO) δ 14.5, 16.6, 60.9, 65.9, 112.2, 112.8, 115.4, 117.6, 125.2, 150.2, 150.8, 169.6.

Example 3

Preparation of the Compound II-3

Using 3-ethyl-4-hydroxyacetophenone as a starting material, ethyl 2-(2-ethyl-4-hydroxy)-phenoxy-acetate (II-3) was prepared according to a process similar to that described in Example 1, as a pale-yellow solid with a yield of 74.5%.

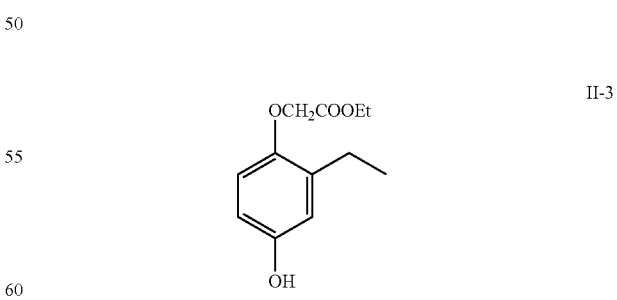

Its structure was characterized by the following data from nuclear magnetic resonance spectroscopy:

$^1$H NMR (400 MHz, $CDCl_3$) δ 1.23 (t J=7.53 Hz, 3H), 1.34 (t J=7.12 Hz, 3H), 2.69 (q, J=7.52 Hz, 2H), 4.30 (q, J=7.14 Hz, 2H), 4.61 (s, 2H), 5.35 (s, 1H), 6.6 (dd, J=8.65 Hz, 2.84 HZ, 1H), 6.65 (d, J=8.63 Hz, 1H), 6.72 (d, J=2.84 Hz, 1H);

$^{13}$C NMR (100 MHz, CDCl$_3$) δ 14.0, 14.1, 23.1, 61.3, 66.7, 112.6, 113.1, 116.5, 134.9, 149.9, 150.4, 169.8.

Example 4

Preparation of the Compound II-4

Preparation of Ethyl 2-(3-methyl-4-hydroxy)-phenylthio-acetate (II-4)

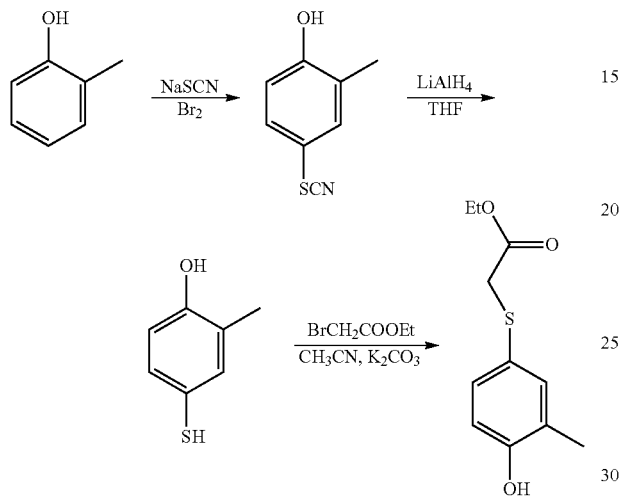

To a 500 ml three-necked flask were added sequentially with agitation o-cresol (15 g, 138.7 mmol), sodium thiocyanate (NaSCN, 34 g, 419.3 mmol), sodium bromide (NaBr, 16 g, 155.5 mmol) and methanol (200 ml). The mixture was cooled to 0° C., and then a solution of bromine (8.6 ml, 167 mmol) in methanol (30 ml) was added dropwise thereinto. After 1 hour of stirring at 0° C., the mixture was warmed up to room temperature and then stirred for another 4 hours at room temperature. After the reaction was completed, a 200 ml saturated aqueous solution of sodium bicarbonate (NaHCO$_3$) was added to the reaction mixture and stirred for 10 min. The mixture was extracted with ethyl acetate (2×500 ml). The combined organic layer was dried over anhydrous magnesium sulfate, filtrated, concentrated under reduced pressure to give yellow oil. Silica gel column chromatography purification (silica-gel H: 300-400 mesh; petroleum ether/ethyl acetate=8:1 v/v) was performed to yield 3-methyl-4-hydroxy-phenyl thiocyanic acid as a white solid (16 g, yield: 69.8%).

Its structure was characterized by the following data from nuclear magnetic resonance spectroscopy:

$^1$H NMR (400 MHz, DMSO) δ 2.17 (s, 3H), 6.92 (d, J=8.4 Hz, 1H), 7.37 (dd, J=8.4 Hz, 2.48 HZ, 1H), 7.44 (d, J=2.48 HZ, 1H), 10.1 (s, 1H); $^{13}$C NMR (100 MHz, DMSO) δ 16.2, 111.1, 113.1, 116.8, 127.3, 132.2, 135.4, 158.3.

In a 500 ml three-necked flask, to a stirred mixture of lithium aluminum tetrahydride (LiAlH$_4$, 3.5 g, 92.2 mmol) and tetrahydrofuran (THF, 50 ml) was added dropwise a solution of 3-methyl-4-hydroxy-phenyl thiocyanic acid (6.13 g, 37.1 mmol) in tetrahydrofuran (THF, 30 ml) at 0° C. After 30 min of stirring at 0° C., the mixture was warmed up to room temperature and then stirred for 1 hour at room temperature. The reaction was quenched by adding ethanol (10 ml), The value of pH of the mixture was adjusted to 3-4 by adding 6 M hydrochloric acid in an ice water bath. Then the aqueous layer was extracted with ethyl acetate (3×100 ml). The combined organic layer was dried over anhydrous magnesium sulfate, filtrated, and evaporated in vacuo to give a crude product 4-hydroxy-3-methyl thiophenol as yellow oil.

In a 250 ml single-necked flask, to a solution of above crude product of 4-hydroxy-3-methyl thiophenol in acetonitrile (80 ml) was added with agitation ethyl 2-bromoacetate (4.3 ml, 37 mmol), followed by adding potassium carbonate (5.1 g, 36.9 mmol). The resulting mixture was stirred for 8 hours at room temperature. After the reaction was completed, the reaction mixture was diluted with ethyl acetate (80 ml), filtrated, and evaporated to give a residue. The residue was purified by silica gel column chromatography (silica-gel H:300-400 mesh; petroleum ether/ethyl acetate=8:1 v/v) to yield 6.38 g of ethyl 2-(3-methyl-4-hydroxy)-phenylthio-acetate as yellow oil (yield: 76%).

Its structure was characterized by the following data from nuclear magnetic resonance spectroscopy:

$^1$H NMR (400 MHz, CDCl$_3$) δ 1.24 (t J=7.2 Hz, 3H), 2.18 (s, 3H), 3.49 (s, 2H), 4.15 (q, J=7.14 Hz, 2H), 5.74 (s, 1H), 6.63 (d, J=8.27 Hz, 1H), 7.17 (dd, J=8.16 Hz, 2.28 HZ, 1H), 7.25 (d, J=2.28 Hz, 1H); $^{13}$C NMR (100 MHz, CDCl$_3$) δ 14.1, 15.7, 38.8, 61.6, 115.6, 124.1, 125.1, 131.9, 135.7, 154.5, 170.6.

Example 5

Preparation of the Compound II-5

Using m-cresol as a starting material, ethyl 2-(2-methyl-4-hydroxy)-phenylthio-acetate (II-5) was prepared according to a process similar to that described in Example 4, as yellow oil with a yield of 63%.

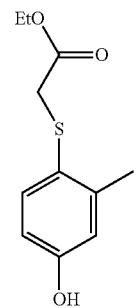

II-5

Its structure was characterized by the following data from nuclear magnetic resonance spectroscopy:

$^1$H NMR (400 MHz, CDCl$_3$) δ 1.23 (t J=7.1 Hz, 3H), 2.39 (s, 3H), 3.44 (s, 2H), 4.14 (q, J=7.11 Hz, 2H), 6.38 (s, 1H), 6.54 (dd, J=8.36 Hz, 2.72 HZ, 1H), 6.64 (d, J=2.71 Hz, 1H), 7.31 (d, J=8.37 Hz, 1H).

Example 6

Preparation of the Compound II-6

Using 2,5-dimethyl phenol as a starting material, ethyl 2-(2,5-dimethyl-4-hydroxy)-phenylthio-acetate (II-6) was prepared according to a process similar to that described in Example 4, as a white solid with a yield of 72%.

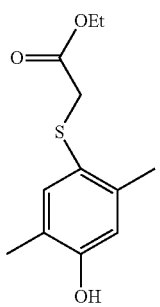

II-6

Its structure was characterized by the following data from nuclear magnetic resonance spectroscopy:

$^1$H NMR (400 MHz, CDCl$_3$) δ 1.23 (t J=7.16 Hz, 3H), 2.16 (s, 3H), 2.38 (s, 3H), 3.43 (s, 2H), 4.13 (q, J=7.13 Hz, 2H), 5.19 (s, 1H), 6.58 (s, 1H), 7.23 (s, 1H); $^{13}$C NMR (100 MHz, CDCl$_3$) δ 14.1, 15.1, 20.2, 37.9, 61.4, 116.9, 122.1, 123.3, 136.9, 140.0, 154.3, 170.3.

Preparation of the Intermediate Compound III

Example 7

Preparation of the Compound III-1

Preparation of 3-(1'-bromo-benzyl)-4-methyl-1-(4-trifluoromethyl)phenyl-1H-1,2,4-triazole-5(4H)-one (compound III-1) can be made according to the following reaction scheme:

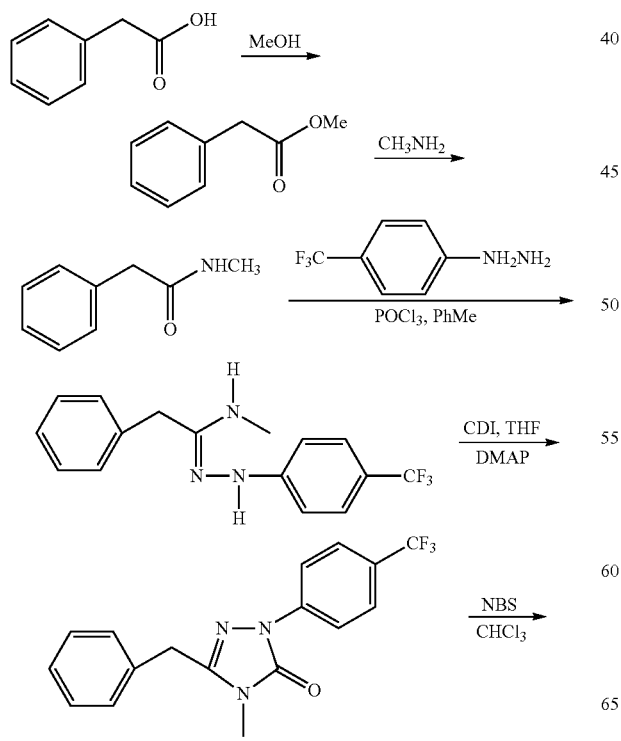

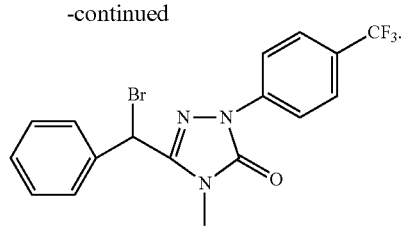

Preparation of N-methyl Phenylacetamide

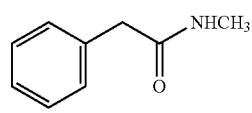 [SMILES: CNC(=O)Cc1ccccc1]

Phenylacetic acid (10 g, 73.5 mmol) and methanol (60 ml) were added to a 250 ml three-necked flask, followed by addition of 10 drops concentrated sulphuric acid. The resulting solution was heated to reflux for 2 hours. Then, the solution was cooled to room temperature, followed by adding 25-30% aqueous solution of methylamine (50 ml, approximately 403 mmol), and heated to reflux for another 3 hours. After the reaction was completed, it was cooled to room temperature. Most of the solvent was removed by rotary vacuum evaporation, 30 ml of water was added thereinto, and then the mixture was extracted with ethyl acetate (3×80 ml). The combined organic layer was dried over anhydrous magnesium sulfate, filtrated, and concentrated under reduced pressure to yield 10.1 g of N-methyl phenylacetamide (white solid, yield: 91.8%).

Its structure was characterized by the following data from nuclear magnetic resonance spectroscopy:

$^1$H NMR (400 MHz, CDCl$_3$) δ 2.69 (d, J=4.84 Hz, 3H), 3.51 (s, 3H), 5.95 (wide, 1H), 7.21-7.24 (m, 3H), 7.28-7.32 (m, 3H); $^{13}$C NMR (100 MHz, CDCl$_3$) δ 26.4, 43.6, 127.2, 128.9, 129.4, 135.1, 171.8.

Preparation of 3-benzyl-4-methyl-1-(4-trifluoromethyl)phenyl-1H-1,2,4-triazole-5(4H)-one

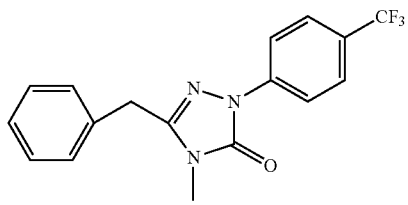 [SMILES: Cn1c(Cc2ccccc2)nn(-c2ccc(C(F)(F)F)cc2)c1=O]

In a 1000 ml three-necked flask, to a stirred solution of N-methyl phenylacetamide (25 g, 167.7 mmol) and (4-trifluoromethyl)phenylhydrazine (30 g, 170 mmol) in toluene (250 ml) at 80-90° C. was added dropwise a solution of phosphorus oxychloride (POCl$_3$, 15 ml, 180 mmol) in toluene (50 ml). After the addition was completed, the mixture was stirred for 5 hours at 80-90° C., then cooled to room temperature when the reaction was completed, and filtrated. The residual filter cake was washed with ethyl acetate until it became yellowish-brown. The filtrate was washed with a saturated aqueous solution of sodium bicarbonate, dried over anhydrous magnesium sulfate, filtrated, concentrated under reduced pressure, and re-filtrated. The filter cake was washed with ethyl acetate. The filter cakes were combined and vacuum-dried. Finally 43.5 g of N-methyl-2-phenyl-N-(4-trifluoromethyl)phenylacetamide hydrazone was obtained (yellowish-brown solid, yield: 84.4%).

In a 1000 ml three-necked flask, to a stirred mixture of N-methyl-2-phenyl-N-(4-trifluoromethyl)phenylacetamide hydrazone (58.6 g, 190.9 mmol) and N,N-dimethylamino pyridine (DMAP, 0.5 g, 4.0 mmol) in tetrahydrofuran (THF, 500 ml) was slowly added carbonyldiimidazole (CDI, 46.43 g, 286.4 mmol). The resulting mixture was stirred at room temperature for 12 hours. After the reaction was completed, the mixture was poured into a 2000 ml beaker containing 300 ml of water, adjusted to pH 2-4 with 6 N hydrochloric acid under agitation, and filtrated. The filter cake was washed with distilled water and then vacuum-dried to yield 56.7 g of 3-benzyl-4-methyl-1-(4-trifluoromethyl)-phenyl-1H-1,2,4-triazole-5(4H)-one (pale-yellow solid, yield: 89.2%).

Its structure was characterized by the following data from nuclear magnetic resonance spectroscopy:

$^1$H NMR (400 MHz, CDCl$_3$) δ 3.11 (s, 3H), 4.0 (s, 2H), 7.25-7.38 (m, 5H), 7.67 (d, J=8.68 Hz, 2H), 8.18 (d, J=8.68 Hz, 2H); $^{13}$C NMR (100 MHz, CDCl$_3$) δ 27.6, 32.7, 118.0, 122.8, 125.5, 126.6, 127.7, 128.4, 129.1, 133.6, 140.7, 146.8, 152.6.

Preparation of 3-(1-bromo-benzyl)-4-methyl-1-(4-trifluoromethyl)phenyl-1H-1,2,4-triazole-5(4H)-one (III-1)

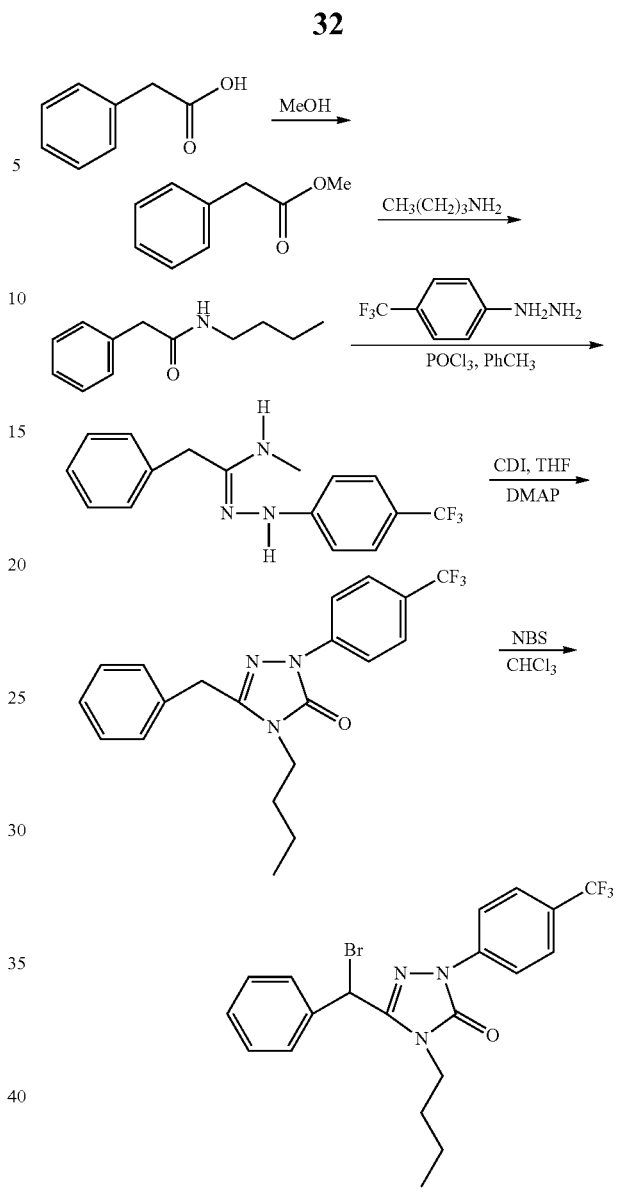

To a 500 ml three-necked flask, 3-benzyl-4-methyl-1-(4-trifluoromethyl)phenyl-1H-1,2,4-triazole-5(4H)-one (15 g, 45 mmol) and chloroform (CHCl$_3$, 250 ml) were added with agitation. To the stirred solution were added N-bromosuccinimide (NBS, 12 g, 68 mmol) and benzoyl peroxide (0.5 g, 2.25 mmol). The mixture was heated cautiously to reflux for 12 hours. After the reaction was completed, the mixture was filtrated. The filtrate was concentrated under reduced pressure to give a residue which was purified by flash silica gel column chromatography (silica-gel H:300-400 mesh; petroleum ether/ethyl acetate=8:1 v/v) to yield 14.6 g of 3-(1'-bromo-benzyl)-4-methyl-1-(4-trifluoromethyl)phenyl-1H-1,2,4-triazole-5(4H)-one as reddish-brown oil (yield: 79.7%).

Its structure was characterized by the following data from nuclear magnetic resonance spectroscopy:

$^1$H NMR (400 MHz, CDCl$_3$) δ 3.28 (s, 3H), 6.07 (s, 1H), 7.25-7.58 (m, 5H), 7.66 (d, J=8.68 Hz, 2H), 8.13 (d, J=8.68 Hz, 2H); $^{13}$C NMR (100 MHz, CDCl$_3$) δ 28.4, 42.1, 69.6, 118.3, 126.2, 126.8, 127.3, 129.1, 129.9 133.9, 140.3, 145.7, 152.4.

Example 8

Preparation of the compound III-2

Preparation of 3-(1'-bromo-benzyl)-4-n-butyl-1-(4-trifluoromethyl)phenyl-1H-1,2,4-triazole-5(4H)-one (compound III-2) can be conducted according to the following reaction scheme:

Preparation of N-n-butylphenylacetamide

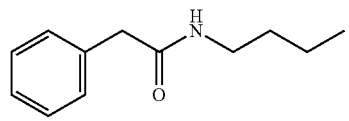

Phenylacetic acid (16 g, 117.6 mmol) and methanol (60 ml) were added to a 250 ml three-necked flask, followed by addition of 5 drops of concentrated sulphuric acid. The resulting solution was heated to reflux for 6 hours. Then, the mixture was cooled to room temperature, followed by adding n-butylamine (12 ml, 121.4 mmol), and heated to reflux for another 3 hours. After the reaction was completed, it was cooled to room temperature. Most of the solvent was removed by rotary vacuum evaporation, 30 ml of water was added thereinto, and the mixture was extracted with ethyl acetate (3×80 ml). The combined organic layer was dried over anhydrous magnesium sulfate, filtrated, and concentrated under reduced pressure to yield 15.9 g of N-n-butylphenylacetamide (white solid, yield: 70.4%).

Its structure was characterized by the following data from nuclear magnetic resonance spectroscopy:

$^1$H NMR (400 MHz, CDCl$_3$) δ 0.86 (t, J=7.28 Hz, 3H), 1.21-1.29 (m, 2H), 1.36-1.44 (m, 2H), 3.2 (q, J=7.04 Hz, 2H), 5.62 (wide, 1H), 7.24-7.29 (m, 3H), 7.32-7.36 (m, 2H); $^{13}$C NMR (100 MHz, CDCl$_3$) δ 13.7, 19.9, 31.5, 39.4, 43.8, 127.2, 128.9, 129.4, 135.1, 170.9.

Preparation of 3-benzyl-4-n-butyl-1-(4-trifluoromethyl)phenyl-1H-1,2,4-triazole-5(4H)-one

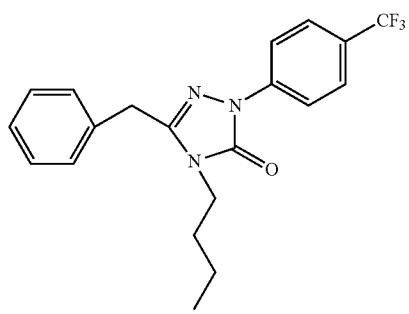 [SMILES: CCCCn1c(Cc2ccccc2)nn(-c2ccc(C(F)(F)F)cc2)c1=O]

In a 500 ml three-necked flask, to a stirred solution of N-n-butylphenylacetamide (11 g, 57.5 mmol) in toluene (150 ml) at 80-90° C. was added dropwise a solution of phosphorus oxychloride (POCl$_3$, 17 ml, 75.1 mmol) in toluene (20 ml). After the addition was completed, the mixture was stirred for 5 hours at 80-90° C., and then allowed to cool to room temperature after the reaction was completed, and filtrated. The filter cake was washed with ethyl acetate until it became yellowish-brown. The filtrate was washed with a saturated aqueous solution of sodium bicarbonate, dried over anhydrous magnesium sulfate, filtrated, concentrated under reduced pressure, and filtrated again. The filter cake was washed again with ethyl acetate. The filter cakes were combined and vacuum-dried. Finally, 15.7 g of N-n-butyl-2-phenyl-N-(4-trifluoromethyl)phenylacetamide hydrazone was obtained (yellowish-brown solid).

In a 500 ml three-necked flask, to a stirred mixture of N-n-butyl-2-phenyl-N-(4-trifluoromethyl)phenylacetamide hydrazone (15.7 g) and N,N-dimethylamino pyridine (DMAP, 0.5 g, 4.0 mmol) in tetrahydrofuran (THF, 250 ml) was slowly added carbonyldiimidazole (CD, 7.43 g, 45.8 mmol) at room temperature. The reaction mixture was stirred at room temperature for 12 hours. After the reaction was completed, the mixture was poured into a 500 ml beaker containing 100 ml of water, adjusted to pH 2-4 with 6 N hydrochloric acid under agitation, and filtrated. The filter cake was washed with distilled water and then vacuum-dried to yield 6.28 g of 3-benzyl-4-n-butyl-1-(4-trifluoromethyl)phenyl-1H-1,2,4-triazole-5(4H)-one (pale-yellow solid, two-steps yield: 29.2%).

Its structure was characterized by the following data from nuclear magnetic resonance spectroscopy and Mass spectroscopy:

$^1$H NMR (400 MHz, CDCl$_3$) δ 0.86 (t, J=7.3 Hz, 3H), 1.22-1.29 (m, 2H), 1.37-1.44 (m, 2H), 3.49 (q, J=7.6 Hz, 2H), 4.0 (s, 2H), 7.26-7.38 (m, 5H), 7.67 (d, J=8.70 Hz, 2H), 8.19 (d, J=8.65 Hz, 2H); $^{13}$C NMR (100 MHz, CDCl$_3$) δ 13.5, 19.8, 30.6, 32.8, 41.7, 117.9, 126.1, 126.9, 127.2, 127.8, 128.6, 129.1, 134.0, 140.7, 146.6, 152.5; MS (ESI) m/z 376.29 (M+1)$^+$.

Preparation of 3-(1'-bromo-benzyl)-4-n-butyl-1-(4-trifluoromethyl)phenyl-1H-1,2,4-triazole-5(4H)-one (III-2)

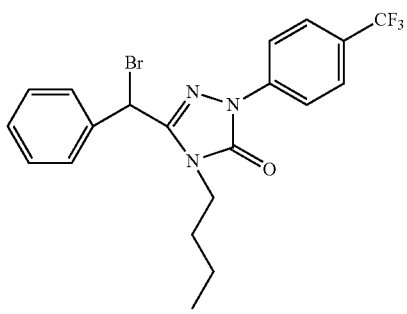 [SMILES: CCCCn1c(C(Br)c2ccccc2)nn(-c2ccc(C(F)(F)F)cc2)c1=O]

To a 250 ml three-necked flask, 3-benzyl-4-n-butyl-1-(4-trifluoromethyl)phenyl-1H-1,2,4-triazole-5(4H)-one (3.75 g, 10 mmol) and chloroform (100 ml) were added. To the stirred solution were added N-bromosuccinimide (NBS, 3.56 g, 20 mmol) and benzoyl peroxide (0.4 g, 1.65 mmol). The mixture was heated cautiously to reflux for 6 hours. After the reaction was completed, the solvent was removed by rotary vacuum evaporation and the residue was subjected to column chromatography (silica-gel H:300-400 mesh; petroleum ether/ethyl acetate=8:1 v/v) to yield 3.9 g of 3-(1-bromo-benzyl)-4-n-butyl-1-(4-trifluoromethyl)phenyl-1H-1,2,4-triazole-5 (4H)-one (111-2) (reddish-brown sticky liquid, yield: 85.9%).

Its structure was characterized by the following data from nuclear magnetic resonance spectroscopy:

$^1$H NMR (400 MHz, CDCl$_3$) δ 0.90 (t, J=7.36 Hz, 3H), 1.27-1.35 (m, 2H), 1.47-1.53 (m, 1H), 1.63-1.66 (m, 1H), 3.66-3.72 (m, 2H), 6.00 (s, 1H), 7.41-7.46 (m, 3H), 7.61 (dd, J=7.99 Hz, 1.83 Hz, 2H) 7.66 (d, J=8.69 Hz, 2H), 8.15 (d, J=8.57 Hz, 2H); $^{13}$C NMR (100 MHz, CDCl$_3$) δ 13.5, 19.9, 30.3, 41.5, 42.4, 118.2, 126.2, 126.8, 127.3, 128.6, 128.9, 129.5, 134.8, 140.4, 145.6, 152.2.

Example 9

Preparation of the Compound III-3

Preparation of the compound III-3 can be achieved according to the following reaction scheme:

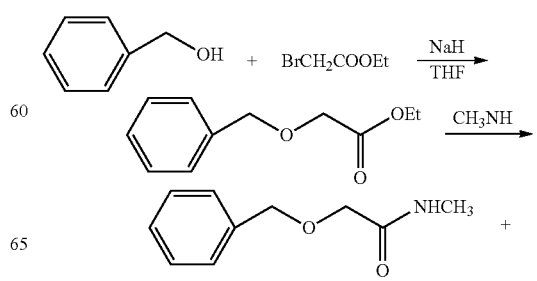

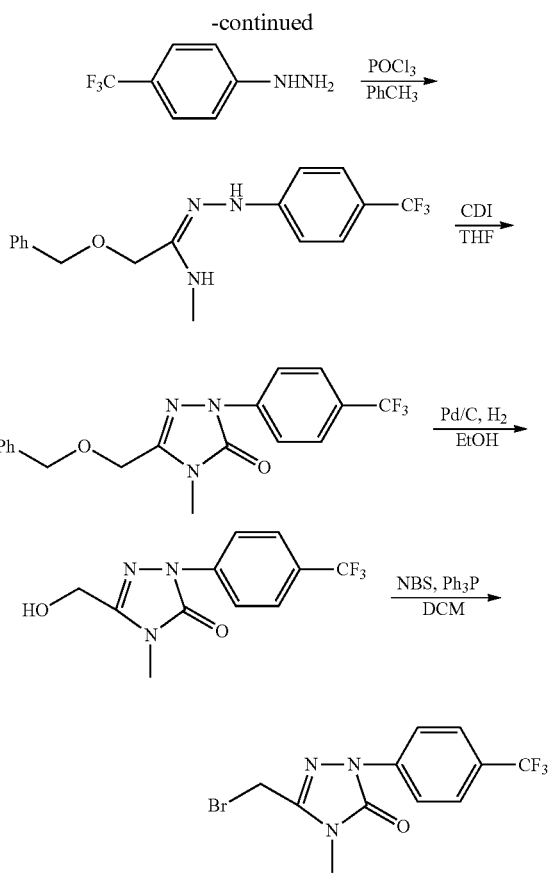

Preparation of N-methyl Benzoxoacetamide

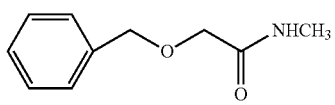 [SMILES: CNC(=O)COCc1ccccc1]

60% sodium hydride (3.7 g, 92.5 mmol) and tetrahydrofuran (20 ml) were added to a 250 ml three-necked flask, followed by heating, and dropwise addition of a 20 ml solution of benzyl alcohol (10 g, 96.1 mmol) in tetrahydrofuran. After the addition was completed, the reaction mixture was heated to reflux for 1 hour. Then ethyl bromoacetate (11 ml, 94.8 mmol) was added and the reaction mixture was stirred for another 4 hours under reflux. After cooling to room temperature, a 25 ml aqueous solution of methylamine was added thereinto, and the reaction was run under reflux for additional 6 hours. After the reaction was completed, it was concentrated under reduced pressure and subjected to column chromatography (silica-gel H: 300-400 mesh; petroleum ether/ethyl acetate=4:1 v/v) to yield 5.3 g of N-methyl benzoxoacetamide (white solid, two-steps yield: 32%).

Its structure was characterized by the following data from nuclear magnetic resonance spectroscopy:

$^1$H NMR (400 MHz, CDCl$_3$) δ 2.83 (d, J=5.16 Hz, 3H), 3.98 (s, 2H), 4.55 (S, 2 h), 6.61 (s, 1H), 7.30-7.39 (m, 5H).

Preparation of 3-benzoxomethyl-4-methyl-1-(4-trifluoromethyl-phenyl)-1,4-dihydrogen-1,2,4-triazole-5-one

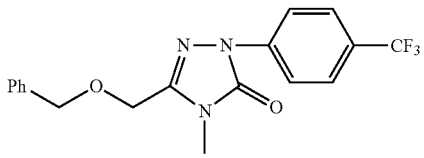 [SMILES: Cn1c(COCc2ccccc2)nn(-c2ccc(C(F)(F)F)cc2)c1=O]

In a 250 ml three-necked flask, to a stirred solution of N-methyl benzyloxyacetamide (6.4 g, 3.57 mmol) in toluene (40 ml) at 80-90° C. were added dropwise phosphorus oxychloride (3.6 ml, 38.5 mmol) in toluene (20 ml). The resulting reaction mixture was stirred at 80-90° C. for 5 hours. After the reaction was completed, it was cooled to room temperature and filtrated. The filter cake was washed with ethyl acetate until it became incarnadine. The filtrate was washed with a saturated aqueous solution of sodium bicarbonate, dried over anhydrous magnesium sulfate, filtrated, concentrated under reduced pressure, and filtrated again. The filter cake was washed again with ethyl acetate. The filter cakes were combined and vacuum-dried. Finally, 4.5 g of an incarnadine solid was obtained.

The above-mentioned incarnadine solid of 4.5 g was transferred into another 500 ml of three-necked flask, 200 ml of tetrahydrofuran (THF) was added thereinto, stirred, and carbonyldiimidazole (CDI) (5 g, 30.8 mmol) was slowly added thereinto. The reaction mixture was stirred at room temperature for 12 hours following the addition. After the reaction was completed, it was concentrated under reduced pressure and subjected to column chromatography (silica-gel H: 300-400 mesh; petroleum ether/ethyl acetate=4:1 v/v) to yield 3 g of 3-benzoxo methyl-4-methyl-1-(4-trifluoromethyl-phenyl)-1,4-dihydrogen-1,2,4-triazole-5-one (light brownish gelatinoids, two-steps yield: 23%).

Its structure was characterized by the following data from nuclear magnetic resonance spectroscopy:

$^1$H NMR (400 MHz, CDCl$_3$) δ 3.35 (s, 3H), 4.50 (s, 2H), 4.59 (s, 2H), 7.32-7.37 (m, 5H), 7.66 (d, J=8.46 Hz, 2H), 8.14 (d, J=8.46 Hz, 2H); $^{13}$C NMR (100 MHz, CDCl$_3$) δ 26.9, 27.8, 62.8, 72.9, 118.1, 126.1, 126.2, 126.3, 128.3, 128.5, 136.6, 140.5, 144.7, 152.5.

Preparation of 3-hydroxymethyl-4-methyl-1-(4-trifluoromethyl-phenyl)-1,4-dihydrogen-1,2,4-triazole-5-one

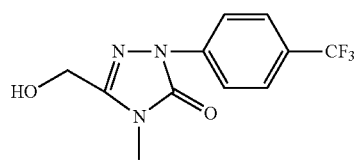 [SMILES: Cn1c(CO)nn(-c2ccc(C(F)(F)F)cc2)c1=O]

In a 250 ml three-necked flask, to a stirred solution of above-mentioned product 3-benzoxo methyl-4-methyl-1-(4-trifluoromethyl-phenyl)-1,4-dihydrogen-1,2,4-triazole-5- one (3.0 g, 8.3 mmol) in ethanol (60 ml) was added 1 g of 10% palladium on carbon. The 1 g of 10% palladium on carbon in the flask was replaced with $N_2$ and then hydrogen gas was introduced. The reaction mixture was stirred at room temperature for 24 hours. After the reaction was completed, it was filtrated and vacuum-concentrated to yield 2.1 g of 3-hydroxymethyl-4-methyl-1-(4-trifluoromethyl-phenyl)-1,4-dihydrogen-1,2,4-triazole-5-one (white solid, yield: 93%).

Its structure was characterized by the following data from nuclear magnetic resonance spectroscopy:

$^1$H NMR (400 MHz, CDCl$_3$) δ 3.34 (s, 3H), 4.52 (d, J=5.84 Hz, 2H), 5.77 (t, J=5.84 Hz, 1H), 7.85 (d, J=8.59 Hz, 2H), 8.17 (d, J=8.59 Hz, 2H); $^{13}$C NMR (100 MHz, CDCl$_3$) δ 27.9, 55.2, 118.0, 125.2, 125.5, 126.0, 141.3, 149.0, 152.5.

Preparation of 3-bromomethyl-4-methyl-1-(4-trifluoromethyl-phenyl)-1,4-dihydrogen-1,2,4-triazole-5-one (III-3)

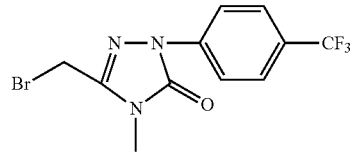 [SMILES: Cn1c(CBr)nn(-c2ccc(C(F)(F)F)cc2)c1=O]

In a 250 ml three-necked flask, to a stirred solution of the above-mentioned product (2.1 g, 7.77 mmol) in dichloromethane (100 ml) was added N-bromosuccinimide (NBS, 1.8 g, 10.1 mmol), followed by slow addition of triphenylphosphine (2.4 g, 9.15 mmol). The reaction was stirred at room temperature for 4 hours. After the reaction was completed, it was subjected to column chromatography (silica-gel H: 300-400 mesh; petroleum ether/ethyl acetate=5:1 v/v) to yield 2.3 g of 3-bromomethyl-4-methyl-1-(4-trifluoromethyl-phenyl)-1,4-dihydrogen-1,2,4-triazole-5-one (pale yellow solid, yield: 89%).

Its structure was characterized by the following data from nuclear magnetic resonance spectroscopy and Mass spectroscopy:

$^1$H NMR (400 MHz, CDCl$_3$) δ 3.42 (s, 3H), 4.34 (s, 2H), 7.67 (d, J=8.63 Hz, 2H), 8.12 (d, J=8.63 Hz, 2H); $^{13}$C NMR (100 MHz, CDCl$_3$) δ 19.1, 26.9, 27.9, 118.2, 126.2, 140.2, 143.5, 152.1; MS (ESI) m/z 332.27 (M-4)$^+$.

Preparation of the Compound (I) (Ester)

Example 10

Preparation of the Compound E-1

Preparation of ethyl 2-(2-methyl-4-(1-(3-(4-methyl-5-oxo-1-(4-trifluoromethyl-phenyl)-4,5-dihydrogen-1H-1,2,4-triazolyl))-benzyloxy)-phenoxy)-acetate (E-1)

In a 150 ml single-necked flask, to a stirred solution of 3-(1'-bromo-benzyl)-4-methyl-1-(4-trifluoromethyl)phenyl-1H-1,2,4-triazole-5(4H)-one (III-1) (36.3 g, 88.1 mmol) in acetonitrile (150 ml) were added ethyl (2-methyl-4-hydroxy)-phenoxy-acetate (1'-1) (17.5 g, 83.3 mmol), N,N-dimethylamino pyridine (DMAP, 0.5 g, 4.09 mmol), and potassium carbonate (K$_2$CO$_3$, 13.8 g, 99.9 mmol). The reaction mixture was stirred at room temperature for 8 hours. After the reaction was completed, it was filtrated. The filter cake was washed with ethyl acetate (3×50 ml) before being discarded. The filtrates were combined, subjected to rotary vacuum evaporation to remove the solvent, and then subjected to column chromatography (silica-gel H: 300-400 mesh; petroleum ether/ethyl acetate=8:1 v/v) to yield a colorless gelatinoids (which gradually became a white solid during being left stand) (33.5 g, yield: 74.3%).

Its structure was characterized by the following data from nuclear magnetic resonance spectroscopy and Mass spectroscopy:

$^1$H NMR (400 MHz, CDCl$_3$) δ 1.28 (t, J=7.11 Hz, 3H), 2.26 (s, 3H), 3.20 (s, 3H), 4.26 (q, J=7.11 Hz, 2H), 4.61 (s, 2H), 6.28 (s, 1H), 6.65 (d, J=8.8 Hz, 1H), 6.81 (d, J=8.75 Hz, 1H), 6.93 (d, J=3.0 Hz, 1H), 7.25-7.45 (m, 3H), 7.50 (d, J=7.32, 2H), 7.67 (d, J=8.48 Hz, 2H), 8.14 (d, J=8.48 Hz, 2H); $^{13}$C NMR (100 MHz, CDCl$_3$) δ 14.1, 16.7, 28.2, 61.3, 65.9, 75.1, 112.8, 113.2, 118.3, 119.3, 122.7, 125.8, 126.2, 127.1, 128.9, 129.0, 129.4, 135.1, 140.4, 146.3, 151.5, 152.8, 169.1; MS (ESI) m/z 558.9 (M+NH$_4^+$).

Example 11

Preparation of the Compound E-2

Using the compounds III-1 and II-5 as starting materials, ethyl 2-(2-methyl-4-(1-(3-(4-methyl-5-oxo-1-(4-trifluoromethyl-phenyl)-4,5-dihydrogen-1H-1,2,4-triazolyl))-benzyloxy)-phenylthio)-acetate (E-2) was prepared according to a chemical reaction procedure similar to that described in Example 9. It is a white solid with a yield of 60%.

Its structure was characterized by the following data from nuclear magnetic resonance spectroscopy and Mass spectroscopy:

$^1$H NMR (400 MHz, CDCl$_3$) δ 1.19 (t, J=7.12 Hz, 3H), 2.45 (s, 3H), 3.21 (s, 3H), 3.50 (s, 2H), 4.12 (q, J=7.12 Hz, 2H), 6.39 (s, 1H), 6.92 (dd, J=8.59 Hz, 2.82 Hz, 1H), 7.0, (d, J=2.82 Hz, 1H), 7.40-7.53 (m, 3H), 7.52 (d, J=7.48 Hz, 2H), 7.69 (d, J=8.76 Hz, 2H), 8.18 (d, J=8.76 Hz, 2H); $^{13}$C NMR (100 MHz, CDCl$_3$) δ 14.1, 20.9, 28.3, 37.1, 61.4, 74.6, 113.6, 117.9, 118.2, 125.4, 125.8, 126.2, 126.9, 127.3, 128.96, 129.1, 134.2, 134.7, 140.5, 142.2, 145.9, 152.6, 169.7; MS (ESI) m/z 558.01 (M+H)$^+$.

Example 12

Preparation of the Compound E-3

Using the compounds III-1 and II-4 as starting materials, ethyl 2-(3-methyl-4-(1-(3-(4-methyl-5-oxo-1-(4-trifluoromethyl-phenyl)-4,5-dihydrogen-1H-1,2,4-triazolyl))-benzyloxy)-phenylthio)-acetate (E-3) was prepared according to a chemical reaction procedure similar to that described in Example 9. It is a white solid with a yield of 71%.

Its structure was characterized by the following data from nuclear magnetic resonance spectroscopy and Mass spectroscopy:

$^1$H NMR (400 MHz, CDCl$_3$) δ 1.20 (t, J=7.10 Hz, 3H), 2.37 (s, 3H), 3.19 (s, 3H), 3.53 (s, 2H), 4.14 (q, J=7.10 Hz, 2H), 6.39 (s, 1H), 6.94 (d, J=8.58 Hz, 1H), 7.24 (dd, J=8.58 Hz, 2.4 Hz, 1H), 7.34 (d, J=2.4 Hz, 1H), 7.40-7.46 (m, 3H), 7.50 (d, J=7.52 Hz, 2H), 7.69 (d, J=8.84 Hz, 2H), 8.17 (d, J=8.84 Hz, 2H); $^{13}$C NMR (100 MHz, CDCl$_3$) δ 14.1, 16.5, 28.2, 38.0, 61.4, 74.5, 113.1, 118.2, 122.7, 125.4, 125.8, 126.2, 126.3, 127.1, 127.4, 128.0, 128.96, 129.1, 130.8, 134.8, 140.4, 145.9, 152.6, 169.8; MS (ESI) m/z 557.97 (M+H)⁺.

Example 13

Preparation of the Compound E-4

Preparation of ethyl 2-(2-methyl-4-(1-(3-(4-methyl-5-oxo-1-(4-trifluoromethyl-phenyl)-4,5-dihydrogen-1H-1,2,4-triazolyl))-benzylthio)-phenoxy)-acetate (E-4)

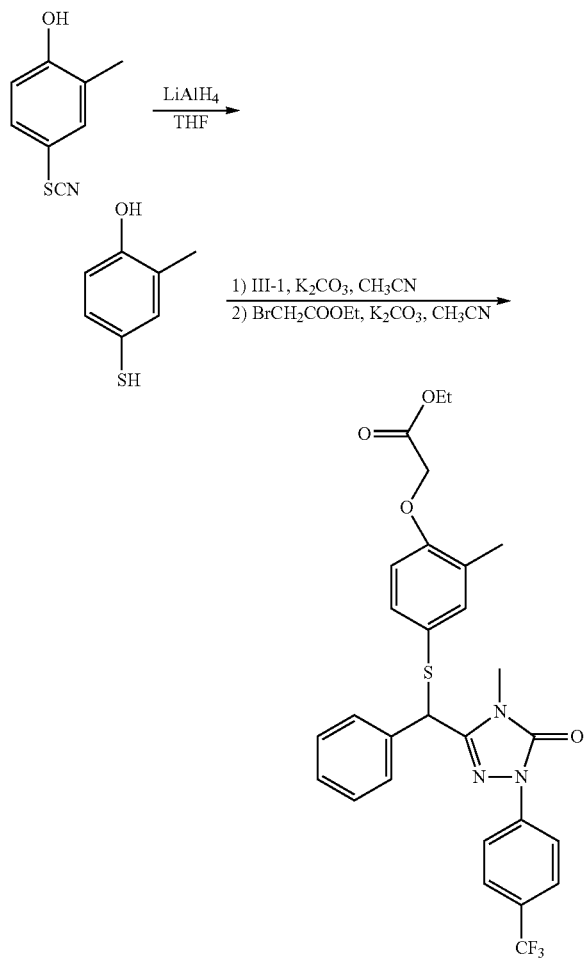

In a 250 ml three-necked flask with a constant-pressure dropping funnel, to a stirred mixture of lithium aluminum tetrahydride (LiAlH₄, 1.0 g, 26.3 mmol) and tetrahydrofuran (30 ml) was added dropwise at 0° C. a solution of 3-methyl-4-hydroxy-phenyl thiocyanic acid (1.7 g, 10.3 mmol) in tetrahydrofuran (THF, 30 ml). After 30 min of stirring at 0° C. and another 2 hours of stirring at room temperature, the reaction was quenched by addition of broken ice in an ice water bath. The value of pH of the mixture was adjusted to 3-4 by adding 6 M hydrochloric acid, and then the aqueous phase was extracted with ethyl acetate (3×100 ml). The combined organic layer was washed with a saturated solution of sodium chloride (2×100 ml), dried over anhydrous magnesium sulfate, filtrated, and evaporated in vacuo to yield a crude product of 3-methyl-4-hydroxy-mercaptobenzene (yellow liquid).

In a 150 ml single-necked flask, to a stirred solution of 3-(1'-bromo-benzyl)-4-methyl-1-(4-trifluoromethyl)phenyl-1H-1,2,4-triazole-5(4H)-one (III-1, 4.01 g, 9.73 mmol) in acetonitrile (30 ml) were added the freshly-prepared crude product of 3-methyl-4-hydroxy-mercaptobenzene in acetonitrile (30 ml), N,N-dimethylamino pyridine (DMAP, 0.07 g, 0.57 mmol), and potassium carbonate (K₂CO₃, 1.28 g, 9.27 mmol). After the reaction was stirred at room temperature for 4 hours, potassium carbonate (K₂CO₃, 1.4 g, 10.1 mmol) and ethyl bromoacetate (1.1 ml, 9.5 mmol) were added. The reaction mixture was stirred for another 8 hours. After the reaction was completed, it was filtrated. The filter cake was washed with ethyl acetate (3×30 ml) before being discarded. The filtrates were combined, subjected to rotary vacuum evaporation to remove the solvent, and then subjected to column chromatography (silica-gel H: 300-400 mesh; petroleum ether/ethyl acetate=5:1 v/v) to yield 4.4 g of a white solid (yield: 81%).

Its structure was characterized by the following data from nuclear magnetic resonance spectroscopy and Mass spectroscopy:

¹H NMR (400 MHz, CDCl₃) δ 1.26 (t, J=7.14 Hz, 3H), 2.19 (s, 3H), 3.15 (s, 3H), 4.23 (q, J=7.14 Hz, 2H), 4.58 (s, 2H), 5.17 (s, 1H), 6.54 (d, J=8.44 Hz, 1H), 7.11 (dd, J=8.32 Hz, 2.28 Hz, 1H), 7.17 (d, J=2.28 Hz, 1H), 7.33-7.38 (m, 5H), 7.66 (d, J=8.56 Hz, 2H), 8.10 (d, J=8.56 Hz, 2H); ¹³C NMR (100 MHz, CDCl₃) δ 14.1, 16.1, 28.0, 50.6, 61.4, 65.4, 113.6, 118.2, 122.8, 125.5, 126.2, 126.8, 127.1, 128.2, 128.5, 128.9, 133.8, 135.2, 137.8, 140.5, 146.5, 152.6, 157.1, 168.5; MS (ESI) m/z 558.03 (M+H)⁺.

Example 14

Preparation of the Compound E-5

Using the compounds III-1 and II-3 as starting materials, ethyl 2-(2-ethyl-4-(1-(3-(4-methyl-5-oxo-1-(4-trifluoromethyl-phenyl)-4,5-dihydrogen-1H-1,2,4-triazolyl))-benzyloxy)-phenyoxy)-acetate (E-5) was prepared according to a chemical reaction process similar to that described in Example 9. It is a white solid with a yield of 87.3%.

Its structure was characterized by the following data from nuclear magnetic resonance spectroscopy and Mass spectroscopy:

¹H NMR (400 MHz, CDCl₃) δ 1.19 (t, J=7.24 Hz, 3H), 1.27 (t, J=7.24 Hz, 3H), 2.67 (m, 2H), 3.20 (s, 3H), 4.24 (q, J=7.24 Hz, 2H), 4.57 (s, 2H), 6.29 (s, 1H), 6.81 (dd, J=8.88 Hz, 3.08 Hz, 1H), 6.95 (d, J=3.08 Hz, 1H), 7.36-7.45 (m, 3H), 7.52 (d, J=7.60 Hz, 2H), 7.67 (d, J=8.76 Hz, 2H), 8.16 (d, J=8.76 Hz, 2H); ¹³C NMR (100 MHz, CDCl₃) δ 13.9, 14.1, 23.2, 23.3, 28.3, 61.3, 66.3, 75.3, 112.5, 112.6, 112.96, 113.2, 116.5, 117.6, 118.2, 125.4, 125.9, 126.2, 127.3, 128.8, 128.96, 135.2, 135.3, 140.5, 146.4, 150.6, 151.3, 151.6, 152.8, 169.2; MS (ESI) m/z 556.29 (M+H)⁺.

Example 15

Preparation of the Compound E-6

Using the compounds III-1 and II-2 as starting materials, ethyl 2-(3-methyl-4-(1-(3-(4-methyl-5-oxo-1-(4-trifluoromethyl-phenyl)-4,5-dihydrogen-1H-1,2,4-triazolyl))-benzyloxy)-phenoxy)-acetate (E-6) was prepared according to a chemical reaction process similar to that described in Example 9. It is a white solid with a yield of 98%.

Its structure was characterized by the following data from nuclear magnetic resonance spectroscopy and Mass spectroscopy:

$^1$H NMR (400 MHz, CDCl$_3$) δ 1.32 (t, J=7.02 Hz, 3H), 2.24 (s, 3H), 3.25 (s, 3H), 4.29 (q, J=7.02 Hz, 2H), 4.59 (s, 2H), 6.35 (s, 1H), 6.56-6.75 (m, 1H), 6.88 (d, J=2.95 Hz, 1H), 6.95 (d, J=8.94 Hz, 1H), 7.42-7.55 (m, 3H), 7.58 (d, J=7.49 Hz, 2H), 7.72 (d, J=8.69 Hz, 2H), 8.23 (d, J=8.56 Hz, 2H); $^{13}$C NMR (100 MHz, CDCl$_3$) δ 14.1, 16.7, 28.2, 61.3, 65.96, 75.1, 112.1, 112.8, 113.9, 115.4, 117.8, 118.2, 118.5, 125.5, 125.8, 126.2, 126.9, 127.2, 128.8, 129.0, 135.3, 140.5, 146.4, 149.9, 152.7, 169.1; MS (ESI) m/z 541.9 (M+H$^+$); 558.9 (M+NH$_4^+$).

Example 16

Preparation of the Compound E-7

Preparation of ethyl 2-(3-methyl-4-(1-(3-(4-methyl-5-oxo-1-(4-trifluoromethyl-phenyl)-4,5-dihydrogen-1H-1,2,4-triazolyl))-benzylthio)-phenoxy)-acetate (E-7)

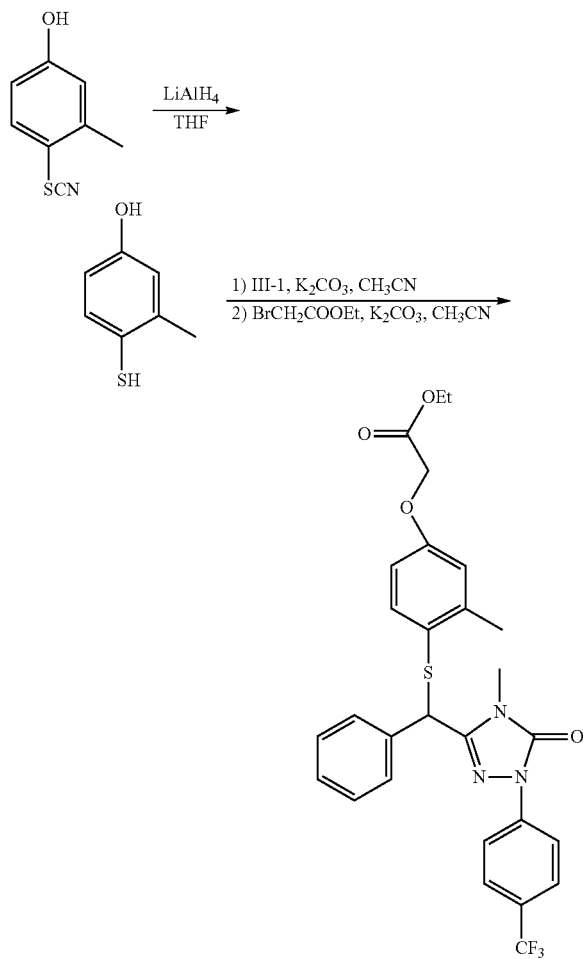

In a 250 ml three-necked flask, to a stirred mixture of lithium aluminum tetrahydride (LiAlH$_4$, 0.8 g, 21 mmol) and tetrahydrofuran (30 ml) was added dropwise a solution of 3-methyl-4-hydroxy-phenyl thiocyanic acid (1.1 g, 6.6 mmol) in tetrahydrofuran (THF 30 ml) at 0° C. (cooled with chilled water). After 30 min of stirring at 0° C. and another 2 hours of stirring at room temperature, the reaction was quenched by addition of broken ice in an ice water bath. The value of pH of the mixture was adjusted to 3-4 by adding 6 N hydrochloric acid, and then the aqueous phase was extracted with ethyl acetate (3×100 ml). The combined organic layer was washed with a saturated solution of sodium chloride (2×100 ml), dried over anhydrous magnesium sulfate, filtrated, and evaporated in vacuo to yield a crude product of 3-methyl-4-hydroxy-mercaptobenzene (yellow liquid).

In another 250 ml single-necked flask, to a stirred solution of the obtained 3-methyl-4-hydroxylmercaptobenzene in acetonitrile (30 ml) were added 3-(1-bromo-benzyl)-4-methyl-1-(4-trifluoromethyl)phenyl-1H-1,2,4-triazole-5(4H)-one (III-1, 2.5 g, 6.06 mmol), acetonitrile (30 ml), N,N-dimethylamino pyridine (DMAP, 0.1 g, 0.82 mmol) and potassium carbonate (K$_2$CO$_3$, 0.85 g, 6.15 mmol). After the mixture was stirred for 5 hours at room temperature, potassium carbonate (K$_2$CO$_3$, 1.6 g, 11.6 mmol) and ethyl bromoacetate (1.2 ml, 10.3 mmol) were added thereinto and the resulting reaction mixture was stirred at room temperature for another 8 hours. After the reaction was completed, it was filtrated. The filter cake was washed with ethyl acetate (3×50 ml) before being discarded. The filtrates were combined, subjected to rotary vacuum evaporation to remove the solvent, and then subjected to column chromatography (silica-gel H: 300-400 mesh; petroleum ether/ethyl acetate=8:1→5:1 v/v) to yield 2.0 g of a white solid (yield: 59%).

Its structure was characterized by the following data from nuclear magnetic resonance spectroscopy and Mass spectroscopy:

$^1$H NMR (400 MHz, CDCl$_3$) δ 1.27 (t, J=7.18 Hz, 3H), 2.31 (s, 3H), 3.13 (s, 3H), 4.24 (q, J=7.18 Hz, 2H), 4.55 (s, 2H), 5.09 (s, 1H), 6.59 (dd, J=8.56 Hz, 2.88 Hz, 1H), 6.78, (d, J=2.88 Hz, 1H), 7.24 (d, J=8.68 Hz, 1H), (7.30-7.34 (m, 4H), 7.66 (d, J=8.66 Hz, 2H), 8.10 (d, J=8.66 Hz, 2H); $^{13}$C NMR (100 MHz, CDCl$_3$) δ 14.1, 20.9, 28.1, 49.8, 61.5, 65.2, 112.6, 117.0, 118.2, 123.1, 125.5, 126.2, 126.8, 127.1, 128.0, 128.5, 128.9, 135.1, 137.9, 140.5, 144.5, 146.4, 152.5, 168.5; MS (ESI) m/z 558.05 (M+H)$^+$.

Example 17

Preparation of the Compound E-8

Preparation of ethyl 2-(2-methyl-4-(3-(4-methyl-5-oxo-1-(4-trifluoromethyl-phenyl)-4,5-dihydrogen-1H-1,2,4-triazolyl)-methylthio)-phenoxy)-acetate (E-8)

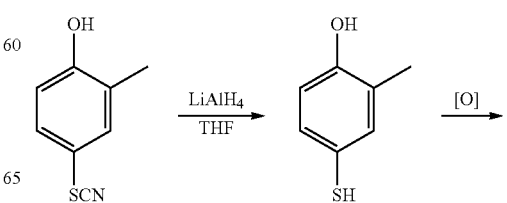

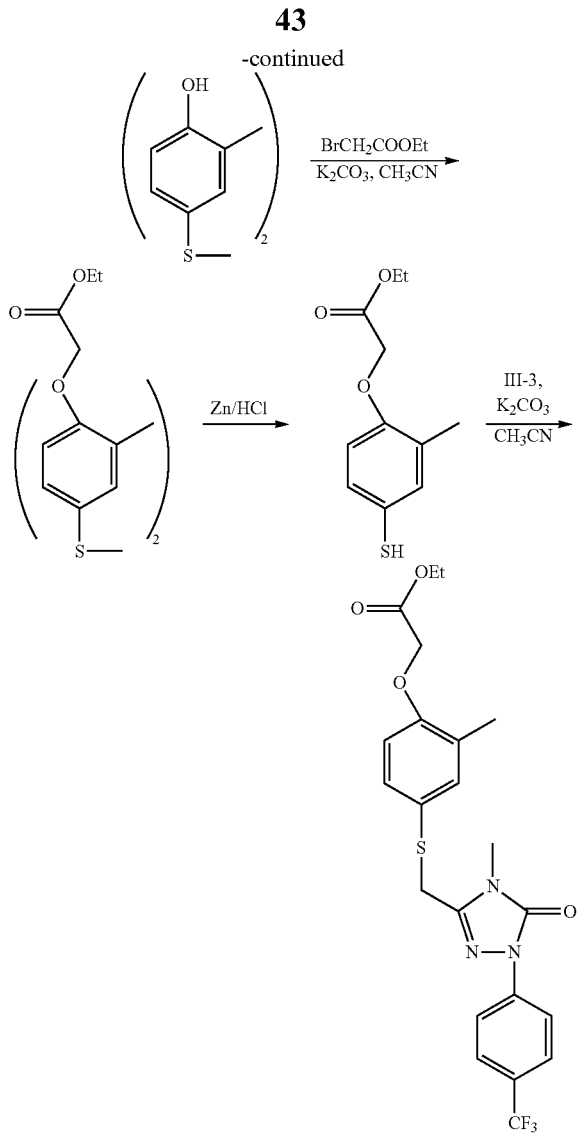

7.24 (d, J=2.24 Hz, 1H); $^{13}$C NMR (100 MHz, CDCl$_3$) δ 15.7, 115.5, 125.0, 128.3, 130.2, 134.0, 154.4; MS (ESI) m/z 278.33 (M+H$^+$).

In a 150 ml single-necked flask, to a stirred solution of 3-methyl-4-hydroxy-mercaptobenzene (1.6 g, 5.76 mmol) in acetonitrile (60 ml) were added ethyl bromoacetate (1.4 ml, 60.7 mmol) and potassium carbonate (K$_2$CO$_3$, 1.6 g, 11.6 mmol). After the reaction was stirred at room temperature for 12 hours, the reaction solution was diluted by adding 60 ml of ethyl acetate, filtrated, and evaporated to give a residue. The residue was purified by column chromatography (silica-gel H:300-400 mesh; petroleum ether/ethyl acetate=5:1 v/v) to yield 2.0 g of a pale-yellow jelly-like liquid (yield: 77.5%).

In a 150 ml three-necked flask, to a stirred solution of the above-described product (2.0 g, 4.44 mmol) in ethanol (15 ml) were added water (15 ml) and concentrated hydrochloride (7 ml). Zinc powder (10 g, 153 mmol) was added slowly with agitation. After the addition, the reaction mixture was stirred at room temperature for 30 min and then extracted with dichloromethane (3×60 ml). The organic phases were combined, dried over anhydrous magnesium sulfate, filtrated, and concentrated under reduced pressure to yield a pale-yellow liquid.

In a 150 ml single-necked flask, to a stirred solution of the above crude product in 30 ml of acetonitrile were added 30 ml of 3-(1'-bromo-benzyl)-4-methyl-1-(4-trifluoromethyl)phenyl-1H-1,2,4-triazole-5(4H)-one III-3 (1.3 g, 3.9 mmol) and potassium carbonate (K$_2$CO$_3$, 3.4 g, 24.6 mmol). The resulting reaction mixture was stirred at room temperature for 12 hours. After the reaction was completed, the reaction solution was diluted by adding 50 ml of ethyl acetate and filtrated. The filtrate was concentrated under reduced pressure, and subjected to column chromatography (silica-gel H:300-400 mesh; petroleum ether/ethyl acetate=3:1 v/v) to yield 1.7 g of a white solid (yield: 91%).

Its structure was characterized by the following data from nuclear magnetic resonance spectroscopy and Mass spectroscopy:

$^1$H NMR (400 MHz, CDCl$_3$) δ 1.25 (t, J=7.12 Hz, 3H), 2.22 (s, 3H), 3.37 (s, 3H), 3.87 (s, 2H), 4.21 (q, J=7.12 Hz, 2H), 4.58 (s, 2H), 6.58 (d, J=8.37 Hz, 1H), 7.16 (dd, J=8.37 Hz, 2.34 Hz, 1H), 7.23 (d, J=2.34 Hz, 1H), 7.63 (d, J=8.57 Hz, 2H), 7.98 (d, J=8.57 Hz, 2H); $^{13}$C NMR (100 MHz, CDCl$_3$) δ 14.1, 16.1, 27.8, 31.3, 61.3, 65.5, 111.6, 118.1, 122.7, 123.5, 125.4, 126.1, 128.1, 128.6, 132.4, 136.3, 140.5, 144.6, 152.4, 156.8, 168.5; MS (ESI) m/z 482.49 (M+H)$^+$.

Example 18

Preparation of the Compound E-9

Using the compounds III-3 and II-2 as starting materials, ethyl 2-(2-methyl-4-(3-(4-methyl-5-oxo-1-(4-trifluoromethyl-phenyl)-4,5-dihydrogen-1H-1,2,4-triazolyl)-methoxy)-phenoxy)-acetate (E-9) was prepared according to a chemical reaction process similar to that described in Example 9. It is a white solid with a yield of 73.5%.

Its structure was characterized by the following data from nuclear magnetic resonance spectroscopy and Mass spectroscopy:

$^1$H NMR (400 MHz, CDCl$_3$) δ 1.32 (t, J=7.14 Hz, 3H), 2.33 (s, 3H), 3.45 (s, 3H), 4.28 (q, J=7.14 Hz, 2H), 4.63 (s, 2H), 5.01 (s, 2H), 6.71 (d, J=8.85 Hz, 1H), 6.8 (dd, J=8.85 Hz, 3.08 Hz, 1H), 6.88 (d, J=3.08 Hz, 1H), 7.70 (d, J=8.56 Hz, 2H), 8.17 (d, J=8.55 Hz, 2H); $^{13}$C NMR (100 MHz, CDCl$_3$) δ 14.1, 16.2, 61.2, 61.9, 66.4, 112.0, 112.7, 117.7, 118.2,

In a 250 ml three-necked flask, to a stirred mixture of lithium aluminum tetrahydride (LiAlH$_4$, 1.0 g, 26.3 mmol) and tetrahydrofuran (30 ml) was added dropwise a solution of 3-methyl-4-hydroxy-phenyl thiocyanic acid (1.38 g, 8.35 mmol) in tetrahydrofuran (20 ml) at 0° C. After 30 min of stirring at 0° C., the reaction was allowed to warm up to room temperature and stirred for another 2 hours at room temperature. Then, the reaction was quenched by adding ethanol (10 ml). The value of pH of the mixture was adjusted to 3-4 by adding 6 M hydrochloric acid in an ice water bath, and then the aqueous phase was extracted with ethyl acetate (3×80 ml). The combined organic layer was dried over anhydrous magnesium sulfate, filtrated, concentrated under reduced pressure, left stand in the air for a whole day, and purified by column chromatography (silica-gel H:300-400 mesh; petroleum ether/ethyl acetate=5:1 v/v) to yield 1.6 g of a coupled compound of 3-methyl-4-hydroxy-mercaptobenzene (yellow jelly-like liquid, yield: 68.8%).

Its structure was characterized by the following data from nuclear magnetic resonance spectroscopy and Mass spectroscopy:

$^1$H NMR (400 MHz, CDCl$_3$) δ 2.2 (s, 3H), 5.35 (s, 1H), 6.69 (d, J=8.28 Hz, 1H), 7.18 (dd, J=8.23 Hz, 2.23 Hz, 1H), 118.3, 126.2, 126.3, 129.3, 140.5, 143.9, 151.6, 151.8, 152.4, 169.1; MS (ESI) m/z 464.39 (M−1), 466.48 (M+H)⁺.

Example 19

Preparation of the Compound E-10

Using the compounds III-1 and II-6 as starting materials, ethyl 2-(2,5-dimethyl-4-(1-(3-(4-methyl-5-oxo-1-(4-trifluoromethyl-phenyl)-4,5-dihydrogen-1H-1,2,4-triazolyl))-benzyloxy)-phenylthio)-acetate (E-10) was prepared according to a chemical reaction process similar to that described in Example 9. It is a yellow jelly-like liquid with a yield of 72.2%.

Its structure was characterized by the following data from nuclear magnetic resonance spectroscopy and Mass spectroscopy:

$^1$H NMR (400 MHz, CDCl$_3$) δ 1.29 (t J=7.16 Hz, 3H), 2.32 (s, 3H), 2.37 (s, 3H), 3.18 (s, 3H), 3.51 (s, 2H), 4.25 (q, J=7.16 Hz, 2H), 6.39 (s, 1H), 6.88 (s, 1H), 7.31 (s, 1H), 7.39-7.52 (m, 5H), 7.69 (d, J=8.67 Hz, 2H), 8.16 (d, J=8.67 Hz, 2H); $^{13}$C NMR (100 MHz, CDCl$_3$) δ 16.0, 20.7, 28.2, 37.2, 74.4, 114.7, 118.2, 125.4, 125.6, 125.7, 126.3, 128.9, 129.1, 134.9, 135.7, 139.5, 140.4, 146.1, 152.7, 155.0, 168.7; MS (ESI) m/z 573.07 (M+H)⁺.

Example 20

Preparation of the Compound E-11

Using the compounds III-3 and II-4 as starting materials, ethyl 2-(3-methyl-4-(3-(4-methyl-5-oxo-1-(4-trifluoromethyl-phenyl)-4,5-dihydrogen-1H-1,2,4-triazolyl)-methoxy)-phenylthio)-acetate (E-11) was prepared according to a chemical reaction process similar to that described in Example 9. It is a pale-yellow solid with a yield of 69.7%.

Its structure was characterized by the following data from nuclear magnetic resonance spectroscopy and Mass spectroscopy:

$^1$H NMR (400 MHz, CDCl$_3$) δ 1.32 (t, J=7.14 Hz, 3H), 2.19 (s, 3H), 3.43 (s, 3H), 3.55 (s, 2H), 4.28 (q, J=7.14 Hz, 2H), 5.03 (s, 2H), 6.91 (d, J=8.77 Hz, 3H), 7.29-7.32 (m, 2H), 7.67 (d, J=8.66 Hz, 2H), 8.12 (d, J=8.66 Hz, 2H); $^{13}$C NMR (100 MHz, CDCl$_3$) δ 16.1, 28.1, 38.1, 61.4, 111.8, 118.3, 126.2, 126.3, 127.2, 127.5, 127.9, 130.8, 134.8, 140.3, 143.6, 152.5, 155.4, 169.2; MS (ESI) m/z 481.23 (M−1)⁻, 482.34 (M)⁻, 483.35 (M−H)⁻.

Example 21

Preparation of the Compound E-12

Preparation of ethyl 2-(2,5-dimethyl-4-(1-(3-(4-methyl-5-oxo-1-(4-trifluoromethyl-phenyl)-4,5-dihydrogen-1H-1,2,4-triazolyl))-benzylthio)-phenoxy)-acetate (E-12)

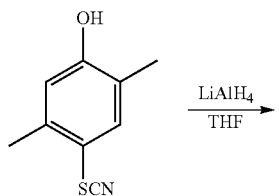

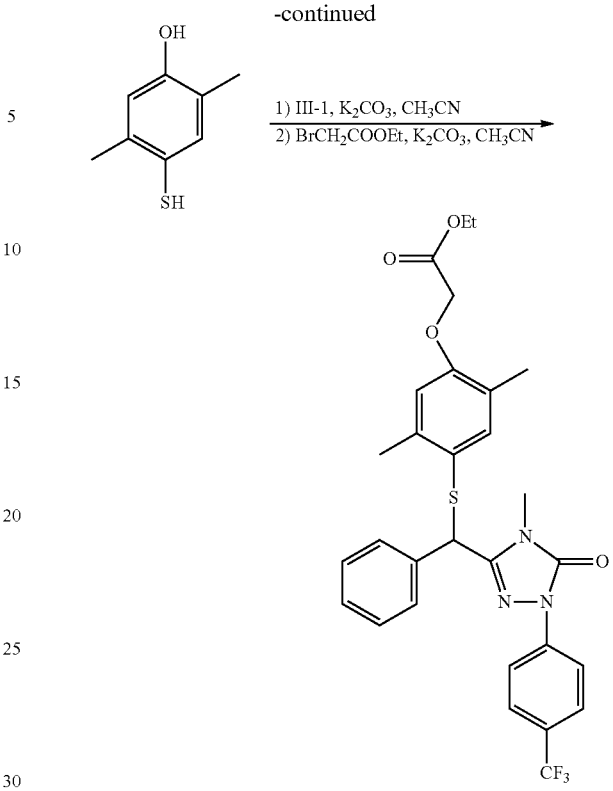

In a 250 ml three-necked flask, to a stirred mixture of lithium aluminum tetrahydride (LiAlH$_4$, 1.0 g, 26.3 mmol) and tetrahydrofuran (40 ml) was added dropwise a solution of 2,5-dimethyl-4-hydroxy-phenyl thiocyanic acid (1.2 g, 6.7 mmol) in 20 ml tetrahydrofuran at 0° C. After 30 min of stirring at 0° C., the mixture was allowed to warm up to room temperature and then stirred for another 1 hour at room temperature. The reaction was quenched by adding ethanol (10 ml). The value of pH of the mixture was adjusted to 3-4 by adding 6 M hydrochloric acid in an ice water bath, and then the aqueous phase was extracted with ethyl acetate (3×60 ml). The combined organic layer was dried over anhydrous magnesium sulfate, filtrated, and evaporated in vacuo to yield the crude product of 2,5-dimethyl-4-hydroxy-mercaptobenzene (yellow liquid).

In another 250 ml single-necked flask, to a stirred solution of the obtained crude product of 2,5-dimethyl-4-hydroxy-mercaptobenzene in acetonitrile (60 ml) were added 3-(1'-bromo-benzyl)-4-methyl-1-(4-trifluoromethyl)phenyl-1H-1, 2,4-triazole-5(4H)-one (III-1 (1.6 g, 3.88 mmol) and potassium carbonate (K$_2$CO$_3$, 0.54 g, 3.9 mmol). After the mixture was stirred for 4 hours at room temperature, ethyl bromoacetate (1.8 ml, 15.5 mmol) and potassium carbonate (K$_2$CO$_3$, 0.54 g, 3.9 mmol) were added thereinto. The mixture was stirred at room temperature overnight. After the reaction was completed, the reaction solution was diluted with 200 ml of ethyl acetate, and filtrated. The filtrate was evaporated to give a residue which was purified by column chromatography column chromatography (silica-gel H:300-400 mesh; petroleum ether/ethyl acetate=5:1 v/v) to yield 1.1 g of a yellow jelly-like liquid (three-step yield: 50%).

Its structure was characterized by the following data from nuclear magnetic resonance spectroscopy and Mass spectroscopy:

$^1$H NMR (400 MHz, CDCl$_3$) δ 1.28 (t J=7.16 Hz, 3H), 2.12 (s, 3H), 2.25 (s, 3H), 3.13 (s, 3H), 4.25 (q, J=7.16 Hz, 2H), 4.59 (s, 2H), 5.08 (s, 1H), 6.51 (s, 1H), 7.13 (s, 1H), 7.27-35 (m, 5H), 7.66 (d, J=8.75 Hz, 2H), 8.10 (d, J=8.75 Hz, 2H); $^{13}$C NMR (100 MHz, CDCl$_3$) δ 14.1, 15.5, 20.7, 28.0, 50.0, 61.3, 65.5, 113.1, 117.9, 118.2, 122.4, 125.9, 126.1, 126.2, 126.8, 128.1, 128.4, 128.8, 129.1, 135.2, 138.9, 140.5, 141.5, 146.5, 152.6, 157.0, 168.6; MS (ESI) m/z 588.31 (M+NH$_4$$^+$).

Example 22

Preparation of the Compound E-13

Preparation of ethyl 2-methyl-2-(2-methyl-4-(1-(3-(4-methyl-5-oxo-1-(4-trifluoromethyl-phenyl)-4,5-dihydrogen-1H-1,2,4-triazolyl))-benzylthio)-phenoxy)-acetate (E-13)

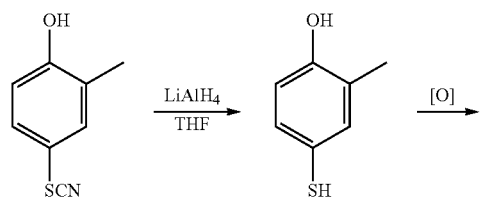

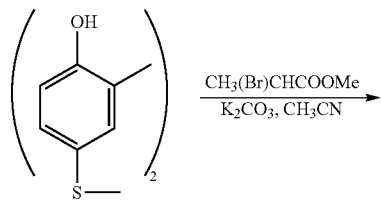

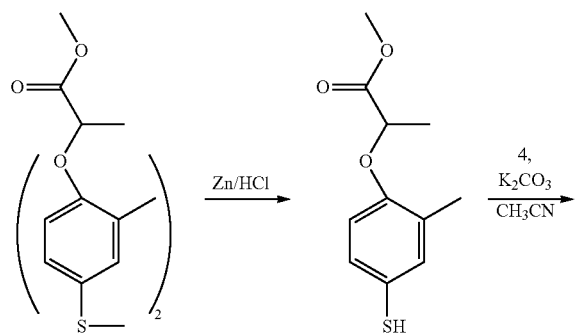

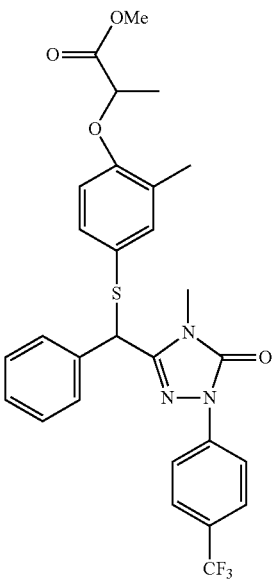

In a 250 ml three-necked flask, to a stirred mixture of lithium aluminum tetrahydride (LiAlH$_4$, 1.0 g, 26.4 mmol) and tetrahydrofuran (THF 30 ml) was added dropwise a solution of 3-methyl-4-hydroxy-phenyl thiocyanic acid (1.38 g, 8.35 mmol) in 20 ml of tetrahydrofuran at 0° C. After 30 min of stirring at 0° C., the mixture was allowed to warm up to room temperature and then stirred for another 2 hours at room temperature. The reaction was quenched by adding ethanol (10 ml). The value of pH of the mixture was adjusted to pH 3-4 by adding 6 N hydrochloric acid in an ice water bath, and then the aqueous phase was extracted with ethyl acetate (3×80 ml). The combined organic layer was dried over anhydrous magnesium sulfate, filtrated, concentrated under reduced pressure, and purified by column chromatography (silica-gel H:300-400 mesh; petroleum ether/ethyl acetate=5:1 v/v) to yield 1.44 g of a disulfide (yellow jelly-like liquid, yield: 62%).

Its structure was characterized by the following data from nuclear magnetic resonance spectroscopy and Mass spectroscopy:

$^1$H NMR (400 MHz, CDCl$_3$) δ 2.2 (s, 3H), 5.35 (s, 1H), 6.69 (d, J=8.28 Hz, 1H), 7.18 (dd, J=8.23 Hz, 2.23 Hz, 1H), 7.24 (d, J=2.24 Hz, 1H); $^{13}$C NMR (100 MHz, CDCl$_3$) δ 15.7, 115.5, 125.0, 128.3, 130.2, 134.0, 154.4; MS (ESI) m/z 278.33 (M+H)$^+$.

In 250 ml single-necked flask, to a stirred solution of above crude product (0.7 g, 2.59 mmol) in acetonitrile (60 ml) were added methyl 2-bromo-propionate (0.7 ml, 6.0 mmol) and potassium carbonate (K$_2$CO$_3$, 2 g, 14.5 mmol). The resulting mixture was stirred at room temperature overnight. After the reaction was completed, the reaction mixture was diluted with ethyl acetate (100 ml), and filtrated. The combined solution was evaporated under reduced pressure to give a residue which was purified by chromatography (silica-gel H:300-400 mesh; petroleum ether/ethyl acetate=5:1 v/v) to yield 1.0 g of a yellow jelly-like liquid (yield: 86%).

Its structure was characterized by the following data from nuclear magnetic resonance spectroscopy:

$^1$H NMR (400 MHz, CDCl$_3$) δ 1.63 (d, J=6.84 Hz, 1H); 2.34 (s, 3H), 3.75 (s, 3H), 4.73 (q, J=6.84 Hz, 1H), 6.57-6.61 (m, 1H), 7.19-7.27 (m, 2H).

In a 250 ml single-necked flask, to a stirred solution of the above-described product (1.0 g, 2.22 mmol) in ethanol (15 ml) were added 15 ml of water and 5 ml of concentrated hydrochloric acid. Zinc powder (10 g, 153 mmol) was added slowly. After the addition, the reaction mixture was stirred at room temperature for 30 min and then extracted with dichloromethane (3×50 ml). The organic phases were combined, dried over anhydrous magnesium sulfate, filtrated, and concentrated under reduced pressure to yield a pale-yellow liquid.

In a 150 ml single-necked flask, to a stirred solution of the above crude product in 30 ml of acetonitrile were added a solution of 3-(1'-bromo-benzyl)-4-methyl-1-(4-trifluoromethyl)phenyl-1H-1,2,4-triazole-5(4H)-one (III-1) (1.8 g, 4.36 mmol) in acetonitrile (30 ml) and potassium carbonate ($K_2CO_3$, 2.5 g, 18.1 mmol). The reaction mixture was stirred at room temperature for 6 hours. After the reaction was completed, the reaction mixture was diluted by adding 100 ml of ethyl acetate, filtrated, concentrated under reduced pressure, and subjected to column chromatography (silica-gel H:300-400 mesh; petroleum ether/ethyl acetate=5:1 v/v) to yield 1.2 g E-13 (a pair of diastereoisomers) (a pale-yellow jelly-like liquid, yield: 50%).

Its structure was characterized by the following data from nuclear magnetic resonance spectroscopy:

$^1$H NMR (400 MHz, CDCl$_3$) δ 1.61 (d, J=6.84 Hz, 1H); 2.18 (s, 3H), 3.15 (s, 3H), 3.70 (d, J=12.61 Hz, 3H); 4.70 (q, J=6.82 Hz, 1H); 5.18 (s, 1H); 6.51 (d, J=8.46 Hz, 1H), 7.0-7.11 (m, 1H), 7.10-7.15 (m, 1H), 7.34-7.37 (m, 5H), 7.67 (d, J=8.74 Hz, 2H), 8.11 (d, J=8.74 Hz, 2H); $^{13}$C NMR (100 MHz, CDCl$_3$) δ 16.1, 18.5, 28.1, 50.6, 52.2, 72.7, 112.1, 118.2, 123.0, 125.5, 126.2, 126.8, 127.1, 128.2, 128.5, 128.9, 133.8, 135.2, 137.7, 140.6, 146.5, 152.6, 156.9, 172.2.

Example 23

Preparation of the Compound E-14

Preparation of ethyl 2-(2-ethyl-4-(1-(3-(4-methyl-5-oxo-1-(4-trifluoromethyl-phenyl)-4,5-dihydrogen-1H-1,2,4-triazolyl))-benzylthio)-phenoxy)-acetate (E-14)

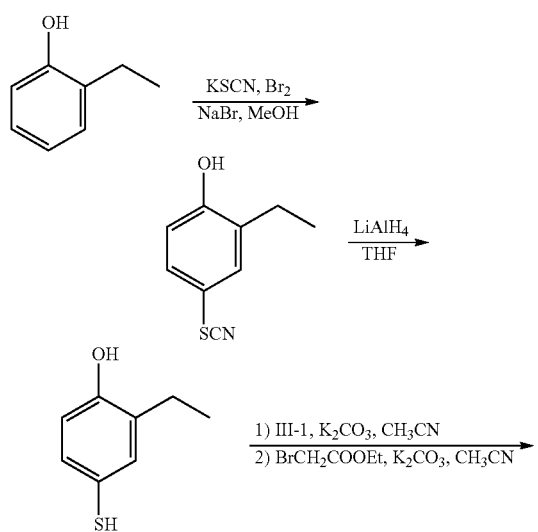

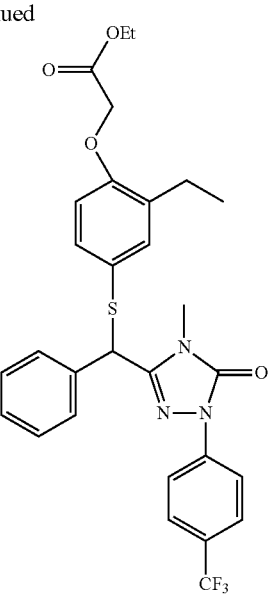

To a 500 ml three-necked flask were added sequentially o-ethylphenol (5 g, 40.9 mmol), sodium thiocyanate (10 g, 123.3 mmol), sodium bromide (4.3 g, 41.79 mmol) and methanol (100 ml). The mixture was cooled to 0° C. in an ice bath and then a solution of bromine (2.6 ml, 50.6 mmol) in methanol (50 ml) was added dropwise thereinto. After 1 hour of stirring at 0° C., the mixture was allowed to warm up to room temperature and then stirred for another 4 hours at room temperature. A 200 ml saturated aqueous solution of sodium bicarbonate was added slowly to the reaction mixture and stirred for 10 min. The mixture was extracted with ethyl acetate (2×300 ml). The combined organic layer was dried over anhydrous magnesium sulfate, and filtrated. Filtrate was concentrated under reduced pressure to give a reddish-brown sticky liquid. Column chromatography was performed (silica-gel H: 300-400 mesh; petroleum ether/ethyl acetate=5:1 v/v) to obtain 6.8 g of 3-ethyl-4-hydroxy-phenyl thiocyanic acid (reddish-brown sticky liquid, yield: 93%).

Its structure was characterized by the following data from nuclear magnetic resonance spectroscopy:

$^1$H NMR (400 MHz, DMSO) δ 1.25 (t J=7.28 Hz, 3H), 2.64 (q, J=7.53 Hz, 2H), 5.46 (s, 1H), 6.80 (d, J=8.36 Hz, 1H), 7.28 (dd, J=8.36 Hz, 2.52 HZ, 1H), 7.34 (d, J=2.48.36 Hz, 1H).

In a 150 ml three-necked flask, to a stirred mixture of lithium aluminum tetrahydride (LiAlH$_4$, 1.0 g, 26.2 mmol) and tetrahydrofuran (40 ml) was added dropwise a solution of 3-ethyl-4-hydroxy-phenyl thiocyanic acid (1.3 g, 7.25 mmol) in 20 ml tetrahydrofuran at 0° C. After 30 min of stirring at 0° C., the mixture was allowed to warm up to room temperature and then stirred for another 1 hour at room temperature. The reaction was quenched by adding ethanol (10 ml). The value of pH of the mixture was adjusted to pH 3-4 by adding 6 N hydrochloric acid in an ice water bath, and then the aqueous phase was extracted with ethyl acetate (3×60 ml). The combined organic layer was dried over anhydrous magnesium sulfate, filtrated, and evaporated in vacuo to yield the crude product of 3-ethyl-4-hydroxy-mercaptobenzene (yellow liquid).

In another 150 ml single-necked flask, to a stirred solution of resulting crude product of 3-ethyl-4-hydroxylmercaptobenzene in acetonitrile (20 ml) was added potassium carbonate ($K_2CO_3$, 1.0 g, 7.23 mmol), followed by dropwise addition of a solution of 3-(f-bromo-benzyl)-4-methyl-1-(4-trifluoromethyl)phenyl-1H-1,2,4-triazole-5(4H)-one (III-1) (1.6 g, 3.88 mmol) in 20 ml of acetonitrile. After the mixture was stirred for 6 hours at room temperature, potassium carbonate ($K_2CO_3$, 1.0 g, 7.23 mmol) and ethyl bromoacetate (1.6 ml, 13.8 mmol) were added thereinto. The mixture was stirred for another 8 h at the same temperature. After the reaction was completed, the reaction mixture was diluted with ethyl acetate (50 ml), and filtrated. The filtrate was evaporated to give a residue, which was purified by column chromatography (silica-gel H:300-400 mesh; petroleum ether/ethyl acetate=5:1 v/v) to yield 1.3 g of E-14 (a yellow gelatinoids, three-steps yield: 58.6%).

Its structure was characterized by the following data from nuclear magnetic resonance spectroscopy and Mass spectroscopy:

$^1$H NMR (400 MHz, DMSO) δ 1.09 (t J=7.48 Hz, 3H), 1.26 (t J=7.28 Hz, 3H), 2.59 (q, J=7.52 Hz, 2H), 3.15 (s, 3H), 4.22 (q, J=7.20 Hz, 2H), 4.58 (s, 2H), 5.18 (s, 1H), 6.56 (d, J=8.20 Hz, 1H), 7.15 (dd, J=8.32 Hz, 2.28 HZ, 1H), 7.31-7.36 (m, 5H), 7.66 (d, J=8.72 Hz, 1H), 8.11 (d, J=8.52 Hz, 1H); $^{13}$C NMR (100 MHz, CDCl$_3$) δ 13.7, 14.1, 23.0, 28.1, 50.6, 61.3, 65.4, 111.5, 118.2, 123.3, 126.1, 126.8, 127.1, 128.2, 128.5, 128.9, 133.8, 134.3, 135.2, 136.2, 140.5, 146.5, 152.6, 156.7, 168.5; MS (ESI) m/z 572.14 (M+H$^+$); 589.1 (M+NH$_4^+$).

Example 24

Preparation of the Compound E-15

Preparation of ethyl 2,2-dimethyl-2-(3-methyl-4-(1-(3-(4-methyl-5-oxo-1-(4-trifluoromethyl-phenyl)-4,5-dihydrogen-1H-1,2,4-triazolyl))-benzyloxy)-phenylthio)-acetate (E-15)

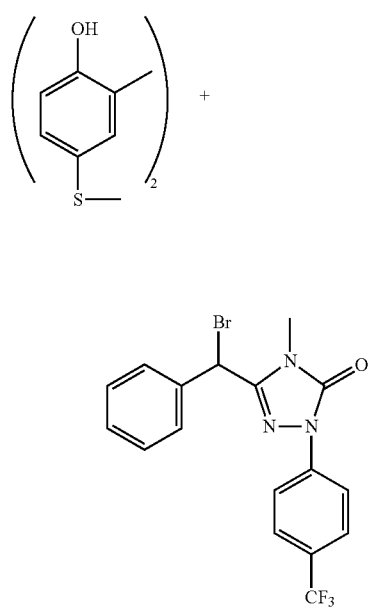

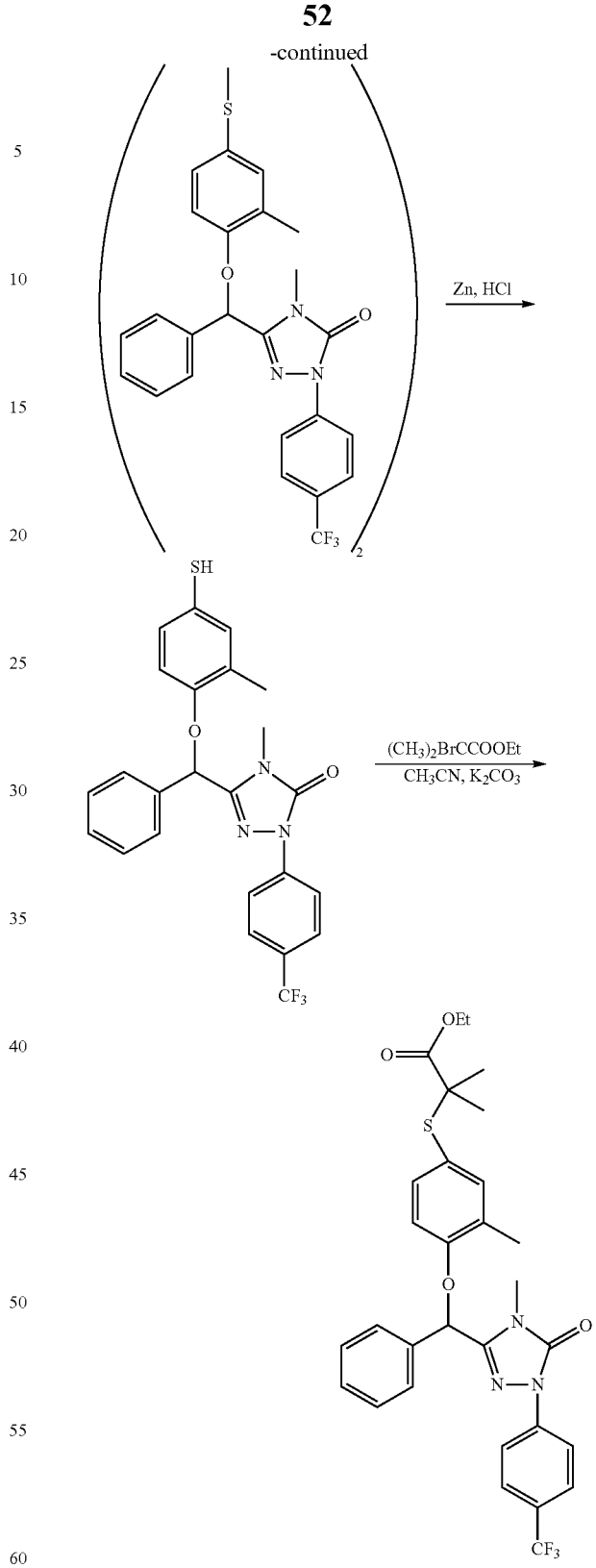

In a 150 ml single-necked flask, to a stirred solution of 3-methyl-4-hydroxy-mercaptobenzene (0.52 g, 1.87 mmol) in acetonitrile (30 ml) were added bromide III-1 (1.53 g, 3.71 mmol) and potassium carbonate ($K_2CO_3$, 2.5 g, 18.1 mmol). The mixture was stirred for 12 hours at room temperature. After the reaction was completed, the reaction mixture was diluted with ethyl acetate (100 ml), and filtrated. The filtrate was evaporated to give a residue, which was subjected to column chromatography (silica-gel H:300-400 mesh; petroleum ether/ethyl acetate=5:1 v/v) to yield 1.4 g of a pale-yellow jelly-like liquid.

In a 150 ml three-necked flask, to a stirred solution of the above-described product (1.4 g, 1.48 mmol) in ethanol (15 ml) were added 15 ml of water and 5 ml of concentrated hydrochloric acid. Zinc powder (10 g, 153 mmol) was added slowly. After the addition, the reaction was stirred at room temperature for 30 min and then extracted with dichloromethane (3×50 ml). The organic phases were combined, dried over anhydrous magnesium sulfate, filtrated, and concentrated under reduced pressure to yield a pale-yellow liquid.

In a 150 ml single-necked flask, to a stirred solution of above crude product in acetonitrile (30 ml) were added ethyl 2-bromo-isopropionate (3 ml, 20.2 mmol) in acetonitrile (30 ml) and potassium carbonate ($K_2CO_3$, 2.0 g, 14.4 mmol). The reaction mixture was stirred for 12 hours at room temperature. After the reaction was completed, the reaction mixture was diluted with ethyl acetate (100 ml), and filtrated. The filtrate was evaporated to give a residue, which was purified by column chromatography (silica-gel H:300-400 mesh; petroleum ether/ethyl acetate=5:1 v/v) to yield 0.58 g of E-15 (colorless gelatinoids, three-step yield: 26.6%).

Its structure was characterized by the following data from nuclear magnetic resonance spectroscopy and Mass spectroscopy:

$^1$H NMR (400 MHz, $CDCl_3$) δ 1.19 (t, J=7.20 Hz, 3H), 1.45 (s, 6H), 2.37 (s, 3H), 3.20 (s, 3H), 4.10 (q, J=7.20 Hz, 2H), 6.41 (s, 1H), 6.94 (d, J=8.52 Hz, 1H), 7.25 (dd, J=8.52 Hz, 1.8 Hz, 1H), 7.32 (d, J=1.8 Hz, 1H), 7.39-7.52 (m, 5H), 7.69 (d, J=8.52 Hz, 2H), 8.17 (d, J=8.52 Hz, 2H); $^{13}$C NMR (100 MHz, $CDCl_3$) δ 14.1, 16.4, 25.8, 28.2, 50.9, 61.1, 74.5, 112.4, 118.2, 124.2, 125.7, 126.2, 126.3, 127.4, 129.0, 129.1, 134.7, 136.1, 139.9, 140.4, 145.9, 152.6, 156.2, 173.9; MS (ESI) m/z 584.71 (M-H)$^-$.

Example 25

Preparation of the Compound E-16

Preparation of ethyl 2,2-dimethyl-2-(3-methyl-4-(1-(2-(4-methyl-5-oxo-1-(4-trifluoromethyl-phenyl)-4,5-dihydrogen-1H-1,2,4-triazolyl))-benzylthio)-phenoxy)-acetate (E-16)

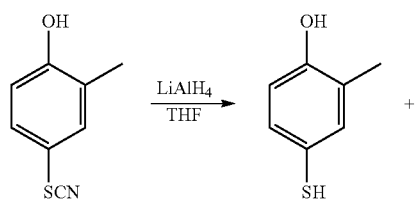

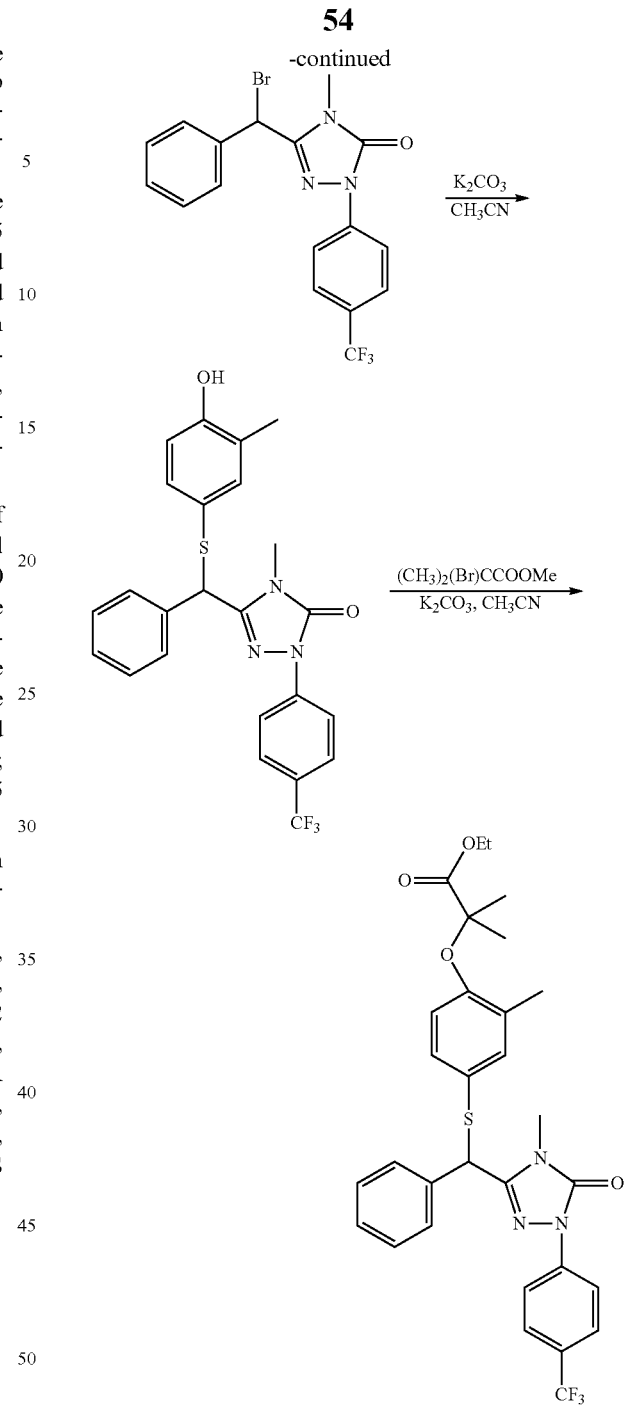

In a 250 ml three-necked flask, to a stirred mixture of lithium aluminum tetrahydride ($LiAlH_4$, 2.0 g, 52.7 mmol) and tetrahydrofuran (40 ml) was added dropwise a solution of 3-methyl-4-hydroxy-phenyl thiocyanic acid (2.5 g, 15.13) in tetrahydrofuran (30 ml) at 0° C. After 30 min of stirring at 0° C., the mixture was allowed to warm up to room temperature and then stirred for another 2 hours at room temperature. The reaction was quenched by adding ethanol (10 ml). The value of pH of the mixture was adjusted to pH 3-4 by adding 6 M hydrochloric acid in an ice water bath, and then the aqueous phase was extracted with ethyl acetate (3×100 ml). The combined organic layer was dried over anhydrous magnesium sulfate, filtrated, and evaporated in vacuo to yield a yellow liquid.

In a 250 ml single-necked flask, to a stirred solution of the resulting yellow liquid in acetonitrile (30 ml) were added bromide III-1 (3.2 g, 7.76 mmol) and potassium carbonate (K$_2$CO$_3$, 1.15 g, 8.32 mmol). The mixture was stirred for 6 hours at room temperature. After the reaction completed, the reaction mixture was diluted with ethyl acetate (100 ml), and filtrated. The filtrate was evaporated to give a residue, which was subjected to column chromatography (silica-gel H:300-400 mesh; petroleum ether/ethyl acetate=5:1 v/v) to yield 3.6 g of a yellow jelly-like liquid.

In a 250 ml single-necked flask, to a stirred solution of above-described product (2.2 g, 4.67 mmol) in acetonitrile (60 ml) were added ethyl 2-bromo-isopropionate (2 ml, 13.5 mmol) and potassium carbonate (K$_2$CO$_3$) (1.5 g, 10.8 mmol). The reaction mixture was heated to reflux for 36 hours. After the reaction was completed, the reaction mixture was diluted with ethyl acetate (100 ml), and filtrated. The filtrate was evaporated to give a residue, which was purified by column chromatography (silica-gel H:300-400 mesh; petroleum ether/ethyl acetate=5:1 v/v) to yield 1.0 g of E-16 (yellow gelatinoids, three-step yield: 44%).

Its structure was characterized by the following data from nuclear magnetic resonance spectroscopy and Mass spectroscopy:

$^1$H NMR (400 MHz, CDCl$_3$) δ 1.20 (t, J=7.14 Hz, 3H), 1.55 (d, J=5.76 Hz, 6H), 2.13 (s, 3H), 3.15 (s, 3H), 4.18 (q, J=7.14 Hz, 2H), 5.19 (s, 1H), 6.49 (d, J=8.46 Hz, 1H), 7.03 (dd, J=8.46 Hz, 2.36 Hz, 1H), 7.16 (d, J=2.36 Hz, 1H), 7.32-7.37 (m, 5H), 7.66 (d, J=8.74 Hz, 2H), 8.10 (d, J=8.74 Hz, 2H); MS (ESI) m/z 586.39 (M+H$^+$).

Example 26

Preparation of the Compound E-17

Using the compounds III-2 and II-4 as starting materials, ethyl 2-(3-methyl-4-(1-(3-(4-n-butyl-5-oxo-1-(4-trifluoromethyl-phenyl)-4,5-dihydrogen-1H-1,2,4-triazolyl))-benzyloxy)-phenylthio)-acetate (E-17) was prepared according to a chemical reaction process similar to that described in Example 9. It is a pale-yellow solid with a yield of 81.2%.

Its structure was characterized by the following data from nuclear magnetic resonance spectroscopy and Mass spectroscopy:

$^1$H NMR (400 MHz, CDCl$_3$) δ 0.76 (t, J=7.30 Hz, 3H), 0.92-1.02 (m, 1H), 1.03-1.29 (m, 5H), 1.35-1.48 (m, 1H), 2.37 (s, 3H), 3.47-3.56 (m, 3H), 3.63-3.67 (m, 1H), 4.11-4.16 (m, 2H), 6.38 (s, 1H), 6.97 (d, J=8.59 Hz, 1H), 7.24 (dd, J=8.57 Hz, 2.25 Hz, 1H), 7.34 (d, J=2.04 Hz, 1H), 7.39-7.52 (m, 5H), 7.69 (d, J=8.73 Hz, 2H), 8.19 (d, J=8.56 Hz, 2H); $^{13}$C NMR (100 MHz, CDCl$_3$) δ 13.5, 14.1, 16.5, 19.9, 30.1, 38.0, 42.4, 61.4, 74.7, 113.1, 118.2, 125.6, 126.2, 126.3, 128.0, 128.9, 129.1, 130.8, 134.9, 135.3, 140.5, 145.9, 152.6, 155.0, 169.8; MS (ESI) m/z 600.0 (M)$^+$, 601.2 (M+1)$^+$, 602.2 (M+2)$^+$, 603.2 (M+3)$^+$.

Example 27

Preparation of the Compound E-18

Preparation of ethyl 2,2-dimethyl-2-(3-methyl-4-(1-(2-(4-n-butyl-5-oxo-1-(4-trifluoromethyl-phenyl)-4,5-dihydrogen-1H-1,2,4-triazolyl))-benzylthio)-phenoxy)-acetate (E-18)

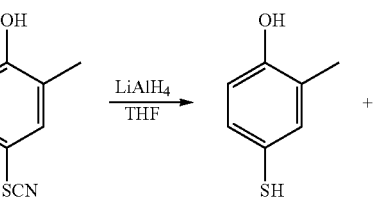

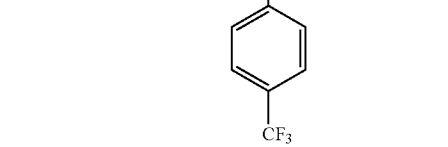

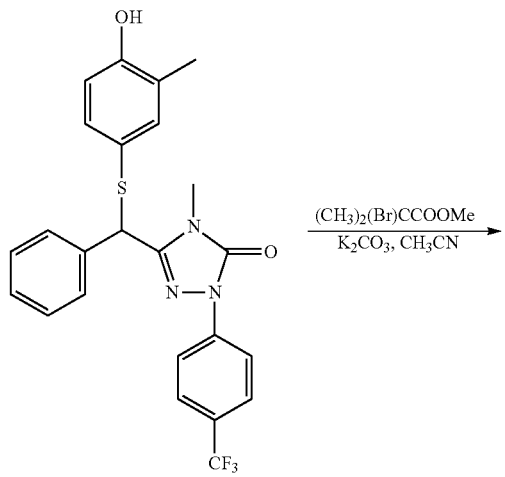

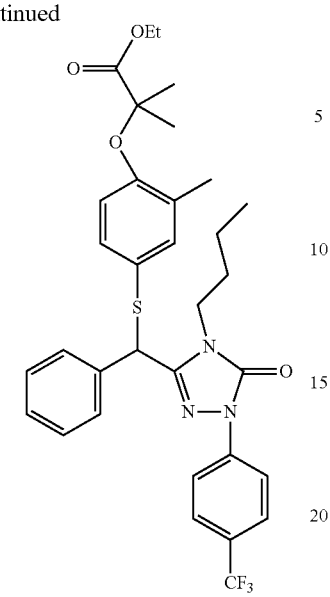

In a 250 ml three-necked flask, to a stirred mixture of lithium aluminum tetrahydride (LiAlH$_4$, 1.2 g, 31.6 mmol) and tetrahydrofuran (50 ml) was added dropwise a solution of 3-methyl-4-hydroxy-phenyl thiocyanic acid (1.4 g, 8.47 mmol) in tetrahydrofuran (20 ml) at 0° C. After 30 min of stirring at 0° C., the mixture was allowed to warm up to room temperature and then stirred for another 2 hours at room temperature. The reaction was quenched by adding ethanol (10 ml). The value of pH of the mixture was adjusted to 3-4 by adding 6 N hydrochloric acid in an ice water bath, and then the aqueous phase was extracted with ethyl acetate (3×100 ml). The combined organic layer was dried over anhydrous magnesium sulfate, filtrated, and evaporated in vacuo to yield a yellow liquid.

In a 250 ml single-necked flask, to a stirred solution of the resulting yellow liquid in acetonitrile (60 ml) were added bromide 111-2 (1.4 g, 3.08 mmol) and potassium carbonate (K$_2$CO$_3$, 0.42 g, 3.04 mmol). After the mixture was stirred for 6 hours at room temperature, ethyl 2-bromo-isopropionate (6 ml, 40.5 mmol) in acetonitrile (10 ml) and potassium carbonate (K$_2$CO$_3$, 2.4 g, 17.4 mmol) were added thereinto. The mixture was heated to reflux for 36 hours. After the reaction was completed, the reaction mixture was diluted with ethyl acetate (100 ml), and filtrated. The filtrate was evaporated to give a residue, which was subjected to column chromatography (silica-gel H:300-400 mesh; petroleum ether/ethyl acetate=10:1 v/v) to yield 1.52 g of E-18 (a yellow gelatinoid, three-steps yield: 28.6%).

Its structure was characterized by the following data from nuclear magnetic resonance spectroscopy and Mass spectroscopy:

$^1$H NMR (400 MHz, CDCl$_3$) δ 0.80 (t, J=7.30 Hz, 3H), 1.16-1.36 (m, 7H), 1.56 (d, J=2.84 Hz, 6H), 2.12 (s, 3H), 3.48-3.57 (m, 2H), 4.17-4.23 (m, 2H), 5.10 (s, 1H), 6.48 (d, J=8.44 Hz, 1H), 7.01 (dd, J=8.46 Hz, 2.28 Hz, 1H), 7.17 (d, J=2.08 Hz, 1H), 7.30-7.35 (m, 5H), 7.67 (d, J=8.81 Hz, 2H), 8.15 (d, J=8.66 Hz, 2H); $^{13}$C NMR (100 MHz, CDCl$_3$) δ 13.5, 14.0, 16.5, 19.8, 25.3, 29.7, 30.4, 41.9, 50.3, 61.5, 79.2, 116.4, 118.1, 124.5, 126.1, 128.4, 128.5, 128.8, 130.3, 133.3, 135.9, 137.8, 140.6, 146.4, 152.3, 154.9, 174.1; MS (ESI) m/z 626.1 (M−2)$^−$, 627.1 (M−1)$^−$ 628.1 (M)$^−$.

Example 28

Preparation of the Compound E-19

Preparation of Ethyl 2-(2,5-dimethyl-4-(1-(3-(4-n-butyl-5-oxo-1-(4-trifluoromethyl-phenyl)-4,5-dihydrogen-1H-1,2,4-triazolyl))-benzylthio)-phenoxy)-acetate (E-19)

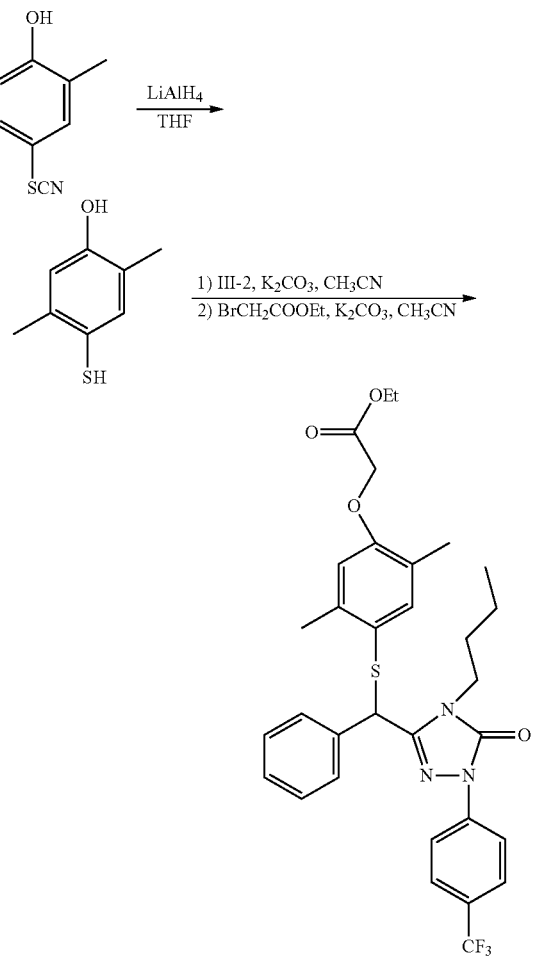

In a 250 ml three-necked flask, to a stirred mixture of lithium aluminum tetrahydride (LiAlH$_4$, 1.0 g, 26.3 mmol) and tetrahydrofuran (40 ml) was added dropwise a solution of 2,5-dimethyl-4-hydroxy-phenyl thiocyanic acid (1.02 g, 5.69 mmol) in tetrahydrofuran (20 ml) at 0° C. After 30 min of stirring at 0° C., the mixture was allowed to warm up to room temperature and then stirred for another 1 hour at room temperature. The reaction was quenched by adding ethanol (10 ml). The value of pH of the mixture was adjusted to 3-4 by adding 6 M hydrochloric acid in an ice water bath, and then the aqueous phase was extracted with ethyl acetate (3×60 ml). The combined organic layer was dried over anhydrous magnesium sulfate, filtrated, and evaporated in vacuo to yield a crude product of 2,5-dimethyl-4-hydroxy-mercaptobebzene (yellow liquid).

In a 250 ml single-necked flask, to a stirred solution of the resulting crude product of 2,5-dimethyl-4-hydroxy-mercaptobebzene in acetonitrile (60 ml) were added 3-(1'-bromobenzyl)-4-n-butyl-1-(4-trifluoromethyl)phenyl-1H-1,2,4-triazole-5(4H)-one III-2 (1.1 g, 2.42 mmol) and potassium carbonate ($K_2CO_3$, 0.35 g, 2.35 mmol). After the mixture was stirred for 4 hours at room temperature, ethyl bromoacetate (1.8 ml, 15.5 mmol) and potassium carbonate ($K_2CO_3$, 1.5 g, 10.8 mmol) were added thereinto, and then the reaction mixture was stirred overnight at room temperature. After the reaction was completed, the reaction mixture was diluted with ethyl acetate (200 ml), and filtrated. The filtrate was evaporated in vacuo to give a residue, which was subjected to column chromatography (silica-gel H:300-400 mesh; petroleum ether/ethyl acetate=8:1 v/v) to yield 0.8 g of E-19 (a yellow gelatinoid, three-step yield: 22.9%).

Its structure was characterized by the following data from nuclear magnetic resonance spectroscopy:

$^1$H NMR (400 MHz, CDCl$_3$) δ 0.80 (t, J=7.26 Hz, 3H), 1.18-1.33 (m, 7H), 2.13 (s, 3H), 2.22 (s, 3H), 3.50-3.52 (m, 2H), 4.23-4.29 (m, 2H), 4.59 (s, 2H), 5.01 (s, 1H), 6.50 (s, 1H), 7.13 (s, 1H), 7.30-7.32 (m, 5H), 7.68 (d, J=8.64 Hz, 2H), 8.16 (d, J=8.52 Hz, 2H); $^{13}$C NMR (100 MHz, CDCl$_3$) δ 13.5, 14.2, 15.5, 19.8, 20.8, 29.7, 30.4, 41.8, 49.7, 61.4, 65.5, 112.7, 118.1, 122.7, 125.8, 126.2, 128.3, 128.4, 128.8, 135.9, 139.0, 140.6, 141.6, 146.5, 152.3, 156.9, 168.7.

Preparation of the Compound (I) (Acid)

Example 29

Preparation of the Compound A-1

Preparation of 2-(2-methyl-4-(1-(3-(4-methyl-5-oxo-1-(4-trifluoromethyl-phenyl)-4,5-dihydrogen-1H-1,2,4-triazolyl))-benzyloxy)-phenoxy)-acetic acid (A-1)

To a stirred solution of ethyl 2-(2-methyl-4-(1-(3-(4-methyl-5-oxo-1-(4-trifluoromethyl-phenyl)-4,5-dihydrogen-1H-1,2,4-triazolyl))-benzyloxy)-phenoxy-acetate (28 g, 51.8 mmol) in dichloromethane (50 ml) and ethanol (50 ml) was added a 50 ml aqueous solution of sodium hydroxide (10 g, 250 mmol). The reaction mixture was stirred for 12 hours at room temperature. After the reaction was completed, the value of pH of the mixture was adjusted to 2-3 by adding 6 N hydrochloric acid. The resulting mixture was extracted with dichloromethane (3×100 ml). The combined organic layer was dried over anhydrous magnesium sulfate, filtrated, and evaporated to give a residue. The residue was purified by column chromatography (silica-gel H: 300-400 mesh; petroleum ether/ethyl acetate=4:1→1:1 v/v) to yield 18.2 g of A-1 as a white solid (yield: 68.5%).

Its structure was characterized by the following data from nuclear magnetic resonance spectroscopy and Mass spectroscopy:

$^1$H NMR (400 MHz, CDCl$_3$) δ 2.29 (s, 3H), 3.25 (s, 3H), 4.62 (s, 2H), 6.32 (s, 1H), 6.69 (d, J=8.8 Hz, 1H), 6.86 (d, J=8.75 Hz, 1H), 6.98 (s, 1H), 7.43-7.50 (m, 3H), 7.55-7.58 (m, 2H), 7.72 (d, J=8.48 Hz, 2H), 8.19 (d, J=8.48 Hz, 2H); $^{13}$C NMR (100 MHz, CDCl$_3$) δ 16.4, 18.1, 28.3, 58.4, 65.9, 75.3, 112.8, 113.2, 118.3, 119.3, 122.7, 125.8, 126.2, 127.1, 128.9, 129.0, 129.4, 135.1, 140.4, 146.3, 151.5, 152.8, 173.2; MS (ESI) m/z 514.2 (M+H$^+$); 531 (M+NH$_4^+$).

Example 30

Preparation of the Compound A-2

Using the compound E-2 as a starting material, 2-(2-methyl-4-(1-(3-(4-methyl-5-oxo-1-(4-trifluoromethyl-phenyl)-4,5-dihydrogen-1H-1,2,4-triazolyl))-benzyloxy)-phenylthio)-acetic acid (A-2) was prepared according to a synthesis process similar to that described in Example 29. It is a pale-yellow solid with a yield of 46%.

Its structure was characterized by the following data from nuclear magnetic resonance spectroscopy and Mass spectroscopy:

$^1$H NMR (400 MHz, CDCl$_3$) δ 2.42 (s, 3H), 3.18 (s, 3H), 3.51 (s, 2H), 6.76 (s, 1H), 6.90 (d, J=8.4 Hz, 1H), 6.98 (d, J=2.76 Hz, 1H), 7.25-7.52 (m, 5H), 7.67 (d, J=8.67 Hz, 2H), 8.14 (d, J=8.58 Hz, 2H); $^{13}$C NMR (100 MHz, CDCl$_3$) δ 20.9, 28.3, 36.9, 74.6, 113.7, 118.0, 118.3, 125.8, 126.2, 126.3, 126.6, 127.1, 128.98, 129.01, 134.1, 134.6, 140.4, 142.2, 145.9, 152.6, 156.8, 174.6; MS (ESI) m/z 528 (M−H)$^-$; 529 (M$^-$); 530 1 (M+H)$^-$.

Example 31

Preparation of the Compound A-3

Using the compound E-3 as a starting material, 2-(3-methyl-4-(1-(3-(4-methyl-5-oxo-1-(4-trifluoromethyl-phenyl)-4,5-dihydrogen-1H-1,2,4-tri azolyl))-benzyloxy)-phenylthio)-acetic acid (A-3) was prepared according to a synthesis process similar to that described in Example 29. It is a white solid with a yield of 24.2%.

Its structure was characterized by the following data from nuclear magnetic resonance spectroscopy and Mass spectroscopy:

$^1$H NMR (400 MHz, CDCl$_3$) δ 2.41 (s, 3H), 3.24 (s, 3H), 3.61 (s, 2H), 6.43 (s, 1H), 6.99 (d, J=8.58 Hz, 1H), 7.22-7.29 (m, 1H), 7.38 (d, J=2.28 Hz, 1H), 7.38-7.56 (m, 5H), 7.73 (d, J=8.68 Hz, 2H), 8.21 (d, J=8.68 Hz, 2H); $^{13}$C NMR (100 MHz, CDCl$_3$) δ 16.5, 28.2, 37.8, 74.5, 113.2, 118.2, 125.7, 126.2, 126.6, 127.1, 128.2, 128.99, 129.1, 130.8, 134.7, 140.4, 145.9, 152.7, 155.0, 174.2; MS (ESI) m/z 556.9 (M+CO)$^+$.

Example 32

Preparation of the Compound A-4

Using the compound E-4 as a starting material, 2-(2-methyl-4-(1-(3-(4-methyl-5-oxo-1-(4-trifluoromethyl-phenyl)-4,5-dihydrogen-1H-1,2,4-tri azolyl))-benzylthio)-phenoxy)-acetic acid (A-4) was prepared according to a synthesis process similar to that described in Example 29. It is a white solid with a yield of 52.9%.

Its structure was characterized by the following data from nuclear magnetic resonance spectroscopy and Mass spectroscopy:

$^1$H NMR (400 MHz, CDCl$_3$) δ 2.18 (s, 3H), 3.13, (s, 3H), 4.63 (s, 2H), 5.19 (s, 1H), 6.57 (d, J=8.43 Hz, 1H), 7.13 (dd, J=6.07 Hz, 2.26 Hz, 1H), 7.18 (d, J=1.8 Hz, 1H), 7.32-7.36 (m, 5H), 7.66 (d, J=8.73 Hz, 2H), 8.10 (d, J=8.69 Hz, 2H); $^{13}$C NMR (100 MHz, CDCl$_3$) δ 16.0, 28.1, 50.5, 64.9, 111.5, 118.3, 123.6, 126.1, 126.2, 128.2, 128.4, 128.6, 128.9, 133.9, 135.0, 137.8, 140.4, 146.5, 152.6, 156.7, 172.6; MS (ESI) m/z 530 (M+H)$^+$, 531 (M+2), 532 (M+3).

Example 33

Preparation of the Compound A-5

Using the compound E-5 as a starting material, 2-(2-ethyl-4-(1-(3-(4-methyl-5-oxo-1-(4-trifluoromethyl-phenyl)-4,5-dihydrogen-1H-1,2,4-triazolyl))-benzyloxy)-phenoxy)-acetic acid (A-5) was prepared according to a synthesis process similar to that described in Example 29. It is a white solid with a yield of 62.8%.

Its structure was characterized by the following data from nuclear magnetic resonance spectroscopy and Mass spectroscopy:

$^1$H NMR (400 MHz, CDCl$_3$) δ 1.19 (t, J=7.55 Hz, 3H), 2.66 (q, J=7.51 Hz, 2H), 3.19 (s, 3H), 4.62 (s, 2H), 6.29 (s, 1H), 6.66 (d, J=8.88 Hz, 1H), 6.83 (dd, J=8.87 Hz, 3.09 Hz, 1H), 6.96 (d, J=3.09 Hz, 1H), 7.38-7.53 (m, 5H), 7.67 (d, J=8.85 Hz, 2H), 8.15 (d, J=8.78 Hz, 2H); $^{13}$C NMR (100 MHz, CDCl$_3$) δ 13.9, 23.2, 28.3, 65.7, 75.2, 112.6, 113.0, 117.7, 118.2, 125.8, 126.2, 127.0, 127.4, 128.8, 129.01, 135.1, 135.2, 140.4, 146.3, 150.9, 151.8, 152.8, 173.3; MS (ESI) m/z 525.9 (M−1)$^-$, 527 (M)$^-$, 528 (M+1)$^-$.

Example 34

Preparation of the Compound A-6

Using the compound E-6 as a starting material, 2-(3-methyl-4-(1-(3-(4-methyl-5-oxo-1-(4-trifluoromethyl-phenyl)-4,5-dihydrogen-1H-1,2,4-tri azolyl))-benzyloxy)-phenoxy)-acetic acid (A-6) was prepared according to a synthesis process similar to that described in Example 29. It is a pale-yellow solid with a yield of 42.4%.

Its structure was characterized by the following data from nuclear magnetic resonance spectroscopy and Mass spectroscopy:

$^1$H NMR (400 MHz, CDCl$_3$) δ 2.40 (s, 3H), 3.25 (s, 3H), 4.65 (s, 3H), 6.34 (s, 1H), 6.69 (d d, J=8.86 Hz, 3.0 Hz, 1H), 6.88 (d, J=3.0 Hz, 1H), 6.95 (d, J=8.88 Hz, 2H), 7.43-7.58 (m, 5H), 7.73 (d, J=8.63 Hz, 2H), 8.21 (d, J=8.58 Hz, 2H); $^{13}$C NMR (100 MHz, CDCl$_3$) δ 16.8, 28.3, 65.4, 75.1, 112.2, 113.8, 118.3, 118.5, 125.7, 126.2, 126.3, 127.1, 128.9, 129.1, 135.1, 140.4, 146.3, 150.2, 152.4, 152.8, 173.1; MS (ESI) m/z 513 (M)$^-$, 512 (M−1)$^-$, 514 (M+1)$^-$.

Example 35

Preparation of the Compound A-7

Using the compound E-7 as a starting material, 2-(3-methyl-4-(1-(3-(4-methyl-5-oxo-1-(4-trifluoromethyl-phenyl)-4,5-dihydrogen-1H-1,2,4-tri azolyl))-benzylthio)-phenoxy)-acetic acid (A-7) was prepared according to a synthesis process similar to that described in Example 29. It is a pale-yellow solid with a yield of 42%.

Its structure was characterized by the following data from nuclear magnetic resonance spectroscopy and Mass spectroscopy:

$^1$H NMR (400 MHz, CDCl$_3$) δ 2.33 (s, 3H), 3.11 (s, 3H), 4.65 (s, 2H), 5.11 (s, 1H), 6.62 (dd, J=8.53 Hz, 2.88 Hz, 1H), 6.78 (d, J=2.88 Hz, 1H), 7.27-7.34 (m, 5H), 7.66 (d, J=8.79 Hz, 2H), 8.09 (d, J=8.71 Hz, 2H); $^{13}$C NMR (100 MHz, CDCl$_3$) δ 21.0, 28.1, 49.7, 64.6, 112.6, 116.9, 118.3, 123.1, 126.2, 128.1, 128.6, 129.0, 135.0, 137.9, 140.4, 144.6, 146.5, 152.6, 158.3, 172.1; MS (ESI) m/z 530 (M)$^+$, 531 (M+1)$^+$.

Example 36

Preparation of the Compound A-8

Using the compound E-8 as a starting material, 2-(2-methyl-4-(3-(4-methyl-5-oxo-1-(4-trifluoromethyl-phenyl)-4,5-dihydrogen-1H-1,2,4-triazolyl)-methylthio)-phenoxy)-acetic acid (A-8) was prepared according to a synthesis process similar to that described in Example 29. It is a white solid with a yield of 76%.

Its structure was characterized by the following data from nuclear magnetic resonance spectroscopy and Mass spectroscopy:

$^1$H NMR (400 MHz, DMSO) δ 2.11 (s, 3H), 3.3 (s, 3H), 4.13 (s, 2H), 4.68 (s, 2H), 6.80 (d, J=8.13 Hz, 1H), 7.25-7.27 (m, 2H), 7.80 (d, J=8.85 Hz, 2H), 7.99 (d, J=8.68 Hz, 2H); $^{13}$C NMR (100 MHz, DMSO) δ 16.2, 28.0, 30.4, 62.5, 65.3, 112.5, 118.1, 120.6, 123.3, 123.6, 123.9, 124.9, 125.2, 125.6, 125.9, 126.8, 127.5, 128.7, 132.1, 135.6, 141.1, 146.3, 152.3, 156.6, 170.5; MS (ESI) m/z 452.8 (M).

Example 37

Preparation of the Compound A-9

Using the compound E-9 as a starting material, 2-(2-methyl-4-(3-(4-methyl-5-oxo-1-(4-trifluoromethyl-phenyl)-4,5-dihydrogen-1H-1,2,4-triazolyl)-methoxy)-phenoxy)-acetic acid (A-9) was prepared according to a synthesis process similar to that described in Example 29. It is a white solid with a yield of 69.2%.

Its structure was characterized by the following data from nuclear magnetic resonance spectroscopy and Mass spectroscopy:

$^1$H NMR (400 MHz, CDCl$_3$) δ 2.28 (s, 3H), 3.43 (s, 3H), 4.64 (s, 2H), 4.99 (s, 2H), 6.69 (d, J=8.40 Hz, 1H), 6.78 (dd, J=8.82 Hz, 3.06 Hz, 1H), 6.85 (dd, J=2.96 Hz, 1H), 7.67 (d, J=8.60 Hz, 2H), 8.13 (d, J=8.55 Hz, 2H); $^{13}$C NMR (100 MHz, CDCl$_3$) δ 16.4, 28.1, 61.9, 65.9, 112.1, 112.8, 118.2, 118.3, 118.4, 126.2, 126.3, 129.3, 143.9, 151.2, 152.0, 152.5, 170.4; MS (ESI) m/z 436 (M−1), 437 (M), 438 (M+1).

Example 38

Preparation of the Compound A-10

Using the compound E-10 as a starting material, 2-(2,5-dimethyl-4-(1-(3-(4-methyl-5-oxo-1-(4-trifluoromethyl-phenyl)-4,5-dihydrogen-1H-1,2,4-triazolyl))-benzylthio)-phenoxy)-acetic acid (A-10) was prepared according to a synthesis process similar to that described in Example 29. It is a white solid with a yield of 88.9%.

Its structure was characterized by the following data from nuclear magnetic resonance spectroscopy and Mass spectroscopy:

$^1$H NMR (400 MHz, CDCl$_3$) δ 2.09 (s, 3H), 2.25 (s, 3H), 3.09 (s, 3H), 4.59 (s, 2H), 5.09 (s, 1H), 6.52 (s. 1H), 7.13 (s, 1H), 7.31-7.37 (m, 5H), 7.65 (d, J=8.70 Hz, 2H), 8.09 (d, J=8.70 Hz, 2H); $^{13}$C NMR (100 MHz, CDCl$_3$) δ 15.4, 20.7, 28.0, 49.7, 65.2, 113.2, 118.4, 122.7, 126.2, 126.7, 128.2, 128.5, 128.9, 135.1, 139.0, 140.4, 141.6, 146.7, 152.6, 156.8, 173.0; MS (ESI) m/z 542.42 (M−1)$^-$, 543.54 (M)$^-$, 544.43 (M+H)$^-$.

Example 39

Preparation of the Compound A-11

Using the compound E-11 as a starting material, 2-(2,5-dimethyl-4-(1-(3-(4-methyl-5-oxo-1-(4-trifluoromethyl-phenyl)-4,5-dihydrogen-1H-1,2,4-triazolyl))-benzyloxy)-phenthio)-acetic acid (A-11) was prepared according to a synthesis process similar to that described in Example 29. It is a white solid with a yield of 70.8%.

Its structure was characterized by the following data from nuclear magnetic resonance spectroscopy and Mass spectroscopy:

$^1$H NMR (400 MHz, CDCl$_3$) δ 2.32 (s, 3H), 2.37 (s, 3H), 3.18 (s, 3H), 3.51 (s, 2H), 6.39 (s. 1H), 6.88 (s, 1H), 7.31 (s, 1H), 7.39-7.52 (m, 5H), 7.69 (d, J=8.67 Hz, 2H), 8.16 (d, J=8.67 Hz, 2H); $^{13}$C NMR (100 MHz, CDCl$_3$) δ 16.0, 20.7, 28.2, 37.2, 74.4, 114.7, 118.2, 125.4, 125.6, 125.7, 126.3, 128.9, 129.1, 134.9, 135.7, 139.5, 140.4, 146.1, 152.7, 155.0, 174.7; MS (ESI) m/z 541.96 (M−1)$^-$, 543.04 (M)$^-$, 544.07 (M+H)$^-$.

Example 40

Preparation of the Compound A-12

Using the compound E-12 as a starting material, 2-(3-methyl-4-(3-(4-methyl-5-oxo-1-(4-trifluoromethyl-phenyl)-4,5-dihydrogen-1H-1,2,4-triazolyl)-methoxy)-phenylthio)-acetic acid (A-12) was prepared according to a synthesis process similar to that described in Example 29. It is a white solid with a yield of 47.9%.

Its structure was characterized by the following data from nuclear magnetic resonance spectroscopy and Mass spectroscopy:

$^1$H NMR (400 MHz, CDCl$_3$) δ 2.19 (s, 3H), 3.43 (s, 3H), 3.55 (s, 2H), 5.03 (s, 2H), 6.91 (d, J=8.77 Hz, 3H), 7.29-7.32 (m, 2H), 7.67 (d, J=8.66 Hz, 2H), 8.12 (d, J=8.66 Hz, 2H); $^{13}$C NMR (100 MHz, CDCl$_3$) δ 16.1, 28.1, 38.1, 61.4, 111.8, 118.3, 126.2, 126.3, 127.2, 127.5, 127.9, 130.8, 134.8, 140.3, 143.6, 152.5, 155.4, 174.8; MS (ESI) m/z 452.23 (M−1)$^-$, 453.34 (M)$^-$, 454.35 (M+H)$^-$.

Example 41

Preparation of the Compound A-13

Using the compound E-13 as a starting material, 2-methyl-2-(2-methyl-4-(1-(3-(4-methyl-5-oxo-1-(4-trifluoromethyl-phenyl)-4,5-dihydrogen-1H-1,2,4-triazolyl))-benzylthio)-phenoxy)-acetic acid (A-13) was prepared according to a synthesis process similar to that described in Example 29. It is a white solid with a yield of 76.9%.

Its structure was characterized by the following data from nuclear magnetic resonance spectroscopy and Mass spectroscopy:

$^1$H NMR (400 MHz, CDCl$_3$) δ 1.55 (d, J=6.56 Hz, 3H), 2.12 (s, 3H), 3.06 (s, 3H), 4.62 (q, J=6.56 Hz, 1H), 5.17 (s, 1H), 6.56 (d, J=9.04 Hz, 1H), 7.14-7.17 (m, 2H), 7.31-7.38 (m, 5H), 7.65 (d, J=8.68 Hz, 2H), 8.09 (d, J=8.68 Hz, 2H); MS (ESI) m/z 542.24 (M−1)$^-$, 543.26 (M)$^-$, 544.24 (M+H)$^-$.

Example 42

Preparation of the Compound A-14

Using the compound E-14 as a starting material, 2-(2-ethyl-4-(1-(3-(4-methyl-5-oxo-1-(4-trifluoromethyl-phenyl)-4,5-dihydrogen-1H-1,2,4-triazolyl))-benzylthio)-phenoxy)-acetic acid (A-14) was prepared according to a synthesis process similar to that described in Example 29. It is a white solid with a yield of 63.1%.

Its structure was characterized by the following data from nuclear magnetic resonance spectroscopy and Mass spectroscopy:

$^1$H NMR (400 MHz, CDCl$_3$) δ 1.07 (t, J=7.56 Hz, 3H), 2.56 (q, J=7.56 Hz, 2H), 3.09 (s, 3H), 4.59 (s, 2H), 5.18 (s, 1H), 6.56 (d, J=9.04 Hz, 1H), 7.14-7.17 (m, 2H), 7.31-7.38 (m, 5H), 7.65 (d, J=8.68 Hz, 2H), 8.09 (d, J=8.68 Hz, 2H); $^{13}$C NMR (100 MHz, CDCl$_3$) δ 13.7, 22.9, 28.0, 50.4, 65.0, 111.6, 118.3, 123.6, 125.4, 126.1, 126.2, 127.3, 127.5, 128.3, 128.5, 128.9, 133.9, 134.2, 135.1, 136.3, 140.4, 146.6, 152.5, 156.4, 172.7; MS (ESI) m/z 544.14 (M+H)$^+$, 561.93 (M+NH$_4$)$^+$.

Example 43

Preparation of the Compound A-15

Using the compound E-15 as a starting material, 2,2-dimethyl-2-(3-methyl-4-(1-(3-(4-methyl-5-oxo-1-(4-trifluoromethyl-phenyl)-4,5-dihydrogen-1H-1,2,4-triazolyl))-benzyloxy)-phenylthio)-acetic acid (A-15) was prepared according to a synthesis process similar to that described in Example 29. It is a white solid with a yield of 70.6%.

Its structure was characterized by the following data from nuclear magnetic resonance spectroscopy and Mass spectroscopy:

$^1$H NMR (400 MHz, CDCl$_3$) δ 1.46 (s, 6H), 2.35 (s, 3H), 3.18 (s, 3H), 6.40 (s, 1H), 6.96 (d, J=8.56 Hz, 1H), 7.26-7.27 (m, 1H), 7.35-7.50 (m, 6H), 7.67 (d, J=8.72 Hz, 2H), 8.15 (d, J=8.64 Hz, 2H); $^{13}$C NMR (100 MHz, CDCl$_3$) δ 16.4, 25.4, 28.2, 50.7, 74.5, 112.6, 118.2, 123.7, 125.7, 126.2, 127.4, 128.1, 128.9, 129.1, 134.7, 136.1, 139.8, 140.4, 145.9, 152.6, 156.4, 179.1; MS (ESI) m/z 556.69 (M)$^+$, 558.04 (M+1)$^+$.

Example 44

Preparation of the Compound A-16

Using the compound E-16 as a starting material, 2,2-dimethyl-2-(2-methyl-4-(1-(3-(4-methyl-5-oxo-1-(4-trifluoromethyl-phenyl)-4,5-dihydrogen-1H-1,2,4-triazolyl))-benzylthio)-phenoxy)-acetic acid (A-16) was prepared according to a synthesis process similar to that described in Example 29. It is a white solid with a yield of 52.6%.

Its structure was characterized by the following data from nuclear magnetic resonance spectroscopy and Mass spectroscopy:

$^1$H NMR (400 MHz, CDCl$_3$) δ 1.57 (d, J=5.25 Hz, 6H), 2.12 (s, 3H), 3.10 (s, 3H), 5.21 (s, 2H), 6.63 (d, J=8.47 Hz, 1H), 7.05 (dd, J=8.47 Hz, 2.06 Hz, 1H), 7.19 (d, J=1.99 Hz, 1H), 7.25-7.37 (m, 5H), 7.65 (d, J=8.76 Hz, 2H), 8.09 (d, J=8.62 Hz, 2H); $^{13}$C NMR (100 MHz, CDCl$_3$) δ 16.6, 25.1, 25.3, 28.1, 50.3, 79.4, 117.3, 118.3, 124.1, 126.2, 126.3, 128.2, 128.5, 128.9, 130.8, 133.2, 134.9, 137.8, 140.4, 146.6, 152.6, 154.5, 177.4; MS (ESI) m/z 558.06 (M)$^+$.

Example 45

Preparation of the Compound A-17

Using the compound E-17 as a starting material, 2-(3-methyl-4-(1-(3-(4-n-butyl-5-oxo-1-(4-trifluoromethyl-phenyl)-4,5-dihydrogen-1H-1,2,4-tri azolyl))-benzyloxy)-phenylthio)-acetic acid (A-17) was prepared according to a synthesis process similar to that described in Example 29. It is a white solid with a yield of 62%.

Its structure was characterized by the following data from nuclear magnetic resonance spectroscopy and Mass spectroscopy:

¹H NMR (400 MHz, CDCl₃) δ 0.75 (t, J=7.29 Hz, 3H), 1.03-1.05 (m, 1H), 1.11-1.18 (m, 2H), 1.19-1.26 (m, 1H), 1.40-1.50 (m, 1H), 2.36 (s, 3H), 3.47-3.53 (m, 1H), 3.56 (s, 2H), 3.62-3.69 (m, 1H), 6.38 (s, 1H), 6.97 (d, J=8.58 Hz, 1H), 7.24 (dd, J=8.47 Hz, 1.92 Hz, 1H), 7.33 (d, J=1.99 Hz, 1H), 7.39-7.51 (m, 5H), 7.68 (d, J=8.74 Hz, 2H), 8.17 (d, J=8.61 Hz, 2H); ¹³C NMR (100 MHz, CDCl₃) δ 13.5, 16.6, 19.9, 37.8, 42.4, 74.7, 113.2, 118.2, 125.6, 126.2, 126.3, 128.2, 128.9, 129.1, 130.9, 134.8, 135.1, 140.4, 145.9, 152.6, 155.3, 174.4; MS (ESI) m/z 569.93 (M−2)⁻, 570.9 (M−1)⁻.

Example 46

Preparation of the Compound A-18

Using the compound E-18 as a starting material, 2,2-dimethyl-2-(2-methyl-4-(1-(3-(4-n-butyl-5-oxo-1-(4-trifluoromethyl-phenyl)-4,5-dihydrogen-1H-1,2,4-triazolyl))-benzylthio)-phenoxy)-acetic acid (A-18) was prepared according to a synthesis process similar to that described in Example 29. It is a white solid with a yield of 61.3%.

Its structure was characterized by the following data from nuclear magnetic resonance spectroscopy and Mass spectroscopy:

¹H NMR (400 MHz, CDCl₃) δ 0.79 (t, J=7.26 Hz, 3H), 1.17-1.32 (m, 6H), 1.59 (s, 6H), 2.13 (s, 3H), 3.48-3.53 (m, 2H), 5.13 (s, 1H), 6.63 (d, J=8.44 Hz, 1H), 7.05 (dd, J=8.47 Hz, 2.04 Hz, 1H), 7.17 (d, J=2.08 Hz, 1H), 7.31-7.35 (m, 5H), 7.67 (d, J=8.84 Hz, 2H), 8.14 (d, J=8.60 Hz, 2H); ¹³C NMR (100 MHz, CDCl₃) δ 13.5, 16.6, 19.8, 25.2, 25.3, 29.7, 30.4, 41.8, 50.1, 79.4, 117.3, 118.3, 124.4, 126.1, 128.4, 128.5, 128.8, 130.7, 133.4, 135.7, 137.9, 140.5, 146.5, 152.4, 154.5, 177.9; MS (ESI) m/z 597.96 (M−2)⁻, 599.0 (M−1)⁻ 600.0 (M)⁻.

Example 47

Preparation of the Compound A-19

Using the compound E-19 as a starting material, 2-(2,5-dimethyl-4-(1-(3-(4-n-butyl-5-oxo-1-(4-trifluoromethyl-phenyl)-4,5-dihydrogen-1H-1,2,4-triazolyl))-benzylthio)-phenoxy)-acetic acid (A-19) was prepared according to a synthesis process similar to that described in Example 29. It is a white solid with a yield of 31.4%.

Its structure was characterized by the following data from nuclear magnetic resonance spectroscopy and Mass spectroscopy:

¹H NMR (400 MHz, CDCl₃) δ 0.79 (t, J=7.27 Hz, 3H), 1.13-1.23 (m, 2H), 1.28-1.36 (m, 2H), 2.12 (s, 3H), 2.25 (s, 3H), 3.47-3.55 (m, 2H), 4.66 (s, 2H), 5.03 (s, 1H), 6.53 (s, 1H), 7.15 (s, 1H), 7.29-7.36 (m, 5H), 7.68 (d, J=8.66 Hz, 2H), 8.16 (d, J=8.56 Hz, 2H); ¹³C NMR (100 MHz, CDCl₃) δ 13.5, 15.5, 19.8, 20.8, 30.4, 41.9, 49.6, 64.9, 112.9, 118.3, 123.1, 125.7, 126.2, 128.3, 128.5, 128.8, 135.8, 139.1, 140.5, 141.7, 146.5, 152.4, 156.6, 173.2; MS (ESI) m/z 584.03 (M−1)⁻, 584.98 (M)⁻.

The invention claimed is:
1. Compound of formula (I) or its pharmaceutically acceptable salts or solvates thereof,

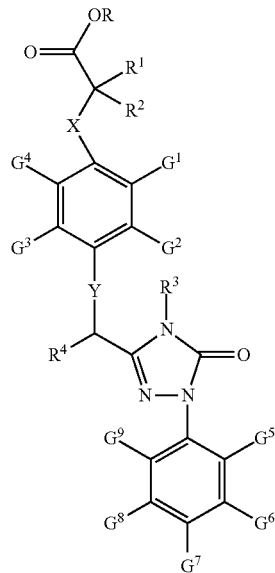

wherein,
X is O, S, NH or (CH₂)ₙ, in which n is an integer from 1 to 4;
Y is O, S or NH, wherein X and Y are not simultaneously O;
R is H or C1-C9 alkyl;
R¹ and R² are independently H or C1-C4 alkyl, and at least one of R¹ and R² is H;
R³ is H or C1-C9 alkyl;
R⁴ is phenyl or substituted phenyl; the substituent group on the phenyl is selected from the group consisting of C1-C9 alkyl, hydroxyl, C1-C9 alkoxy, mercapto, C1-C9 alkylthio, trifluoromethyl, F, Cl, Br, nitro, NR⁵R⁶, COOR⁵, NR⁵COR⁶ and CONR⁵R⁶;
G¹, G², G³, G⁴, G⁵, G⁶, G⁷, G⁸ and G⁹ are independently from each other or simultaneously H, C1-C9 alkyl, hydroxyl, C1-C9 alkoxy, mercapto, C1-C9 alkylthio, trifluoromethyl, F, Cl, Br, nitro, NR⁵R⁶, COOR⁵, NR⁵COR⁶ or CONR⁵R⁶; and
R⁵ and R⁶ are independently from each other or simultaneously H or C1-C9 alkyl.

2. The compound according to claim 1, wherein X is O, S or CH₂.
3. The compound according to claim 1, wherein Y is O or S.
4. The compound according to claim 1, wherein R is H, methyl or ethyl.
5. The compound according to claim 1, wherein le is H, methyl or ethyl.
6. The compound according to claim 1, wherein R² is H, methyl or ethyl.
7. The compound according to claim 1, wherein R³ is H or C1-C4 alkyl.
8. The compound according to claim 1, wherein R³ is methyl.
9. The compound according to claim 1, wherein, when R⁴ is substituted phenyl, the substituent group is selected from the group consisting of C1-C9 alkyl, hydroxyl, C1-C9 alkoxy, mercapto, C1-C9 alkylthio, trifluoromethyl, F, Cl, Br, nitro, $NR^5R^6$, $COOR^5$, $NR^5COR^6$ and $CONR^5R^6$; $R^5$ and $R^6$ are independently from each other or simultaneously H or C1-C9 alkyl.

10. The compound according to claim 1, wherein $G^1$, $G^2$, $G^3$, and $G^4$ are independently from each other or simultaneously H, C1-C9 alkyl, C1-C9 alkoxy, or C1-C9 alkylthio.

11. The compound according to claim 1, wherein $G^5$, $G^6$, $G^7$, $G^8$, and $G^9$ are independently from each other or simultaneously H, C1-C9 alkyl, C1-C9 alkoxy, trifluoromethyl, F, Cl, Br, nitro, $NR^5R^6$, $COOR^5$, $NR^5COR^6$, or $CONR^5R^6$; $R^5$ and $R^6$ are independently from each other or simultaneously H or C1-C9 alkyl.

12. The compound according to claim 1, wherein the compound is:
    Ethyl 2-(2-methyl-4-(1-(3-(4-methyl-5-oxo-1-(4-trifluoromethyl-phenyl)-4,5-dihydrogen-1H-1,2,4-triazolyl))-benzyloxy)-phenylthio)-acetate;
    Ethyl 2-(3-methyl-4-(1-(3-(4-methyl-5-oxo-1-(4-trifluoromethyl-phenyl)-4,5-dihydrogen-1H-1,2,4-triazolyl))-benzyloxy)-phenylthio)-acetate;
    Ethyl 2-(2-methyl-4-(1-(3-(4-methyl-5-oxo-1-(4-trifluoromethyl-phenyl)-4,5-dihydrogen-1H-1,2,4-triazolyl))-benzylthio)-phenoxy)-acetate;
    Ethyl 2-(3-methyl-4-(1-(3-(4-methyl-5-oxo-1-(4-trifluoromethyl-phenyl)-4,5-dihydrogen-1H-1,2,4-triazolyl))-benzylthio)-phenoxy)-acetate;
    Ethyl 2-(2,5-dimethyl-4-(1-(3-(4-methyl-5-oxo-1-(4-trifluoromethyl-phenyl)-4,5-dihydrogen-1H-1,2,4-triazolyl))-benzylthio)-phenoxy)-acetate;
    Ethyl 2-(2,5-dimethyl-4-(1-(3-(4-methyl-5-oxo-1-(4-trifluoromethyl-phenyl)-4,5-dihydrogen-1H-1,2,4-triazolyl))-benzyloxy)-phenylthio)-acetate;
    Methyl 2-methyl-2-(2-methyl-4-(1-(3-(4-methyl-5-oxo-1-(4-trifluoromethyl-phenyl)-4,5-dihydrogen-1H-1,2,4-triazolyl))-benzylthio)-phenoxy)-acetate;
    Ethyl 2-(2-ethyl-4-(1-(3-(4-methyl-5-oxo-1-(4-trifluoromethyl-phenyl)-4,5-dihydrogen-1H-1,2,4-triazolyl))-benzylthio)-phenoxy)-acetate;
    Ethyl 2,2-dimethyl-2-(3-methyl-4-(1-(3-(4-methyl-5-oxo-1-(4-trifluoromethyl-phenyl)-4,5-dihydrogen-1H-1,2,4-triazolyl))-benzyloxy)-phenylthio)-acetate;
    Ethyl 2,2-dimethyl-2-(2-methyl-4-(1-(3-(4-methyl-5-oxo-1-(4-trifluoromethyl-phenyl)-4,5-dihydrogen-1H-1,2,4-triazolyl))-benzylthio)-phenoxy)-acetate;
    Ethyl 2-(3-methyl-4-(1-(3-(4-n-butyl-5-oxo-1-(4-trifluoromethyl-phenyl)-4,5-dihydrogen-1H-1,2,4-triazolyl))-benzyloxy)-phenylthio)-acetate;
    Ethyl 2,2-dimethyl-2-(2-methyl-4-(1-(3-(4-n-butyl-5-oxo-1-(4-trifluoromethyl-phenyl)-4,5-dihydrogen-1H-1,2,4-triazolyl))-benzylthio)-phenoxy)-acetate;
    Ethyl 2-(2,5-dimethyl-4-(1-(3-(4-n-butyl-5-oxo-1-(4-trifluoromethyl-phenyl)-4,5-dihydrogen-1H-1,2,4-triazolyl))-benzylthio)-phenoxy)-acetate;
    2-(2-methyl-4-(1-(3-(4-methyl-5-oxo-1-(4-trifluoromethyl-phenyl)-4,5-dihydrogen-1H-1,2,4-triazolyl))-benzyloxy)-phenylthio)-acetic acid;
    2-(2-methyl-4-(1-(3-(4-methyl-5-oxo-1-(4-trifluoromethyl-phenyl)-4,5-dihydrogen-1H-1,2,4-triazolyl))-benzylthio)-phenoxy)-acetic acid;
    2-(3-methyl-4-(1-(3-(4-methyl-5-oxo-1-(4-trifluoromethyl-phenyl)-4,5-dihydrogen-1H-1,2,4-triazolyl))-benzyloxy)-phenylthio)-acetic acid;
    2-(3-methyl-4-(1-(3-(4-methyl-5-oxo-1-(4-trifluoromethyl-phenyl)-4,5-dihydrogen-1H-1,2,4-triazolyl))-benzylthio)-phenoxy)-acetic acid;
    2-(2,5-dimethyl-4-(1-(3-(4-methyl-5-oxo-1-(4-trifluoromethyl-phenyl)-4,5-dihydrogen-1H-1,2,4-triazolyl))-benzylthio)-phenoxy)-acetic acid;
    2-(2,5-dimethyl-4-(1-(3-(4-methyl-5-oxo-1-(4-trifluoromethyl-phenyl)-4,5-dihydrogen-1H-1,2,4-triazolyl))-benzyloxy)-phenylthio)-acetic acid;
    2-methyl-2-(2-methyl-4-(1-(3-(4-methyl-5-oxo-1-(4-trifluoromethyl-phenyl)-4,5-dihydrogen-1H-1,2,4-triazolyl))-benzylthio)-phenoxy)-acetic acid;
    2-(2-ethyl-4-(1-(3-(4-methyl-5-oxo-1-(4-trifluoromethyl-phenyl)-4,5-dihydrogen-1H-1,2,4-triazolyl))-benzylthio)-phenoxy)-acetic acid;
    2-(3-methyl-4-(1-(3-(4-n-butyl-5-oxo-1-(4-trifluoromethyl-phenyl)-4,5-dihydrogen-1H-1,2,4-triazolyl))-benzyloxy)-phenylthio)-acetic acid; or
    2-(2,5-dimethyl-4-(1-(3-(4-n-butyl-5-oxo-1-(4-trifluoromethyl-phenyl)-4,5-dihydrogen-1H-1,2,4-triazolyl))-benzylthio)-phenoxy)-acetic acid.

13. The compound according to claim 1, wherein the compound is:
    2-(2-methyl-4-(1-(3-(4-methyl-5-oxo-1-(4-trifluoromethyl-phenyl)-4,5-dihydrogen-1H-1,2,4-triazolyl))-benzylthio)-phenoxy)-acetic acid;
    2-(3-methyl-4-(1-(3-(4-methyl-5-oxo-1-(4-trifluoromethyl-phenyl)-4,5-dihydrogen-1H-1,2,4-triazolyl))-benzyloxy)-phenylthio)-acetic acid;
    2-(2,5-dimethyl-4-(1-(3-(4-methyl-5-oxo-1-(4-trifluoromethyl-phenyl)-4,5-dihydrogen-1H-1,2,4-triazolyl))-benzyloxy)-phenylthio)-acetic acid;
    2-(2-ethyl-4-(1-(3-(4-methyl-5-oxo-1-(4-trifluoromethyl-phenyl)-4,5-dihydrogen-1H-1,2,4-triazolyl))-benzylthio)-phenoxy)-acetic acid;
    2-(3-methyl-4-(1-(3-(4-n-butyl-5-oxo-1-(4-trifluoromethyl-phenyl)-4,5-dihydrogen-1H-1,2,4-triazolyl))-benzyloxy)-phenylthio)-acetic acid; or
    2-(2,5-dimethyl-4-(1-(3-(4-n-butyl-5-oxo-1-(4-trifluoromethyl-phenyl)-4,5-dihydrogen-1H-1,2,4-triazolyl))-benzylthio)-phenoxy)-acetic acid.

14. A pharmaceutical composition comprising the compound according to claim 1.

15. The pharmaceutical composition according to claim 14, the formulation form of which is selected from the group consisting of plain-tablets, film-coated tablets, dragees, enteric coated tablets, dispersible tablets, capsules, granulas, oral solutions and oral suspensions.

16. A method for the treatment of a disease that is treatable by activating peroxisome proliferator-activated receptor subtype δ (PPARδ), comprising administration of the compound according to claim 1 to a patient.

17. The method according to claim 16, wherein said disease is selected from the group consisting of metabolic syndrome, obesity, dyslipidemia, pathoglycemia, insulin resistance, and tumors.

18. A process for preparation of the compound of claim 1 in which R is C1-C9 alkyl, comprising the steps according to:
    Scheme One:
        Coupling the intermediate compounds II and III together in a solvent under the action of an alkali, resulting in the compound I; wherein said alkali is an organic or inorganic alkali, the inorganic alkali is an alkali metal carbonate, a soluble alkaline earth metal carbonate, ammonium carbonate, or any mixture thereof; the organic alkali is triethylamine; said solvent is acetonitrile, dimethylformamide, dimethyl sulfoxide, tetrahydrofuran, dioxane, or any mixtures thereof; the reaction temperature is at 0-100° C.; and the reaction time is 1-12 hours;

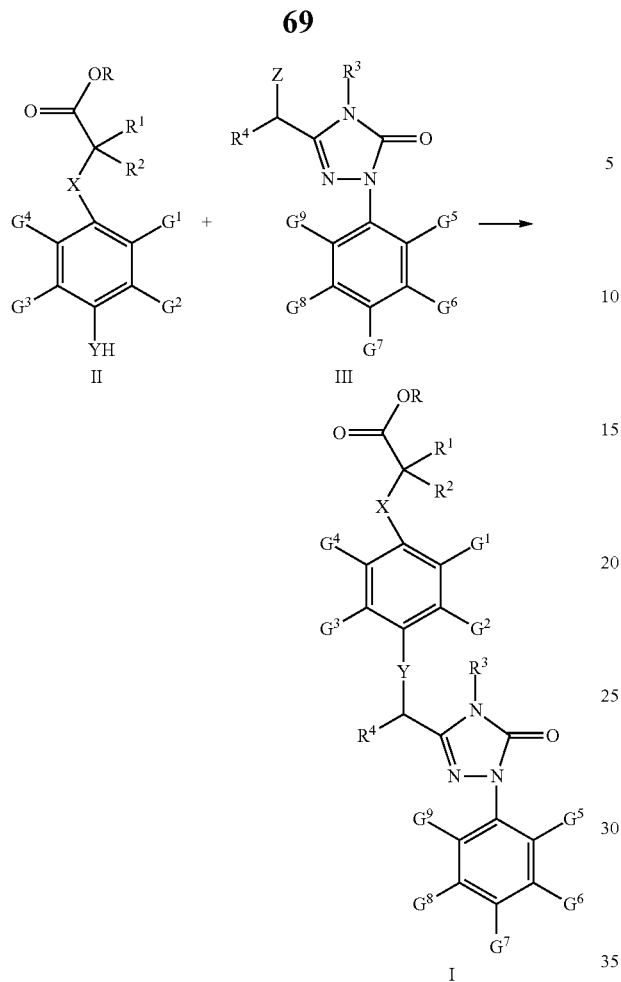

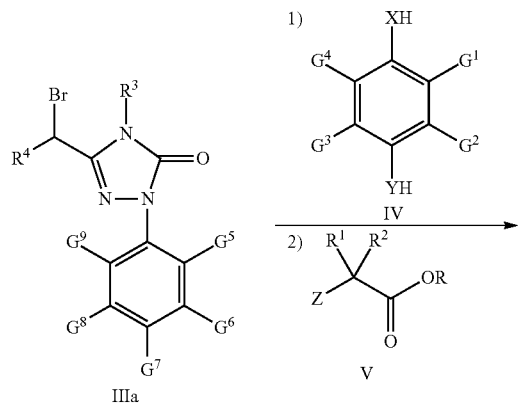

wherein
Z is Cl or Br;
X, Y, R, $R^1$, $R^2$, $R^3$, $R^4$, $G^1$, $G^2$, $G^3$, $G^4$, $G^5$, $G^6$, $G^7$, $G^8$, and $G^9$ are the same as defined in claim 1; or Scheme Two:
In a continuous reaction process with a carbonate salt, reacting the compound IIIa firstly with a compound IV and then with a compound V, resulting in the compound I without separation of the intermediates during the course of the reaction, using a solvent selected from acetonitrile, tetrahydrofuran, dioxane and any mixtures thereof; and using a carbonate salt selected from the group consisting of potassium carbonate, sodium carbonate, strontium carbonate, and ammonium carbonate,

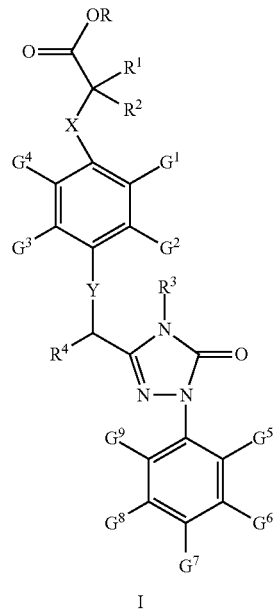

wherein

Z is Cl or Br; and

X, Y, R, $R^1$, $R^2$, $R^3$, $R^4$, $G^1$, $G^2$, $G^3$, $G^4$, $G^5$, $G^6$, $G^7$, $G^8$, and $G^9$ are the same as defined in claim 1.

19. A process for preparation of the compound of claim 1, in which R is H, comprising a step of alkaline hydrolysis of the compound I with R being C1-C9 alkyl using the following hydrolyzing conditions: the alkali used is sodium hydroxide, lithium hydroxide, or potassium hydroxide; the solvent system used is selected from a C1-C4 alcohol-water system with an alcohol/water ratio in the range of 9:1-1:1 (vol/vol), a tetrahydrofuran-water system with a THF/water ratio in the range of 9:1-1:1 (vol/vol), and an alcohol-dichloromethane-water system with an alcohol/dichloromethane/water ratio in the range of 9-1:9-1:1 (vol/vol/vol); the reaction temperature is at 0-80° C.; the reaction time is 1-12 hours.

20. A method of treating a disease treatable by activating the peroxisome proliferator-activated receptor subtype δ (PPARδ), comprising a step of administrating a therapeutically effective amount of the compound formula (I) of claim 1 to patient, said disease is metabolic syndrome, obesity, dyslipidemia, pathoglycemia, insulin resistance, senile dementia, or tumors.

21. The process according to claim 19, wherein the reaction temperature is at 20-40° C., and the reaction time is 2-4 hours.

* * * * *